US009901611B2

(12) United States Patent
Demopoulos et al.

(10) Patent No.: US 9,901,611 B2
(45) Date of Patent: Feb. 27, 2018

(54) GLUTATHIONE FORMULATION AND METHOD OF USE

(71) Applicant: Molecular Defenses Corporation, New York, NY (US)

(72) Inventors: Harry B. Demopoulos, Scarsdale, NY (US); Kevin Davis, New York, NY (US)

(73) Assignee: Molecular Defenses Corporation, New York, NY (US)

( * ) Notice: Subject to any disclaimer, the term of this patent is extended or adjusted under 35 U.S.C. 154(b) by 0 days.

(21) Appl. No.: 15/187,270

(22) Filed: Jun. 20, 2016

(65) Prior Publication Data

US 2016/0367621 A1 Dec. 22, 2016

Related U.S. Application Data

(60) Provisional application No. 62/182,229, filed on Jun. 19, 2015.

(51) Int. Cl.
*A61K 47/22* (2006.01)
*A61K 9/56* (2006.01)
*A61K 38/06* (2006.01)
*A61K 9/48* (2006.01)
*A61K 9/14* (2006.01)
*A61K 9/00* (2006.01)

(52) U.S. Cl.
CPC .......... *A61K 38/063* (2013.01); *A61K 9/0053* (2013.01); *A61K 9/145* (2013.01); *A61K 9/4833* (2013.01); *A61K 9/4858* (2013.01)

(58) Field of Classification Search
CPC .. A61K 2300/00; A61K 31/375; A61K 33/10; A61K 38/063; A61K 31/015; A61K 31/195; A61K 31/355; A61K 31/44; A61K 31/455; A61K 31/51; A61K 31/525; A61K 31/59; A61K 31/714; A61K 31/198
See application file for complete search history.

(56) References Cited

U.S. PATENT DOCUMENTS

| | | |
|---|---|---|
| 4,454,125 A | 6/1984 | Demopoulos |
| 4,477,435 A | 10/1984 | Courtois et al. |
| 4,534,967 A | 8/1985 | Jacobson et al. |
| 4,670,257 A | 6/1987 | Guedon born Saglier et al. |
| 4,770,877 A | 9/1988 | Jacobson |
| 4,859,668 A | 8/1989 | Noga et al. |
| 4,996,159 A | 2/1991 | Glaser |
| 5,010,000 A | 4/1991 | Palva |
| 5,204,114 A | 4/1993 | Demopoulos et al. |
| 5,326,757 A * | 7/1994 | Demopoulos ........ A61K 31/015 424/451 |
| 5,545,569 A | 8/1996 | Grainger et al. |
| 5,595,722 A | 1/1997 | Grainger et al. |
| 5,770,609 A | 6/1998 | Grainger et al. |
| 5,840,686 A | 11/1998 | Chader et al. |
| 5,847,007 A | 12/1998 | Grainger et al. |
| 6,069,167 A | 5/2000 | Sokol |
| 6,159,500 A | 12/2000 | Demopoulos et al. |
| 6,166,090 A | 12/2000 | Grainger et al. |
| 6,197,749 B1 | 3/2001 | Hamuro et al. |
| 6,197,789 B1 | 3/2001 | Grainger et al. |
| 6,204,248 B1 | 3/2001 | Demopoulos et al. |
| 6,251,920 B1 | 6/2001 | Grainger et al. |
| 6,262,019 B1 | 7/2001 | Keller et al. |
| 6,262,079 B1 | 7/2001 | Grainger et al. |
| 6,312,734 B1 | 11/2001 | Kozhemyakin et al. |
| 6,346,547 B1 | 2/2002 | Tzodikov |
| 6,350,467 B1 | 2/2002 | Demopoulos et al. |
| 6,395,494 B1 | 5/2002 | Grainger et al. |
| 6,423,687 B1 | 7/2002 | Demopolos et al. |
| 6,444,221 B1 | 9/2002 | Shapiro |
| 6,511,800 B1 | 1/2003 | Singh |
| 6,586,404 B1 | 7/2003 | Demopolos et al. |
| 6,596,762 B2 | 7/2003 | Sokol |
| 6,709,835 B2 | 3/2004 | Crawford |
| 6,764,693 B1 | 7/2004 | Smith |
| 6,835,811 B1 | 12/2004 | Harbin et al. |
| 6,896,899 B2 | 5/2005 | Demopolos et al. |
| 6,949,382 B2 | 9/2005 | Crawford |
| 7,045,292 B2 | 5/2006 | Mai |
| 7,049,058 B2 | 5/2006 | Singh |
| 7,078,064 B2 | 7/2006 | Labrecky |
| 7,094,550 B2 | 8/2006 | Grainger et al. |
| 7,145,025 B2 | 12/2006 | Lockwood et al. |
| 7,169,412 B2 | 1/2007 | Kozhemyakin et al. |
| 7,179,791 B2 | 2/2007 | Stamler et al. |
| RE39,705 E | 6/2007 | Keller et al. |
| 7,238,814 B2 | 7/2007 | Marek et al. |
| 7,241,461 B2 | 7/2007 | Myhill et al. |
| 7,279,301 B2 | 10/2007 | Crawford |
| 7,317,008 B2 | 1/2008 | Lockwood et al. |
| 7,320,997 B2 | 1/2008 | Lockwood et al. |
| 7,345,091 B2 | 3/2008 | Lockwood et al. |

(Continued)

FOREIGN PATENT DOCUMENTS

| | | | | |
|---|---|---|---|---|
| WO | WO98/29101 | * | 7/1998 | ............... A61K 9/20 |
| WO | 1998/029101 A1 | | 9/1998 | |

OTHER PUBLICATIONS

International Search Report for PCT/US2016/038381 dated Oct. 6, 2016.

(Continued)

*Primary Examiner* — Audrea Buckley
(74) *Attorney, Agent, or Firm* — Steven M. Hoffberg; Tully Rinckey PLLC

(57) ABSTRACT

The use of glutathione to treat or prophylax viral, bacterial, chemical, and nuclear agents, or to treat or prophylax radiation injury to humans due to release of radioactive elements. The preferred formulation is an oral dosage form, with reduced glutathione stabilized by ascorbic acid, packaged to under controlled humidity and temperature conditions to ensure creation of charge transfer complexes that ensure consistent packaging, insignificant oxidation during packaging and subsequent normal storage, and high oral bioavailability for humans.

20 Claims, No Drawings

(56) References Cited

U.S. PATENT DOCUMENTS

| | | |
|---|---|---|
| 7,371,411 B2 | 5/2008 | Kozhemyakin et al. |
| 7,375,133 B2 | 5/2008 | Lockwood et al. |
| 7,378,387 B2 | 5/2008 | Hamuro et al. |
| 7,384,655 B2 | 6/2008 | Myhill et al. |
| 7,396,659 B2 | 7/2008 | Singh |
| 7,407,986 B2 | 8/2008 | Gao et al. |
| 7,449,451 B2 | 11/2008 | Prasad et al. |
| 7,449,546 B2 | 11/2008 | Harbin et al. |
| 7,501,000 B2 | 3/2009 | Rosenflanz et al. |
| 7,521,584 B2 | 4/2009 | Lockwood et al. |
| RE40,849 E | 7/2009 | Keller et al. |
| 7,579,026 B2 | 8/2009 | Myhill et al. |
| 7,592,449 B2 | 9/2009 | Lockwood et al. |
| 7,615,535 B2 | 11/2009 | Stamler et al. |
| 7,691,901 B2 | 4/2010 | Lockwood et al. |
| 7,709,460 B2 | 5/2010 | McCaddon |
| 7,723,327 B2 | 5/2010 | Lockwood et al. |
| 7,763,649 B2 | 7/2010 | Lockwood et al. |
| 7,923,045 B2 | 4/2011 | Myhill et al. |
| 7,951,847 B2 | 5/2011 | Kaiser |
| 8,067,537 B2 | 11/2011 | Furukawa et al. |
| 8,093,207 B2 | 1/2012 | Stern |
| 8,114,913 B1 | 2/2012 | Guilford et al. |
| 8,147,869 B2 | 4/2012 | Guilford et al. |
| 8,178,516 B2 | 5/2012 | Shapiro |
| 8,217,006 B2 | 7/2012 | Stamler et al. |
| 8,217,084 B2 | 7/2012 | Ott |
| 8,221,805 B2 | 7/2012 | Myhill et al. |
| 8,252,325 B2 | 8/2012 | Guilford et al. |
| 8,303,949 B2 | 11/2012 | Gao et al. |
| 8,349,359 B2 | 1/2013 | Guilford et al. |
| 8,361,512 B2 | 1/2013 | Kaiser |
| 8,426,368 B2 | 4/2013 | Haley et al. |
| 8,435,574 B2 | 5/2013 | Myhill et al. |
| 8,501,700 B2 | 8/2013 | Nagasawa |
| 8,507,219 B2 | 8/2013 | Singh |
| 8,518,869 B2 | 8/2013 | Hallstrom et al. |
| 8,575,218 B2 | 11/2013 | Haley et al. |
| 8,591,876 B2 | 11/2013 | Bauman et al. |
| 8,592,392 B2 | 11/2013 | Prasad et al. |
| 8,602,961 B2 | 12/2013 | Schmidt |
| 8,679,530 B2 | 3/2014 | Guilford et al. |
| 8,709,406 B2 | 4/2014 | Gao et al. |
| 8,734,316 B2 | 5/2014 | Schmidt |
| 8,911,724 B2 | 12/2014 | Kaiser |
| 8,950,583 B2 | 2/2015 | Haley et al. |
| 8,981,139 B2 | 3/2015 | Schoenfisch et al. |
| 9,040,082 B2 | 5/2015 | Kaiser |
| 9,062,086 B2 | 6/2015 | Xie et al. |
| 9,144,570 B2 | 9/2015 | Nagasawa |
| 9,149,451 B1 | 10/2015 | Schmidt |
| 9,229,014 B2 | 1/2016 | Crum |
| 9,265,808 B2 | 2/2016 | McCord et al. |
| 9,308,234 B2 | 4/2016 | Arnold et al. |
| 2001/0000784 A1 | 5/2001 | Hamuro et al. |
| 2002/0002136 A1 | 1/2002 | Hebert |
| 2002/0136763 A1 | 9/2002 | Demopoulos et al. |
| 2002/0182585 A1 | 12/2002 | Kindness et al. |
| 2003/0129262 A1 | 7/2003 | Epner et al. |
| 2003/0211491 A1 | 11/2003 | Mai |
| 2004/0022873 A1 | 2/2004 | Guilford et al. |
| 2004/0071770 A1 | 4/2004 | Smith |
| 2004/0105894 A1 | 6/2004 | Gupta |
| 2004/0157783 A1 | 8/2004 | McCaddon |
| 2005/0090553 A1 | 4/2005 | Shapiro |
| 2005/0123628 A1 | 6/2005 | Zabrecky |
| 2005/0130905 A1 | 6/2005 | Harbin et al. |
| 2005/0222046 A1 | 10/2005 | Demopoulos et al. |
| 2005/0226942 A1 | 10/2005 | Myhill et al. |
| 2005/0239886 A1 | 10/2005 | Hamuro et al. |
| 2006/0008543 A1 | 1/2006 | Myhill et al. |
| 2006/0008544 A1 | 1/2006 | Myhill et al. |
| 2006/0099244 A1 | 5/2006 | Guilford |
| 2006/0105972 A1 | 5/2006 | Nagasawa |
| 2007/0004035 A1 | 1/2007 | Sitzmann |
| 2007/0026090 A1 | 2/2007 | Tirosh et al. |
| 2007/0053970 A1 | 3/2007 | Guilford |
| 2007/0065497 A1 | 3/2007 | Guilford |
| 2008/0234380 A1 | 9/2008 | Shapiro |
| 2009/0042822 A1 | 2/2009 | Nagasawa |
| 2009/0068253 A1 | 3/2009 | Guilford |
| 2009/0176715 A1 | 7/2009 | Javitt |
| 2009/0311350 A1 | 12/2009 | Myhill et al. |
| 2010/0166796 A1 | 7/2010 | Keller et al. |
| 2010/0166846 A1 | 7/2010 | Guilford |
| 2010/0233193 A1 | 9/2010 | Guilford et al. |
| 2010/0233297 A1 | 9/2010 | Guilford et al. |
| 2010/0291196 A1 | 11/2010 | Guilford |
| 2010/0316700 A1 | 12/2010 | Guilford |
| 2011/0077194 A1 | 3/2011 | McCaddon |
| 2011/0111002 A1 | 5/2011 | Pop |
| 2011/0129523 A1 | 6/2011 | Guilford et al. |
| 2011/0151030 A1 | 6/2011 | Myhill et al. |
| 2011/0305752 A1 | 12/2011 | Guilford et al. |
| 2012/0021073 A1 | 1/2012 | Guilford et al. |
| 2012/0087994 A1 | 4/2012 | Guilford et al. |
| 2012/0135068 A1 | 5/2012 | Guilford et al. |
| 2012/0141608 A1 | 6/2012 | Guilford et al. |
| 2012/0244212 A1 | 9/2012 | Guilford |
| 2012/0244235 A1 | 9/2012 | Myhill et al. |
| 2012/0245343 A1 | 9/2012 | Jang |
| 2013/0129815 A1 | 5/2013 | Guilford et al. |
| 2013/0202681 A1 | 8/2013 | Guilford |
| 2013/0317072 A1 | 11/2013 | Nagasawa |
| 2014/0045874 A1 | 2/2014 | Tolleth et al. |
| 2014/0100283 A1 | 4/2014 | Mahoney |
| 2014/0256760 A1 | 9/2014 | Tolleth et al. |
| 2014/0271816 A1 | 9/2014 | Guilford |
| 2014/0271923 A1 | 9/2014 | Reid |
| 2015/0030668 A1 | 1/2015 | Guilford |
| 2015/0038577 A1 | 2/2015 | Xie et al. |
| 2015/0209316 A1 | 7/2015 | Ochiai et al. |
| 2015/0246018 A1 | 9/2015 | Xie et al. |
| 2016/0068904 A1 | 3/2016 | Harper |
| 2016/0082029 A1 | 3/2016 | Nagasawa |
| 2016/0158308 A1 | 6/2016 | Brown et al. |

OTHER PUBLICATIONS

Written Opinion for PCT/US2016/038381 dated Sep. 27, 2016.

Bailey, A. C. "Electrostatic phenomena during powder handling", Powder Technology, 37(1), 71-85 (1984).

Peart, J. "Powder electrostatics: theory, techniques and applications", KONA Powder and Particle Journal, 19, 34-45 (2001).

\* cited by examiner

GLUTATHIONE FORMULATION AND METHOD OF USE

CROSS REFERENCE TO RELATED APPLICATIONS

The present application claims benefit of priority under 35 U.S.C. § 119(e) from U.S. Provisional Patent Application No. 62/182,229, filed Jun. 19, 2015, the entirety of which are each expressly incorporated herein by reference.

FIELD OF THE INVENTION

The present invention relates to the use of glutathione for treatment and/or prophylaxis of various conditions.

BACKGROUND OF THE INVENTION

The ubiquitous tripeptide L-glutathione (GSH) (gamma-glutamyl-cysteinyl-glycine), is a well-known biological antioxidant, and in fact is believed to be the primary intracellular antioxidant for higher organisms. When oxidized, it forms a dimer (GSSG), which may be recycled in organs having glutathione reductase. Glutathione may be transported through membranes by the sodium-dependent glutamate pump. Tanuguchi, N., et al. Eds., Glutathione Centennial, Academic Press, New York (1989). Glutathione is widely distributed in Nature, including yeast cells, botanic life and animals. It is made in the same way in humans by two different enzymes, and this is relevant to understanding the properties of glutathione (12).

GSH is "bent" in the same way across thousands of life forms, by two enzymes, and has evolved over a long time to specifically position its critical thiol. For comparison, the thiol of cysteine, alone, is overexposed and over reactive, and the thiol of homocysteine even more so, creating a highly destructive sulfur radical that disrupts endothelium in homocysteinemia. N-acetyl cysteine (NAC), when taken orally, loses the N-acetyl in the stomach, thereby leading to uncontrolled oxidation and a range of toxicities in humans.

The properties of GSH derive from its controlled reactivity, its ability to maintain a physiologically favorable Redox potential, its antioxidant properties in all subcellular compartments, the existence of avid glutathione transporters on cell membranes and mitochondria, and the fact that these properties are supported by enzymes: (i) that synthesize GSH; (ii) that amplify particular properties, such as GSH peroxidases and S-transferases and; (iii) enzymes that restore GSH after it has been used, GSH reductase. Loss of activity of glutathione peroxidase 4 (GPX4) in a process called ferroptosis, leads to accumulation of lipid-based reactive oxygen species (ROS), particularly lipid hydroperoxides.

GSH functions directly or indirectly in many important biological phenomena, including the synthesis of proteins and DNA, transport, enzyme activity, metabolism, and protection of cells from free-radical mediated damage. GSH is one of the primary cellular antioxidants responsible for maintaining the proper oxidation state within the body. GSH is synthesized by most cells, and is also supplied in the diet. GSH has been shown to recycle oxidized biomolecules back to their active, reduced forms. Because of the existing mechanisms for controlling interconversion of reduced and oxidized GSH, an alteration of the level of reduced GSH, e.g., by administration of GSH to an organism, will tend to shift the cells of the organism to a more reduced redox potential. Likewise, subjecting the organism to oxidative stress or free radicals will tend to shift the cells to a more oxidized potential. It is well known that certain cellular processes are responsive to redox potential. Reduced GSH produced in human adults from oxidized GSSG primarily by the liver, and to a smaller extent, by the skeletal muscle, red blood cells, and white cells. About 80% of the 8-10 grams glutathione produced daily is by the liver and distributed through the blood stream to the other tissues.

A deficiency of GSH in cells may lead to excess free radicals, which cause macromolecular breakdown, lipid peroxidation, buildup of toxins, and ultimately cell death. Because of the importance of GSH in preventing this cellular oxidation, GSH is continuously supplied to the tissues. However, under certain conditions, the normal, physiologic supplies of GSH are insufficient, distribution inadequate or local oxidative demands too high to prevent cellular oxidation. Under certain conditions, the production of and demand for GSH are mismatched, leading to insufficient levels on an organismal level. In other cases, certain tissues or biological processes consume GSH so that the intracellular levels are suppressed. In either case, by increasing the serum levels of GSH, increased amounts may be directed into the cells. In cellular uptake facilitated transport systems, the concentration gradient which drives uptake is increased.

As with all nutrients, eating or orally ingesting the nutrient would generally be considered a desired method for increase body levels thereof. Thus, attempts at oral GSH treatments were known. Prior work by the present inventor demonstrates efficacious administration by oral administration on an empty stomach. See, U.S. Pat. No. 6,159,500, and the below, each of which is expressly incorporated herein by reference. See also: U.S. Pat. Nos. 9,308,234; 9,062,086; 9,040,082; 8,911,724; 8,592,392; 8,361,512; 8,349,359; 8,252,325; 8,147,869; 8,114,913; 7,951,847; 7,709,460; RE40,849; 7,449,546; 7,449,451; 7,378,387; RE39,705; 7,078,064; 6,896,899; 6,835,811; 6,586,404; 6,423,687; 6,350,467; 6,262,019; 6,204,248; 6,197,749; 6,159,500; 9,265,808; 9,229,014; 9,149,451; 9,144,570; 8,981,139; 8,950,583; 8,734,316; 8,709,406; 8,679,530; 8,602,961; 8,591,876; 8,575,218; 8,518,869; 8,507,219; 8,501,700; 8,435,574; 8,426,368; 8,303,949; 8,221,805; 8,217,084; 8,217,006; 8,178,516; 8,093,207; 8,067,537; 7,923,045; 7,763,649; 7,723,327; 7,691,901; 7,615,535; 7,592,449; 7,579,026; 7,521,584; 7,407,986; 7,396,659; 7,384,655; 7,375,133; 7,371,411; 7,345,091; 7,320,997; 7,317,008; 7,279,301; 7,241,461; 7,238,814; 7,179,791; 7,169,412; 7,145,025; 7,094,550; 7,049,058; 7,045,292; 6,949,382; 6,896,899; 6,764,693; 6,709,835; 6,596,762; 6,586,404; 6,511,800; 6,444,221; 6,423,687; 6,395,494; 6,350,467; 6,346,547; 6,312,734; 6,262,079; 6,251,920; 6,204,248; 6,197,789; 6,166,090; 6,159,500; 6,069,167; 5,847,007; 5,770,609; 5,595,722; 5,545,569; 5,326,757; 5,204,114; 4,859,668; 20160082029; 2015028393; 2014027144; 2014019385; 2014014171; 20130317072; 20120244235; 20110151030; 20110129523; 20100291196; 20090311350; 20090042822; 20080234380; 20070065497; 20070053970; 20070026090; 20070004035; 20060105972; 20060008544; 20060008543; 20050226942; 20050222046; 20050090553; 20040105894; 20040071770; 20030211491; 20030129262; 20020136763; 20020002136; 20140256760; 20140045874; 20120245343; 20160158308; 20160068904; 20150246018; 20150209316; 20150038577; 20150030668; 20140271923; 20140271816; 20140100283; 20130202681; 20130129815; 20120244212; 20120141608; 20120135068; 20120087994; 20120021073; 20110305752; 20110111002; 20110077194; 20100316700; 20100291196; 20100233297; 20100233193;

20100166846; 20100166796; 20090176715; 20090068253; 20070053970; 20060099244; 20050239886; 20050222046; 20050130905; 20050123628; 20040157783; 20040022873; 20020182585; 20020136763; 20010000784. See, www.fda.gov/ucm/groups/fdagov-public/@fdagov-foods-gen/documents/document/ucm264131.pdf.

Metabolism of GSH.

The synthesis of GSH is dependent upon the availability of cysteine either supplied directly from the diet or cysteine or indirectly from methionine via the transsulfuration pathway. GSH synthesis and metabolism is governed by the enzymes of the γ-glutamyl cycle. GSH is synthesized intracellularly by the consecutive actions of γ-glutamylcysteinyl synthetase (Reaction 1) and GSH synthetase (Reaction 2). The action of the latter enzyme is feedback inhibited by GSH. The breakdown of GSH (and also of its oxidized form, GSSG) is catalyzed by γ-glutamyl transpeptidase, which catalyzes the transfer of the gamma-glutamyl moiety to acceptors such as SH-containing amino acids, certain dipeptides, and GSH itself (Reaction 3). The cellular turnover of GSH is associated with its transport, in the form of GSH, across cell membranes, where the majority of the transpeptidase is found. During this transport, GSH interacts with γ-glutamyl transferase (also known as transpeptidase) to form γ-glutamyl amino acids which are transported into cells. Intracellular γ-glutamyl amino acids are substrates of γ-glutamyl cyclotransferase (Reaction 4) which converts these compounds into the corresponding amino acids and 5-oxo-L-proline. The ATP-dependent conversion of 5-L-oxoproline to L-glutamate is catalyzed by the intracellular enzyme 5-oxo-prolinase (Reaction 5). The cysteinylglycine formed in the transpeptidase reaction is split by dipeptidase (Reaction 6). These six reactions constitute the γ-glutamyl cycle, which accounts for the synthesis and enzymatic degradation of GSH.

Two of the enzymes of the cycle also function in the metabolism of S-substituted GSH derivatives, which may be formed nonenzymatically by reaction of GSH with certain electrophilic compounds or by GSH S-transferases (Reaction 7). The γ-glutamyl moiety of such conjugates is removed by the action of γ-glutamyl transpeptidase (Reaction 3), a reaction facilitated by γ-glutamyl amino acid formation. The resulting S-substituted cysteinylglycines are cleaved by dipeptidase (Reaction 6A) to yield the corresponding S-substituted cysteines, which may undergo N-acetylation (Reaction 8) or an additional transpeptidation reaction to form the corresponding γ-glutamyl derivative (Reaction 3A).

Intracellular GSH is converted to its oxidized, dimeric form (GSSG) by selenium-containing GSH peroxidase, which catalyzes the reduction of $H_2O_2$ and other peroxides (Reaction 9). GSH is also converted to GSSG by transhydrogenation (Reaction 10). Reduction of GSSG to GSH is mediated by the widely-distributed enzyme GSSG reductase which uses NADPH (Reaction 11). Extracellular conversion of GSH to GSSG has also been reported; the overall reaction requires $O_2$ and leads to the formation of $H_2O_2$ (Reaction 12). GSSG is also formed by reaction of GSH with free radicals. The GSH-dependent antioxidant system consists of GSH plus two enzymes: GSH peroxidase and GSH reductase. As this system operates, GSH cycles between its oxidized (GSSG) and reduced (GSH) forms.

Lipid hydroperoxides, which are formed during the peroxidation of lipids containing unsaturated fatty acids, are reduced, not by the usual GSH peroxidase, but by a special enzyme designed specifically to handle peroxidized fatty acids in phospholipids. This enzyme, known as phospholipid hydroperoxide GSH peroxidase is protein that can reduce both $H_2O_2$ and lipid hydroperoxides to the corresponding hydroxides (water and a lipid hydroxide, respectively). In contrast to the phospholipid hydroperoxide GSH peroxidase, ordinary GSH peroxidase is unable to act on lipid hydroperoxides.

Transport of GSH

The intracellular level of GSH in mammalian cells is in the range of 0.5-10 mM, while μM concentrations are typically found in blood plasma. Intracellular GSH is normally over 99% reduced form (GSH). The normal healthy adult human liver synthesizes 8-10 grams of GSH daily. Normally, there is an appreciable flow of GSH from liver into plasma. The major organs involved in the inter-organ transport of GSH are the liver and the kidney, which is the primary organ for clearance of circulating GSH. It has been estimated to account for 50-67% of net plasma GSH turnover. Several investigators have found that during a single pass through the kidney, 80% or more of the plasma GSH is extracted, greatly exceeding the amount which could be accounted for by glomerular filtration. While the filtered GSH is degraded stepwise by the action of the brush-border enzymes γ-glutamyltransferase and cysteinylglycine dipeptidase, the remainder of the GSH appears to be transported via an unrelated, Na+-dependent system present in basal-lateral membranes. GSH transported from hepatocytes interacts with the transpeptidase of ductile cells, and there is a substantial reabsorption of metabolites by ductule endothelium. In the rat, about 12 and 4 nmoles/g/min of GSH appear in the hepatic vein and bile, respectively.

GSH exists in plasma in four forms: reduced GSH (GSH), oxidized GSH (GSSG), mixed disulfide with cysteine (CySSG) and protein bound through a SH linkage (GSSPr). The distribution of GSH equivalents is significantly different than that of cyst(e)ine, and when either GSH or cysteine is added at physiological concentration, a rapid redistribution occurs. The distribution of GSH equivalents in rat plasma is 70.0% protein bound, with the remaining 30% apportioned as follows: 28.0% GSH, 9.5% GSSG, and 62.6% as the mixed disulfide with cysteine. The distribution of cysteine equivalents was found to be 23% protein bound, with the remaining 77% distributed as follows: 5.9% cysteine, 83.1% cystine, and 10.8% as the mixed disulfide with GSH. Plasma thiols and disulfides are not in equilibrium, but appear to be in a steady state maintained in part by transport of these compounds between tissues during the interorgan phase of their metabolism. The large amounts of protein-bound GSH and cysteine provide substantial buffering which must be considered in the analysis of transient changes in GSH and cysteine. This buffering may protect against transient thiol-disulfide redox changes which could affect the structure and activity of plasma and plasma membrane proteins. In erythrocytes, GSH has been implicated in reactions which maintain the native structure of hemoglobin and of enzymes and membrane proteins. GSH is present in erythrocytes at levels 1000 times greater than in plasma. It functions as the major small molecule antioxidant defense against toxic free radicals, an inevitable by-product of the erythrocytes' handling of 02.

GSH and the Immune System

Thiols and especially of GSH are important to lymphocyte function. Adequate concentrations of GSH are required for mixed lymphocyte reactions, T-cell proliferation, T- and B-cell differentiation, cytotoxic T-cell activity, and natural killer cell activity. Adequate GSH levels have been shown to be necessary for microtubule polymerization in neutrophils. Intraperitoneally administered GSH augments the activation of cytotoxic T-lymphocytes in mice, and dietary GSH was found to improve the splenic status of GSH in aging mice, and to enhance T-cell-mediated immune responses.

The presence of macrophages can cause a substantial increase of the intracellular GSH levels of activated lymphocytes in their vicinity. Macrophages consume cystine via a strong membrane transport system, and generate large amounts of cysteine which they release into the extracellular space. It has been demonstrated that macrophage GSH levels (and therefore cysteine equivalents) can be augmented by exogenous GSH. T-cells cannot produce their own cysteine, and it is required by T-cells as the rate-limiting precursor of GSH synthesis. The intracellular GSH level and the DNA synthesis activity in mitogenically-stimulated lymphocytes are strongly increased by exogenous cysteine, but not cystine. In T-cells, the membrane transport activity for cystine is ten-fold lower than that for cysteine. As a consequence, T-cells have a low baseline supply of cysteine, even under healthy physiological conditions. The cysteine supply function of the macrophages is an important part of the mechanism which enables T-cells to shift from a GSH-poor to a GSH-rich state.

The importance of the intracellular GSH concentration for the activation of T-cells is well established. It has been reported that GSH levels in T-cells rise after treatment with GSH; it is unclear whether this increase is due to uptake of the intact GSH or via extracellular breakdown, transport of breakdown products, and subsequent intracellular GSH synthesis. Decreasing GSH by 10-40% can completely inhibit T-cell activation in vitro. Depletion of intracellular GSH has been shown to inhibit the mitogenically-induced nuclear size transformation in the early phase of the response. Cysteine and GSH depletion also affects the function of activated T-cells, such as cycling T-cell clones and activated cytotoxic T-lymphocyte precursor cells in the late phase of the allogenic mixed lymphocyte culture. DNA synthesis and protein synthesis in IL-2 dependent T-cell clones, as well as the continued growth of preactivated CTL precursor cells and/or their functional differentiation into cytotoxic effector cells are strongly sensitive to GSH depletion.

The activation of physiologic activity of mouse cytotoxic T-lymphocytes in vivo was found to be augmented by intraperitoneal (i.p.) GSH in the late phase but not in the early phase of the response. The injection of GSH on the third day post immunization mediated a 5-fold augmentation of cytotoxic activity. Dietary GSH supplementation can reverse age-associated decline of immune response in rats, as demonstrated by maintenance of Concanavalin A stimulated proliferation of splenocytes in older rats.

GSH status is a major determinant of protection against oxidative injury. GSH acts on the one hand by reducing hydrogen peroxide and organic hydroperoxides in reactions catalyzed by GSH peroxidases, and on the other hand by conjugating with electrophilic xenobiotic intermediates capable of inducing oxidant stress. The epithelial cells of the renal tubule have a high concentration of GSH, no doubt because the kidneys function in toxin and waste elimination, and the epithelium of the renal tubule is exposed to a variety of toxic compounds. GSH, transported into cells from the extracellular medium, substantially protects isolated cells from intestine and lung are against t-butylhydroperoxide, menadione or paraquat-induced toxicity. Isolated kidney cells also transport GSH, which can supplement endogenous synthesis of GSH to protect against oxidant injury. Hepatic GSH content has also been reported to rise, indeed to double, in the presence of exogenous GSH. This may be due either to direct transport, as has been reported for intestinal and alveolar cells, or via extracellular degradation, transport, and intracellular resynthesis.

The nucleophilic sulfur atom of the cysteine moiety of GSH serves as a mechanism to protect cells from harmful effects induced by toxic electrophiles. The concept that GSH S-conjugate biosynthesis is an important mechanism of drug and chemical detoxification is well established. GSH conjugation of a substrate generally requires both GSH and GSH-S-transferase activity. The existence of multiple GSH-S-transferases with specific, but also overlapping, substrate specificities enables the enzyme system to handle a wide range of compounds.

Several classes of compounds are believed to be converted by GSH conjugate formation to toxic metabolites. Halogenated alkenes, hydroquinones, and quinones have been shown to form toxic metabolites via the formation of S-conjugates with GSH. The kidney is the main target organ for compounds metabolized by this pathway. Selective toxicity to the kidney is the result of the kidney's ability to accumulate intermediates formed by the processing of S-conjugates in the proximal tubular cells, and to bioactivate these intermediates to toxic metabolites.

The administration of morphine and related compounds to rats and mice results in a loss of up to approximately 50% of hepatic GSH. Morphine is known to be biotransformed into morphinone, a highly hepatotoxic compound, which is 9 times more toxic than morphine in mouse by subcutaneous injection, by morphine 6-dehydrogenase activity. Morphinone possesses an $\alpha,\beta$-unsaturated ketone, which allows it to form a GSH S-conjugate. The formation of this conjugate correlates with loss of cellular GSH. This pathway represents the main detoxification process for morphine. GSH pretreatment protects against morphine-induced lethality in mouse.

The deleterious effects of methylmercury on mouse neuroblastoma cells are largely prevented by coadministration of GSH. GSH may complex with methylmercury, prevent its transport into the cell, and increase cellular antioxidant capabilities to prevent cell damage. Methylmercury is believed to exert its deleterious effects on cellular microtubules via oxidation of tubulin SH, and by alterations due to peroxidative injury. GSH also protects against poisoning by other heavy metals such as nickel and cadmium.

Because of its known role in renal detoxification and its low toxicity, GSH has been explored as an adjunct therapy for patients undergoing cancer chemotherapy with nephrotoxic agents such as cisplatin, in order to reduce systemic toxicity. In one study, GSH was administered intravenously to patients with advanced neoplastic disease, in two divided doses of 2,500 mg, shortly before and after doses of cyclophosphamide. GSH was well-tolerated and did not produce unexpected toxicity. The lack of bladder damage, including microscopic hematuria, supports the protective role of this compound. Other studies have shown that i.v. GSH coadministration with cisplatin and/or cyclophosphamide combination therapy, reduces associated nephrotoxicity, while not unduly interfering with the desired cytotoxic effect of these drugs.

GSH is relatively unstable in alkaline or oxidative environments, and is not absorbed by the stomach. It is believed that GSH is absorbed, after oral administration, if at all, in the latter half of the duodenum and the beginning of the jejunum. It was also believed that orally administered GSH would tend to be degraded in the stomach, and that it is particularly degraded under alkaline conditions by desulfurases and peptidases present in the duodenum. While GSH may be degraded, transported as amino acids, and resynthesized in the cell, there may also be circumstances where GSH is transported into cells without degradation; and in fact the administration of cysteine or cysteine precursors may interfere with this process.

Pure GSH forms a flaky powder that retains a static electrical charge, due to triboelectric effects, making processing and formulation difficult. The powder particles may also have an electrostatic polarization, which is akin to an electret. GSH is a strong reducing agent, so that autooxidation occurs in the presence of oxygen or other oxidizing agents. U.S. Pat. No. 5,204,114, provides a method of manufacturing GSH tablets and capsules by the use of crystalline ascorbic acid as an additive to reduce triboelectric effects which interfere with high speed equipment and maintaining GSH in a reduced state. The GSH is well absorbed, and distributed into the Peripheral Blood Mononuclear Cells (PBMC's) starting within 0.5 hours after oral ingestion. A certain crystalline ascorbic acid is, in turn, disclosed in U.S. Pat. No. 4,454,125. This crystalline form is useful as a lubricating agent for machinery. Ascorbic acid has the advantage that it is well tolerated, antioxidant, and reduces the net static charge on the GSH.

A number of disease states have been specifically associated with reductions in GSH levels. Depressed GSH levels, either locally in particular organs, or systemically, have been associated with a number of clinically defined diseases and disease states. These include HIV/AIDS, diabetes and macular degeneration, all of which progress because of excessive free radical reactions and insufficient GSH. Other chronic conditions may also be associated with GSH deficiency, including heart failure and coronary artery restenosis post angioplasty.

Clinical and pre-clinical studies have demonstrated the linkage between a range of free radical disorders and insufficient GSH levels. Diabetic complications may be the result of hyperglycemic episodes that promote glycation of cellular enzymes and thereby inactivate GSH synthetic pathways. GSH deficiency occurs diabetics, which explains the prevalence of cataracts, hypertension, occlusive atherosclerosis, and susceptibility to infections in these patients.

GSH functions as a detoxicant by forming GSH S-conjugates with carcinogenic electrophiles, preventing reaction with DNA, and chelation complexes with heavy metals such as nickel, lead, cadmium, mercury, vanadium, and manganese. GSH also plays a role in metabolism of various drugs, such as opiates. It has been used as an adjunct therapy to treatment with nephrotoxic chemotherapeutic agents such as cisplatin, and has been reported to prevent doxorubicin-induced cardiomyopathy. GSH is also an important factor in the detoxification of acetaminophen and ethanol, two powerful hepatotoxins.

Pharmacokinetics of GSH

The pharmacokinetics of intravenously administered GSH were determined in the rat and interpreted by means of an open, two-compartment model. Following a bolus injection of 50-300 mmol/kg GSH, arterial plasma concentrations of (i) GSH, (ii) oxidized GSH/GSSG, (iii) total thiols, and (iv) soluble thiols minus GSH, were elevated and then rapidly decreased non-exponentially, as anticipated. With increasing dose, the rate constant for drug elimination and plasma clearance increased form 0.84 to 2.44 mL/min. and the half-life of the elimination phase decreased from 52.4 to 11.4 minutes. Both the apparent volume of distribution and the degree of penetration of GSH into the tissues were diminished with increasing dose (from 3.78 to 1.33 L/Kg and from 6.0 to 0.51 as $k_{12}/k_{21}$, respectively). The data indicate that GSH is rapidly eliminated. This is mainly due to rapid oxidation in plasma rather than by increased tissue extraction or volume distribution. Thus, plasma GSH levels appear be quickly regulated by which the body may maintain concentrations within narrow physiological limits.

When single doses of 600 mg GSH were administered intravenously to sheep, GSH levels in venous plasma and lung lymph rose transiently. The mean concentration was approximately 50 mM for venous plasma, peaking at 30 min, and returning to baseline after 45 minutes. Lung lymph peak level was about 100 mM at 15 min, returning to baseline after 30 minutes. Average epithelial lining fluid (ELF) levels were variable but showed no significant increase over baseline during the three hour observation period. Urine excretion was rapid with peak levels at 15 minutes. In both plasma and lung lymph, GSH accounted for greater than 95% of the total GSH (GSH plus GSSG). In ELF 75.4% of the baseline GSH was in the reduced form, whereas in urine 59.6% was present as GSH.

Orally ingested reduced GSH is absorbed intact from the small intestine in a rat model, specifically in the upper jejunum. It is noted that rat metabolism differs from man, and therefore the results of rat studies should be verified in man before the results are extrapolated. Plasma GSH concentration in rats increased from 15 to 30 mM after administration of GSH either as a liquid bolus (30 mM) or mixed (2.5-50 mg/g) in AIN-70 semi-synthetic diet (11). GSH concentration was maximal at 90-120 minutes after GSH administration and remained high for over 3 hours. Administration of the amino acid precursors of GSH had little or no effect on plasma GSH values, indicating that GSH catabolism and re-synthesis do not account for the increased GSH concentration seen. Inhibition of GSH synthesis and degradation by L-buthionine-[S,R]-sulfoximine (BSO) and acivicin showed that increased plasma GSH came mostly from absorption of intact GSH instead of GSH metabolites. Plasma protein-bound GSH also increased after GSH administration, with a time course similar to that observed for free plasma GSH. Thus, dietary GSH can be absorbed intact and results in a substantial increase in blood plasma GSH.

Administration of oral GSH increased hepatic GSH levels in: (i) rats fasted 48 hours, (ii) mice treated with GSH depletors, and (iii) mice treated with paracetamol (a drug which promotes a depletion of hepatic GSH followed by hepatic centrilobular necrosis). In these experiments, the animals were orally intubated with 1000 mg/kg body weight GSH. Mean pretreatment values in 48-hour fasted rats were 3.0-3.1 mmol/g fresh hepatic tissue. Mean values after treatment were 5.8, 4.2, and 7.0 mmol/g fresh hepatic tissue for 2.5, 10, and 24 hours post-treatment, respectively. Mice were given an oral dose of GSH (100 mg/kg) and concentrations of GSH were measured at 30, 45 and 60 min in blood plasma and after 1 hr in liver, kidney, heart, lung, brain, small intestine and skin. GSH concentrations in plasma increased from 30 mM to 75 mM within 30 min of oral GSH administration, consistent with a rapid flux of GSH from the intestinal lumen to plasma. No increases over control values were obtained in most tissues except lung over the same time course. Mice pretreated with the GSH synthesis inhibitor BSO had substantially decreased tissue concentrations of GSH, and oral administration of GSH to these animals resulted in statistically-significant increases in the GSH concentrations of kidney, heart, lung, brain, small intestine and skin but not in liver.

The kinetics and the effect of GSH on plasma and urine SH were studied in ten healthy human volunteers. Following the intravenous infusion of 2000 mg/m² of GSH the concentration of total GSH in plasma increased from 17.5±13.4 mmol/Liter (mean±SD) to 823±326 mmol/Liter. The volume of distribution of exogenous GSH was 176±107 Ml/Kg and the elimination rate constant was 0.063±0.027/minute, corresponding to a half-life of 14.1±9.2 minutes. Cysteine in plasma increased from 8.9±3.5 mmol/Liter to 114±45 mmol/Liter after the infusion. In spite of the increase in cysteine, the plasma concentration of total cyst(e)ine (i.e. cysteine, cystine, and mixed disulfides) decreased, suggesting an increased uptake of cysteine from plasma into cells. The urinary excretion of GSH and of cyst(e)ine was increased 300-fold and 10-fold respectively, in the 90 minutes following the infusion.

Normal healthy volunteers were given an oral dose of GSH to determine whether dietary GSH could raise plasma GSH levels. Results showed that an oral dose of GSH (15 mg/kg) raised plasma GSH levels in humans 1.5-10 fold over the basal concentration in four out of five subjects tested, with a mean value three times that of normal plasma GSH levels. Plasma GSH became maximal 1 hour after oral administration, dropping to approximately ½ maximal values after three hours. Equivalent amounts of GSH amino acid constituents failed to increase plasma levels of GSH. GSH bound to plasma proteins also increased with the same time course as seen with free GSH.

SUMMARY OF THE INVENTION

Pharmaceutical GSH is safe, stable, rapidly bioavailable and replenishes GSH lost continuously in viral infections, exposures to toxic chemicals, and radiation. It maintains intracellular levels needed to express four properties that are concentration dependent. GSH therapy: (1) assures GSH availability to support TH1 immunologic responses needed to recover from smallpox; (2) slows activation and over-expression of NF-κB and inflammatory cascades that cause cumulative tissue toxicities; (3) biochemically neutralizes reactive intermediates that otherwise cause cellular and tissue toxicities; (4) may disable the activities of key viral proteins, and curb replication. As a result, GSH therapy may decrease morbidity, as shown in examples of human and animal studies of HIV infection, other pox viruses, and hepatitis C.

Consistently normal intracellular concentrations of GSH help maintain the balance of T Helper 1 and 2 (Th1 and Th2) immunologic response patterns. When GSH is continuously lost, restorative GSH therapy rapidly up-regulates Th1, enhancing IFNγ and cell mediated immunity required for recovery, while down-regulating IL-4, a disadvantageous Th2 cytokine, when over-expressed during acute viral infections. This beneficial effect of GSH, required for recovery responses, has been demonstrated against other dangerous viruses, including pox viruses.

Consistently normal intracellular concentrations of GSH also sets a high reduction oxidation potential within cells, that slows activation and over-expression of NFκB, TNFα, IL-1β, adhesion molecules, cyclo-oxygenase-2, matrix metalloproteinases and inflammatory cascades. This mechanism is also demonstrated against other dangerous viruses, including pox viruses. The ability to help control such reactions indicates, potential uses of GSH in counter terrorism.

Biochemical neutralizing reactions: (a) GSH neutralizes reactive oxygen species (ROS) and reactive nitrogen species (RNS) continuously produced during viral infections that otherwise damage cell membrane lipids, proteins, and nucleic acids, and result in cellular and tissue toxicities; (b) GSH protects mitochondria against hydrogen peroxide, bio-energetic failure, and exaggerated, apoptotic processes that add to cumulative tissue toxicities; (c) consistently normal intracellular concentrations of GSH help control non enzymatic and enzymatic oxidations of arachidonic acid. Otherwise these cause tissue-disrupting excesses of reactive intermediates from lipid hydroperoxides (alkoxy radicals, LO., and hydroxyls, .OH). The ability to help control such reactions indicates further potential uses of GSH in counter terrorism.

As occurs with GSH when used against HIV, the thiol (—SH) moiety is capable of post translational protein modifications that may disable thermodynamically less stable viral proteins synthesized during infections. For example, Variola proteins that may be hindered include those involved in viral replication, for example, encoded viral DNA topoisomerases, and those involved in evasion of host immunologic defenses.

The four properties comprise the major clinical pharmacology of GSH as it relates to decreasing the morbidity, and possibly, the mortality of smallpox infections. The pharmacology broadens in other situations. The categorization into four properties has indistinct boundaries because they are strongly inter-related.

High normal GSH concentrations in dendritic cells, macrophages and lymphocytes rapidly up-regulate Th1 response patterns (ex. IL-12, IFNγ, and specific cell mediated immunity), required for recovery from viral infections and down-regulate Th2 response patterns (ex. IL-4, IL-10, and humoral immunity). Th1 and Th2 response patterns must be balanced, timed, and controlled. In order to minimize, or to recover from an acute viral infection, like smallpox, the host requires: IL-12, controlled IFNγ, specific cytotoxic lymphocytes, expression of inducible nitric oxide synthase (iNOS) with increased production of nitric oxide (.NO), efficient antigen processing and presentation, ample GSH concentrations in the antigen processing cells, and down regulation of Th2 response patterns. These factors are the major Th1 response patterns and are dependant on the GSH concentrations of the dendritic cells, macrophages, and lymphocytes. Since recovery from viral infection requires Th1 cytokines, tipping the balance into Th1 responses, as with ample GSH levels, would be beneficial. During a viral infection and without sufficient GSH, the reciprocal nature between Th1 and Th2 responses leads to Th2 preponderance, increased IL-4 levels and reduction in Th1 responses. The clinical consequences include prolongation of the infection, increasing severity, and potential lethality. Macrophages and the patient are at particular peril if GSH concentrations fall. For, example, in AIDS patients, the GSH deficiency in pulmonary macrophages is responsible for the unfettered growth of opportunistic microbes that are not ordinarily human pathogens, ex, *Pneumocystis carinii*. HIV/AIDS is the "model" for the catastrophic consequences of diminished GSH.

Arthropod-mediated transmission of arbovirus, e.g., Zika virus (ZIKV), dengue virus (DENV), ebola virus (EV), yellow fever virus (YFV), West Nile Virus (WNV), Japanese Encephalitis (JE), St. Louis Encephalitis virus, Omsk Hemorrhagic Fever (OMF), Kyasanur Forest Disease (KFD), Murray Valley encephalitis virus, Kunjin virus, Rocio virus, Tick-borne encephalitis, Louping ill virus, Powassan virus, etc., is initiated when a blood-feeding female injects the virus into the human skin Like many other members of the flavivirus family, ZIKV is transmitted following the bite of *Aedes* mosquitoes. Different cells types, such as epidermal keratinocytes, dendritic cells, or neurons are known to be a target of flaviviruses. Following infection with ZIKV, viral replication was observed in fibroblasts, keratinocytes and immature dendritic cells (iDCs), in a time dependent manner, with a substantial percentage of infected cells as early as 24 h post infection, whereas all cells were able to produce infectious virions. DC-SIGN, which is highly expressed on iDCs and macrophages has been known for many years to permit attachment and infection by Dengue virus thereby facilitating viral dissemination.

The TIM family is constituted of three receptors, TIM-1 TIM-3 and TIM-4. TIM-1 is expressed by Th2 cells and epithelial cells, whereas Th1 cells essentially express TIM-3. The expression of TIM-4 is restricted to antigen presenting cells. TIMs receptors have different roles, such as phosphatidylserine (PtdSer)-dependent phagocytic removal of apoptotic cells, or regulation of innate and adaptive immune responses. TIM-1 and TIM-4 expression is highly regulated following infection with DENV, WNV or YFV. The importance of TIM-1 receptor in infection was demonstrated using silencing technologies or blocking antibodies. The TAM receptor family is composed of TYRO3, AXL and MER receptors that are protein tyrosine kinases contributing to the regulation of immune responses. Whereas AXL and MER are widely expressed, TYRO3 expression is mainly observed in the central nervous system. TAM receptors have been recently described to mediate DENV, WNV and YFV entry, both in cell lines and primary human cells.

It was recently shown that DC-SIGN, TYRO3, and especially AXL, play an important role in the entry and replication of ZIKV in human skin cells. In contrast to what has been reported for DENV infection, TIM-1 and TIM-4 receptors seem to play a minor role in the entry of ZIKV in human skin cells, although a cooperative role of both TIM and TAM family members has been observed.

Following viral infection, cells mount a range of antiviral responses in order to limit the spread of the virus, with the main defense consisting of innate and adaptive immune responses. The initial response is provided for by the production of type I interferons (IFNs). Early detection of pathogen-associated molecular patterns (PAMP) expressed by the virus is sensed and mediated by pattern recognition receptors (PRRs), such as the Toll-like receptor (TLR)-family or RIG-I like receptor. Following the detection of PAMPs, the triggering of various signaling pathways not only leads to a direct secretion of IFNs, but also the expression of hundreds of Interferon-Stimulated Genes (ISGs) that integrate to induce an antiviral state of cells. DENV and WNV infections have been the subject of a large body of studies that show a pivotal role for RIG-I, MDA5 and TLR3 sensors in the host defense against these viruses, leading to IFN type 1 production and expression of ISGs. In a similar fashion, infection of human fibroblasts with ZIKV induces the expression of RIG-I, MDA-5 and TLR3, as well as the ISGs ISG15, OAS2 and MX1. Moreover, increased expression levels of IRF7, a transcription factor that binds to promoters on IFN type I genes, corroborates the strong induction of IFN-α and IFN-β by ZIKV-infected fibroblasts. Furthermore, the expression of certain inflammatory chemokines, such as CCL5, is also induced upon ZIKV infection. The inflammasome pathway seems to be activated as well following ZIKV infection, as shown by an increase in the expression of AIM2 and IL-1β transcripts.

Different cellular processes can be hijacked by flaviviruses to evade the cellular response and facilitate virus replication. Immediately following infection, the host establishes rapid innate immune responses, including IFN type I responses, the induction of apoptosis and autophagy, in order to overcome the viral infection. WNV is able to elude detection or inhibit IFN gene transcription. In addition, several arboviruses such as DENV and CHIKV can subvert the autophagy process in order to promote their own replication and dissemination. It is known that flaviviruses rearrange host cell membranes to create an appropriate environment for their replication with the main source of membranes being the endoplasmic reticulum. These rearrangements result in an activation of the unfolded protein response (UPR) and overexpress the autophagic pathway in infected cells simultaneously. The double-membrane vesicles, known as autophagosome, allow the recruitment of cytoplasmic elements, proteins and organelles and permit their degradation. Autophagy could act both positively or negatively in host immunity against pathogens. In the last mechanism, viruses use the autophagy pathway to facilitate their own replication.

The first evidences of autophagy in ZIKV-infected fibroblasts, were highlighted by the presence of characteristic autophagosome-like vesicles in infected fibroblasts. Then, the induction of autophagy in infected fibroblasts increases production of LC3, a cytosolic microtubule-associated molecule. The latter was colocalized with viral envelope protein suggesting that autophagocytic vacuoles are the site of viral replication. The use of an inhibitor of the autophagosome formation during the infection significantly reduces viral copy number while an inducer of autophagy increases viral replication, demonstrating that autophagy could play a major role in ZIKV immune evasion. Autophagy is suppressed by GSH, and this provides a significant therapeutic intervention in the viral propagation cycle. See, Hamel R, et al., "Zika virus: epidemiology, clinical features and host-virus interactions, Microbes and Infection" (2016), dx.doi.org/10.1016/j.micinf.2016.03.009.

Beyond the immediate T cell activities resulting from Th1/Th2 response patterns, the effects of IFNγ on inducing a number of additional substances is relevant in serious viral infections like smallpox, ex. (i) IFNγ fosters iNOS, and .NO production under the protection of sufficient GSH that serves to prevent, wasteful, dangerous reactions of NO with oxygen free radicals and lipid peroxides; (ii) IFNγ induces specific chemokines, Mig and Crg-2; (iii) activates cathepsin S, a potent cysteine protease; and (iv) causes the replacement of constitutive proteasomes with immunoproteasomes for efficient antigen processing and presentation. These four IFNγ dependent, and ultimately Thiols have long been recognized as important in Th1/Th2 response patterns. N-Acetyl-L-Cysteine (NAC) and GSH decreased in a dose-dependent manner human IL-4 production by stimulated peripheral blood T cells and by T helper (Th) O- and Th2-like T cell clones. This effect was associated with a decrease in IL-4 messenger RNA transcription" They found that the production of IL-4-induced Ig was also reduced by these thiols, in vitro and in vivo. GSH is a regulator of intracellular redox and other aspects of cell physiology, served as a key in the balance and extent of Th1 and Th2 cytokine response patterns. GSH concentrations in antigen-presenting cells were found to determine whether Th1 or Th2 response patterns predominate. The basic finding was GSH up-regulated Th1 and down-regulated Th2 cytokine response patterns. One of the three experimental methods employed to deplete intracellular GSH was ethanol. GSH and NAC favor a Th1 response by a preferential down-regulation of IL-4. They also found these thiols down regulated the expression of CD 30, a surface antigen belonging to the TNF receptor superfamily that is expressed by activated Th cells, and is sustained in Th2 cells. The GSH precursor, NAC, when incubated with human alveolar macrophages (AM) raised the GSH/GSSG ratio and enhanced IL-12 secretion from AM that had been previously exposed to lipopolysaccharide (LPS). Reciprocal loops were also shown since exposure of AM to IFNγ increased GSH/GSSG in AM cells. Further exposure of AM to IL-4 decreased GSH/GSSG in AM cells). NAC: (i) increased influenza virus specific lymphocyte proliferation, (ii) increased IFNγ production; and (iii) enhanced specific activity of influenza specific CD8+ CTL's (cytotoxic lymphocytes). Macrophages with a high intracellular GSH concentration could be developed by in vivo application of NAC or GSH monomethylester, and low GSH-containing macrophages by administering L-cystine derivatives, diethyl maleate or L-buthionine-[S, R]-sulfoximine. The high GSH macrophages showed elevated IL-12 and .NO production, with diminished IL-6 and IL-10 production. The low-GSH macrophages showed elevated IL-6 and IL-10 production and reduced .NO and IL-12 production. The CD4(+) CD 44(−) naïve Th O cells differentiated into Th 1 cells in the presence of high GSH macrophages, and into Th2 with low GSH macrophages. NAC down-regulated T dependent B cell activation and led to Th1 polarization, possibly by down regulating IL-4 production.

Laboratory-constructed recombinant vaccinia viruses expressing murine IL-4, alone, were previously found to be highly toxic and poorly cleared in immunocompetent mice. This IL-4 toxicity was reversed by co-expression of IL-4 with IFNγ, wherein viral clearance occurred and there were low concentrations of IL-4. This suggests that administration of high doses of GSH could overcome the increased lethality of viral engineered pox viruses enhanced with IL-4, since GSH does up-regulate Th1 cytokine production, with increased IL-12 and IFNγ, and can decrease expression of IL-4. Recombinant vaccinia virus (VV) engineered to express the gene for murine IL-4 was poorly cleared compared with control VV. Cytotoxic T-lymphocytes were greatly depressed during infection with IL-4 enhanced VV, compared to control VV infection, yet antiviral antibody levels and NK activity were not different between the two groups. IL-4 expressing VV caused suppression of: IL-12, IFNγ, and .NO production, which normally serves to clear viruses.

IL-4 effects Respiratory Syncytial Virus (RSV) epitope-specific CTL effectiveness. Infection by recombinant vaccinia virus (VV), constructed to co-express RSV M2 protein and IL4, compared to the VVM2 protein alone, led to decreased M2-specific CTL activity, demonstrating that local expression of IL-4, when antigen is presented, will decrease the cytolytic activity of primary and memory CD8 (+) RSV-specific CTL responses in vivo. Insufficient GSH at the time of viral infection will produce results equivalent to engineered viruses carrying extra copies of an IL-4 gene, as described above. Low GSH can occur as a function of age, just being over 45 years of age, alcohol, diabetes mellitus, HIV infection and exposure to environmental toxins, among others.

A few of the principal effects of IFNγ are described here since GSH up-regulates the Th1 response patterns, which result in increased IFNγ activities. In the face of antigen presentation, in an acute, dangerous viral infection, host recovery will be seriously compromised by a lapse, or decrease in Th1 response patterns, including these four IFNγ dependent functions:

IFNγ inhibits replication of ectromelia, vaccinia, and herpes simplex virus-1 (HSV-1) viruses in mouse macrophages correlated with the cells' production of NO. IFNγ induces NO synthase. IFNγ inhibits the growth of vaccinia virus (VV) in a dose-dependent manner. VV DNA synthesis was blocked and it correlated with increased generation of reactive nitrogen intermediates.

The uncontrolled induction of iNOS by IFNγ and the consequent increased production of NO can result in a greater oxidative load and cause nitrosative stress, possibly due to resistance to toxicity of glial cell cultures to high GSH levels in the microglia, and to up-regulation of MnSOD in the mitochondria in the course of the induction of i-NOS. This would relieve the total oxidative load and spare GSH.

GSH does have an important role in protecting NO physiology and antimicrobial properties by preventing spurious, wasteful and dangerous reactions of NO with oxygen free radicals and lipid peroxides. In short, GSH maximizes the normal, beneficial NO functions. GSH may also help delay or prevent ferroptosis.

An additional function of IFNγ is the induction of specific chemokines. interferon-inducible chemokines have antiviral effects against pox viruses. Monokine induced by IFNγ (Mig) and cytokine responsive gene (Crg-2) were studied in the course of vaccinia virus and ectromelia virus infections in C57 BL/6 mice. The chemokines were induced systemically. Mig and Crg-2 induced viral clearance.

IFNγ up-regulates cathepsin S, an enzyme crucial for complete processing of the MHC class II-associated invariant chain within B cells and dendritic cells. Cathepsin S is a cysteine protease and has endoproteolytic activity necessary for antigen processing.

IFNγ induces the replacement of constitutive proteasomes with immunoproteasomes, to direct these multiple proteases into efficient antigen processing, from proteins to antigenic peptides. The proteasome cleaves proteins in distinct ways to help produce antigenic peptides presented on major histocompatibility complex class I molecules. The proteasome determined the C terminus of the peptide whereas particular peptidases in the endoplasmic reticulum or cytosol determined the N terminus of extended peptides. IFNγ stimulates post-proteasomal trimming of the N terminus of an antigenic peptide by inducing leucine aminopeptidase. Thus, IFNγ not only promotes proteasomal cleavages that determine the C termini of antigenic peptides, but also can (independently of proteasomes) stimulate formation of their N termini by inducing LAP (leucine amino peptidase).

IFNγ expresses three proteasome subunits (low molecular weight proteins, LMP2 and LMP7 as well as multicatalytic endopeptidase complex-like 1, MECL-1) to form immunoproteasomes that optimize the processing of MHC class I antigens. In the models employed, they showed that the Efficient generation of a hepatitis B virus cytotoxic T lymphocyte epitope required the structural features of immunoproteasomes. During an immune response to lymphocytic chroriomeningitis virus or the bacterium *Listeria monocytogenes*, immunoproteasomes largely replaced constitutive proteasomes in the liver. GSH concentrations in pivotal cells such as monocytes/macrophages, dendritic cells, and lymphocytes are vulnerable and decline rapidly in response to alcohol, toxins, oxidative stresses, physical/emotional stress, infections, trauma, burns, and non-bacterial and bacterial sepsis. The Th1/Th2 balance shifts to Th2 predominance as a result, making recoveries difficult.

Examples of dangerous viruses, wherein GSH and shifts in Th1/Th2 have been shown to be important with regard to parameters of desirable host defenses and clearance of viruses, include vaccinia virus, recombinant VV expressing IL-4, Respiratory Syncytial Virus, ectromelia, and herpes simplex-1.

A principal property of GSH is maintenance of the Redox Potential, i.e. the Reducing vs. the Oxidizing Potential [GSH]/[GSSG]. This ratio is in the range of 500. The normal [GSH] in cells is 5-10 mM. GSH is a major determinant of the Reduction Oxidation Potential in the cell and is protectively involved in diverse cell activities, including control of cell cycle progression in human natural killer cells, and defensive responses to infections, to chemical exposures, and to other detrimental factors such as diesel exhaust particles, aging, diabetes, and photo-oxidative retinal damage. The effects of GSH concentrations on Redox and the consequent effects on specific entities such as the NFκB family, TNFα, cytokines, COX-2 and adhesion molecules, provide substance for the term, "host factors", and also provide direction for additional therapeutics, for example, raising GSH and simultaneously protecting the patient from chemical toxins and other factors detrimental to GSH.

Biochemical evolution proceeded towards a stable/controllable range of pH, $pO_2$, osmolarity, and $[Na^+]/[K^+]$; so too has this process led to a stable/controllable Redox. When the concentration of GSH is high, Redox is high. Then, it can control and slow the excess activation of the NFκB family, oxidant-sensitive transcription regulators; proinflammatory cytokines; COX-2; adhesion molecules; and TNFα and IL-1β that cause secondary cascades. A significant decrease in GSH results in a decline in Redox and activation of the NFκB family and the other factors.

The destructive effects on GSH and redox: by sulfur mustard; by the sepsis syndromes; destructive effects by diesel exhaust particles; by other infections; and other pollutants, have relevance to: the battlefield; the reconstruction of liberated countries wherein injuries, pollution and "booby" traps threaten our military and the indigenous population; and urban terrorist attacks.

Chemical toxins, including industrial toxins, undergo stoichiometric reactions with GSH. In vivo reactions with thiols may result in GSH deficiency with consequent alteration in cellular reduction-oxidation (redox) status, release of cytokines, and promotion of T helper cell 2 phenotype.

Smallpox infection may be more serious among individuals who start off being GSH insufficient and only marginally able to produce IL-12, and IFNγ, and to marshal smallpox-specific cytotoxic lymphocytes. It is possible that GSH insufficiency and predominance of Th2 phenotype represent factors in common among the seemingly disparate groups who face increased risks of complications if vaccinated vs. smallpox with the present live vaccine.

Compromised GSH concentrations and diminished redox status in humans occurs over age 45, and A precipitous decline in GSH/GSSG redox occurs, along with a linear oxidation of cysteine/cystine redox state with age at a rate of 0.16 mV/year over the entire age span (in plasma), GSH/GSSG redox was not oxidized prior to 45 years and subsequently was oxidized at a nearly linear rate of 0.7 mV/year. This amounts to four times greater oxidation of GSH after 45, compared to cysteine. GSH/GSSG ratios in peritoneal resident macrophages, in thioredoxin transgenic mice, compared with age matched wild type (WT) mice with: (i) intracellular redox status, and (ii) sustained maintenance of Th1 prevalence during aging. Their measurements of GSH/GSSG, IFNγ, IL-10 and IL-4 were expressed as IFNγ/IL-10 and IFNγ/IL-4 ratios. There was an advantageous delay in the onset of autoimmune disease among the mice with higher ratios of GSH/GSSG, IFNγ/IL-10 and IFNγ/IL-4, comparing the transgenic mice with sustained maintenance of Th1 prevalence during aging with WT mice.

In dealing with lethal, acute viral infections it is important to consider not only acquired immunity through T-cell responses, but also innate immunity via NK cells. NK responses to IL-2 are redox regulated. The IL-2-dependent cell line, NK3.3, neither incorporated [3H]-thymidine nor completed the G1-S phase transition in medium lacking the thiol-related compounds, L-cystine, and GSH, despite the presence of sufficient IL-2.

NFκB is at the epicenter of global cellular responses after viral infection. High-density oligonucleotide microarrays may be used to study the breadth of genes induced by Respiratory syncytial virus (RSV) infection that are dependent on NFκB. Cells stimulated with TNFα, to activate NFκB, as well as RSV infection, which also activates NFκB. NFκB is required for RSV-inducible expression of chemokines, transcriptional regulators, intracellular proteins regulating translation and proteolysis, and secreted proteins. Among the latter were complement components and growth factor regulators. NF-κB action induces global cellular responses after viral infection. A molecular mechanism for the pro-inflammatory effects of oxidative stress is revealed. In order for transcription factors in gene signaling networks to bind DNA, unwinding of DNA is necessary to provide access. Acetylation/deacetylation of histone residues on the histone core around which DNA is coiled is required for such access. A line of human alveolar epithelial cells, A549, was exposed to oxidative stress by $H_2O_2$ and TNFα, which led to GSH oxidation to GSSG, and depletion of GSH in the presence or absence of TSA, a substance that inhibits deacetylation of histone residues and the unwinding of DNA. The deacetylation is a reversible process and is controlled by acetyl transferases and deacetylases. TSA inhibits deacetylases and increases acetylation of histone proteins. While $H_2O_2$ and TNFα enhanced DNA binding of NFκB and AP-1, the addition of TSA potentiated the increased AP-1 and NFκB binding and also increased IL-8 release beyond the effects of $H_2O_2$ and TNFα. They concluded that the oxidant $H_2O_2$ and the proinflammatory mediator, TNF-α, induce histone acetylation which is associated with decreased GSH levels and increased AP-1 and NF-κB activation leading to enhanced proinflammatory IL-8 release in alveolar epithelial cells. This indicates a mechanism for the proinflammatory effects of oxidative stress. Oxidant stress up-regulates and antioxidants down-regulate the pleiotropic transcription factor NFκB and increased cellular GSH levels blocked NFκB activation and inhibited the release of TNF-α.

There is a role of oxidative stress as a cofactor of disease progression from asymptomatic human immunodeficiency virus (HIV) infection to the acquired immunodeficiency syndrome (AIDS). Oxidative stress is a known activator of HIV replication in vitro through the activation of NFκB, which in turn stimulates HIV gene expression. TNFα is also involved in the activation of HIV infection through similar mechanisms. TNF-mediated cytotoxicity of cells exposed to this substance is related to the generation of intracellular hydroxyl radicals. In favor of the role of oxidative stress in HIV progression is the consumption of GSH during HIV infection and progression. GSH is known to play a major role in regulation of T cell immune functions. Oxidative stress may also play an important role in the genesis of cellular DNA damage and, in this context, may be related to HIV-associated malignancies and disease progression. Oxidative stress activates the NFκB/Rel transcription factors which are involved in the activation of numerous immunoregulatory genes and the human immunodeficiency virus type 1 (HIV-1) long terminal repeat (LTR). They examined the effects of established and novel compounds including antioxidants, ribonucleotide reductase inhibitors, and iron chelators on NFκB activation and HIV LTR-mediated gene expression induced by TNF-α. N-Acetylcysteine (NAC), pyrrolidinedithiocarbamate (PDTC), and Trimidox (TD) at various concentrations inhibited TNFα-induced NFκB binding in Jurkat cells. Pretreatment of cells with these compounds prior to stimulation prevented I κB α degradation. Phosphorylation of I κB α, a prerequisite for its signal-induced degradation, was abrogated in these cells, indicating that oxidative stress is an essential step in the NFκB activation pathway. Synergistic induction of HIV-1 LTR-mediated gene expression by TNFα and the HIV-1 transactivator Tat in Jurkat cells was significantly suppressed in the presence of NAC and TD, but not PDTC.

Immunocompromised patients often have cytomegalovirus induced vascular pathology. A high thiol redox status in endothelial cells provide a barrier to CMV. A relation between viral infection and oxidative stress has been recognized for human immunodeficiency virus and herpes simplex virus-1 infections. A high endogenous thiol redox status may contribute to the apparent barrier function of endothelial cells with respect to CMV infection and that oxidative stress may facilitate CMV infection of the vascular wall.

IL-18 has the ability to strikingly augment the production of IFNγ in mature splenic dendritic cells treated with IL-12, which was ablated when GSH intracellular concentrations were decreased. This same effect of intracellular GSH deprivation was seen in macrophages.

*H. pylori* infection activates NFκB and COX-2, and that both are inhibited with GSH, NAC, and pyrrolidine dithiocarbamate, also a thiol antioxidant. Oxidant-sensitive transcription factor NFκB may play a novel role in expression of COX-2 by *H. pylori* stimulation in gastric cancer cells.

Chemokines are important for the progress of an inflammatory response by the recruitment of immuno-competent cells. Treatment of rats with the thiol antioxidant, NAC, decreased NFκB activation by lipopolysaccharide (LPS), and sufficiently diminished cytokine-induced neutrophil chemoattractant mRNA expression in lung tissue, to decrease lung lavage neutrophil count six fold. TNFα-induced macrophage (CXC) chemokines secretion is more dependent on NFκB expression than lipopolysaccharide-induced macrophage (CC) chemokines secretion.

Adhesion molecules, which are instrumental in leucocyte-vessel wall interactions, which are involved in Variola-infected mononuclear cells adhering to vessels in the dermis, preparatory to their egress into the skin, are redox regulated. Redox-regulated mechanisms of IL-4-induce monocyte chemoattractant protein-1 (MCP-1) expression in human vascular endothelial cells. NAC and pyrrolidine dithiocarbamate (PDTC). IL-4 induce MCP-1 gene expression by dramatically increasing the transcription factor, signal transducers and activators of transcription 1 (STAT1) DNA binding activity, an effect that was attenuated by PDTC. IL-4 up-regulates vascular cell adhesion molecule-1 (VCAM-1) by inducing oxidative stress. PDTC or sodium salicylate inhibited IL-4 induced expression of P-selectin, an adhesion molecule elaborated by human endothelial cells. Antioxidants have a suppressive effect on intercellular adhesion molecule-1 (ICAM-1) expression in human epidermal keratinocytes. ICAM-1 is strongly expressed by human epidermal keratinocytes during the course of inflammatory skin disease.

After Variola infected mononuclear cells adhere to the dermal vessels, their egress through the endothelial pavement and through the dermal collagen, and epidermal cells is most likely enhanced, like that of other migratory human monocyte-dendritic cells, and invasive cancer cells, by matrix metalloproteinases (MMP's). These are zinc-ion containing endopeptidases that are $Ca^{+2}$-dependent and currently constitute a family of 21 MMP's. They are countered by tissue inhibitors of metalloproteinases (TIMP).

Dendritic cells (CD's) derived from human monocytes are found to migrate through an in vitro model of extra cellular matrix, the Matrigel trans-well migration assay. Immature DC's derived with IL-4/granulocyte macrophage-colony-stimulating factor (GC-CSF), and mature DC's were induced by TNFα and modified vaccinia virus Ankra (MVA). The 'mature' DC's (induced by TNFα and MVA) showed an increased migration through Matrigel, which was significantly inhibited by inhibitors of matrix metalloproteinases (MMP). Presumably, curbing TNFα expression with GSH may inhibit MMP activities. Gene signaling leads to MMP-9 expression by inflammatory cytokines, Il-1 and TNFα. A particular protein kinase C isoform (PKC-ζ) was induced by IL-1 and TNFα, and blocking PKC-ζ activity abolished MMP-9 activity and gene expression induced by IL-1 or TNFα. These processes were shown to be NFκB dependent and were completely prevented by NFκB-binding site mutation in the MMP-9 promoter.

MMP-9 expression in vascular endothelial cells is redox sensitive, and the oxidative stress secondary to hyperglycemia provide a rationale to use antioxidants to suppress MMP-9 expression. TNFα induces oxidative stress. Pharmaceutical GSH may be beneficial in this context.

Thus, when GSH declines, redox falls, resulting in NFκB activation, acetylation of histone residues and unwinding of DNA that enhances access by NFκB and other transcriptional regulators translocated to the nucleus, followed by activation and expression of proinflammatory cytokines, chemokines, COX-2, and secondary cascades that follow the transcription regulators and the increased TNFα production.

Examples of viral infections, wherein progression of the infection and cumulative tissue toxicities are related to declines in GSH and Redox, include HIV/AIDS, and Respiratory Syncytial Virus infection.

The biochemical neutralizing reactions of GSH vs. reactive intermediates are grouped into three categories: detoxify reactive oxygen species (ROS) and reactive nitrogen species (RNS) that otherwise damage cell membrane lipids, proteins and nucleic acids and result in cellular and tissue toxicities; GSH protects mitochondria vs. $H_2O_2$, bioenergetic failure, and exaggerated, apoptotic processes that add to cumulative tissue toxicities; GSH and its companion enzymes prevent excessive, uncontrolled, tissue-disrupting-oxidations of arachidonic acid (lipid hydroperoxides, schism of peroxides, alkoxy radicals, hydroxyl radicals, isoeicosanoids and eicosanoids).

Several viral infections provide examples of the ameliorative importance of intracellular GSH concentrations, despite specific differences in the diseases, attributable to differences in viral proteins, such as Variola proteins that permit early evasion of host defenses, differences in the cells affected, replicatory processes, and host factors. The viruses eventually do encounter: (i) the human immune system; (ii) clearance mechanisms; and (iii) varying measures of inflammatory reactions. Immunologic encounters and microbial clearance mechanisms, in general, involve phagocytosis with ROS, and clearance by RNS and by apoptosis, while cytokines, such as TNFα, IL-4 and IFNγ evoke ROS and RNS, directly and indirectly, via signaling pathways; for example, IL-4 up-regulates 12/15 lipoxygenases and down-regulates GSH peroxidases to create extensive, lipid hydroperoxide-derived ROS. The continuous intracellular concentrations of GSH within: (i) the responding immune system cells; (ii) in the cells directly affected, and (iii) in by-stander cells can make a difference. The uncontrolled, combined presence of ROS, RNS, pro inflammatory cytokines, and reactive by-products of arachidonic acid "metabolism" result in "severe inflammatory response syndrome" that is found in non-bacterial sepsis states, and in serious viral infections such as smallpox, and influenza epidemics. The molecular pathologic processes are qualitatively shared.

ROS and RNS cause substantial, cumulative tissue toxicities, particularly because they initiate rapid chain reactions that yield additional, toxic by-products. The activated monocytes/macrophages, for example, actually produce both, via their 15-lipoxygenases (ROS), and the induction of iNOS (RNS) by IFNγ, generally within a similar time frame. As a result, a variety of complex interactions occur and yield reactive nitrogen species, such as peroxynitrites, that are more injurious than the initial nitric oxide.

The Human Immunodeficiency Virus (HIV) was among the early viruses studied wherein ROS, also termed "free radicals", were found to be significant factors in the infection, its molecular pathology, and progression. In symptom free HIV-seropositive individuals, significant losses of GSH are observed. Total and reduced GSH concentrations in the plasma were about 30% of those in the normal individuals (and in the lung epithelial lining fluid, ELF) about 60% of those in the controls. GSH immune deficiency may therefore contribute to the progressive immune dysfunction of HIV infection. An HIV surface glycoprotein, purified gp120, is able to induce monocyte arachidonic acid metabolites and Interleukin 1. Studies on gp120 show this occurred via a signaling pathway, and not by direct oxidation. The direct oxidation of polyunsaturates, like arachidonic acid, requires reactive oxygen species as shown in a study of the reactivity of $HO_2/O_2^-$ with unsaturated fatty acids. Free radicals are generated by the pathologic process, which then attacked polyunsaturates like arachidonate, causing chain reactions that consumed tissue antioxidants, and left a pathologic trail of cellular and tissue injuries. Lipid peroxides, or lipid peroxidation products, or losses of tissue antioxidants, such as GSH, are valid indications/biomarkers of tissue damage by uncontrolled, destructive free radical reactions now termed "oxidative stress".

An example of the disruptive effects of oxidative stress, by ozone, on macrophages and pulmonary tissues, are relevant for understanding the viral research cited in oxidative stress in support of adjunctive GSH therapy for smallpox threats and therapy. Low levels of ozone exposures of 62.5, 125 and 250 ppb of unsaturated fatty acyl groups in pulmonary surfactant phospholipids resulted in oxidative stress, as expected, and yielded a biologically active product in that it reduced elicited macrophage viability by necrosis. This damaging, oxidized phospholipid, 1-palmitoyl-2-($9^1$-oxo-nonanoyl)-glycerophosphocholine, not only decreased macrophage viability, but also induced apoptosis in pulmonary epithelial-like A549 cells as assessed by TUNEL staining, nuclear size, and caspase-3 activation with loss of viability indicated by reduction of mitochondrial dehydrogenase activity.

Oxidative stress and GSH insufficiency have been substantiated in HIV infection, along with the cumulative tissue toxicities that ensue, and the progression to AIDS. Low concentrations of acid-soluble thiol (cysteine) in the blood plasma of HIV-1-infected patients are found. The effects of GSH (GSH), GSH ester (GSE), and N-acetyl-L-cysteine (NAC) on the induction of human immunodeficiency virus (HIV) expression were investigated in the chronically infected monocytic U1 cell line, a cellular model for HIV latency. U1 cells constitutively express low levels of virus, which can be increased by phorbol 12-myristate 13 acetate (PMA), TNF-α, IL-6, and other inducers. GSH, GSE, and NAC suppressed in a dose-dependent fashion the induction of HIV expression mediated by PMA, TNF-α, or IL-6, in the absence of cytotoxic or cytostatic effects. This helps elucidate relationships between cellular GSH and HIV expression, suggest that therapy with thiols have value in the treatment of HIV infection. Attempts, however, by pharmaceutical entities to deploy thiols vs. HIV/AIDS did not meet with success because GSH at that time was not yet bioavailable.

The thiol deficiency induced by HIV is correlated with T-cell dysfunction, and therefore some have advocated treatment with N-acetylcysteine (NAC). NAC is a precursor of GSH, but requires hepatic synthesis, and may involve a metabolic burst that itself generates free radicals. GSH augments the activation of cytotoxic lymphocytes in vivo. Oxidative stress is a co-factor of disease progression. HIV-1 expression in peripheral blood mononuclear cells (PBMC) is blocked or substantially reduced by GSH. This anti-HIV-1 effect persists in these cultures for at least 35 days without evidence of significant increase in HIV-1 expression. Thus, a single pulse exposure of HIV-1-infected monocyte/macrophages with GSH led to a sustained, concentration-dependent decrease in HIV-1 p24 antigen levels, as well as, reverse transcriptase activity without producing detectable cellular toxicity in monocyte/macrophages. 8E5, a chronically HIV-infected, also has a marked reduction in GSH-peroxidase activity. HIV gene expression renders 8E5 cells 10-fold more sensitive to killing by 15-hydroperoxyeicosatetraenoic (15-HPETE), as well as several other hydroperoxy fatty acids because the low GSH-peroxidase activity in 8E5 cells prevented the conversion of the toxic 15-HPETE (15-LOOH) to the indolent 15-hydroxy-eicosatetraenoic acid 15-HETE (15-LOH) (81). Ancillary GSH enzymes provide added protection against the toxic 15-HPETE that can undergo peroxide schism [15-LOOH→15-LO.+.OH] and start free radical chain reactions via the alkoxy radical (LO.) and the hydroxyl radical (*OH). Pre-emptive conversion to 15-HETE by GSH peroxidases avoids this. The lipid-peroxidizing enzymes, like 12/15-lipoxygenases and the hydroperoxyl lipid-reducing enzymes, like GSH-peroxidase, are inversely regulated by interleukins 4 and 13. These two interleukins up-regulate the 12/15 lipoxygenases and down-regulate the phospholipid hydroxoperoxide GSH-peroxidases.

The net result is accumulation of dangerous lipid hydroperoxides (LOOH) that can start ROS pathology. This helps explain the observations in the older literature that IL-4 was a pro-oxidant that initiated free radical pathology. HIV gp120 has a complex role, and amplifies the activity of TNFα with regard to free radical generation. This in turn activates NFκB, which translocates to the nucleus and activates HIV proviral DNA by attaching to binding sites on the long terminal repeat (LTR). This results in rapid replication of HIV. The gp120 protein exerts its effects on GSH reduction through the p56 lck protein tyrosine kinase, which "transmits" a signal that increases free radical, oxidative stress.

Viral Hepatitis, particularly Hepatitis C, is characterized, in part by oxidative stress that causes significant, cumulative tissue toxicities as observed in some viral infections. In the case of HCV, ROS are generally produced secondarily, for example, via signaling pathways.

The hepatitis C virus core protein binds to the cytoplasmic domain of tumor necrosis factor (TNF) receptor 1. This leads to ROS generation, which contributes to patient morbidity, and if apoptosis follows, it may contribute to further liver necrosis and mortality. HCV core protein activates c-Jun N-Terminal Kinase through the TRADD and TRAF 2 signaling complex, resulting in oxidative stress. Oxidative stress is found in symptom-free HCV patients, and oxidative stress (without inflammation) is found in a mouse model. There is an association between ROS and HCV disease activity. There are, apparently, non inflammatory sources for oxidative stress in HCV infection including a high content of lipid hydroperoxides in HCV patients. Ferritin and hepatic GSH abnormalities occur in chronic HCV patients. Iron, particularly organic iron, is a potent catalyst for lipid peroxidation and other free radical chain reactions. Reactive oxygen and nitrogen species such as superoxide and nitric oxide are released into the extracellular spaces by inflammatory and airway epithelial cells in influenza. These molecules may exacerbate lung injury after influenza virus pneumonia. Enhanced expression of extracellular superoxide dismutase (EC SOD) in mouse airways may attenuate the pathological effects of influenza pneumonia. The pathogenic effects of a nonlethal primary infection with mouse-adapted Hong Kong influenza A/68 virus in transgenic (TG) EC SOD mice were compared to non-TG (wild-type) littermates. Compared with wild-type mice, EC SOD TG mice showed less lung injury and inflammation as measured by significant blunting of IFNγ induction, reduced cell count and total protein in bronchioalveolar lavage fluid, reduced levels of lung nitrite/nitrate nitrotyrosine, and markedly reduced lung pathology. These results demonstrate that enhancing EC SOD in the conducting and distal airways of the lung minimizes influenza-induced lung injury by both ameliorating inflammation and attenuating oxidative stress.

Nitric Oxide (.NO) is a reactive free radical, with a half-life in vivo (about 10 seconds) that is slightly longer than the more reactive free radicals, superoxide anion ($.O_2$—) and hydroxyl (.OH). .NO shares solubility characteristics with molecular oxygen and is somewhat non polar. Molecular oxygen is approximately seven times more soluble within the non polar milieu of the hydrophobic midzone of cell membranes, placing .NO and $O_2$ at the most sensitive, oxidizable areas of the fatty acyl chains of membrane phospholipids, the unsaturated bonds. Radical reactions in these non polar membrane midzones (alkoxy LO. and mobile .OH) adversely affect not only the lipids, but also the hydrophobic segments of membrane proteins. This can lead to inactivation of enzymes and alterations of other membrane macromolecular complexes. The relatively non polar structure of nitric oxide, and its slightly less reactive properties, compared to superoxide and hydroxyl free radicals, provides nitric oxide with a "range" of approximately 500 μm or more since it diffuses at 50 μm/second and has a half-life, in vivo, estimated at 10 seconds. The practical tissue and molecular pathologic consequence of this range is the effect on by-stander cells, each one averaging 15-25 μm in diameter in a tissue (lymph nodes, skin, etc.) containing activated monocyte/macrophages, that have just arrived via diapedesis, carrying smallpox or other viruses, and elaborating nitric oxide, lipid hydroperoxides, and cytokines, among other substances.

.NO reacts with $.O_2$— and forms a potent oxidant, peroxynitrite (—OONO). The disadvantages of this reaction are two-fold: (i) the desirable anti-microbial effect of NO is lost, and (ii) a spectrum of biological molecules are damaged by indiscriminate oxidations. A stable oxidation end product that is increasingly recognized as an indicator/biomarker of oxidative stress is Nitrotyrosine, now viewed as a distinctive 'molecular fingerprint' for nitric oxide-derived oxidants. NO also reacts with thiols, generally by first forming $N_2O_3$, which has more direct nitrosating properties, and readily forms S-nitrosothiols. Nitrosylation or nitrosation of proteins is a prevalent reaction that can involve additional nucleophilic side chains, in addition to SH groups, such as hydroxyls, amines and aromatic carbons. The reactivity and functional consequences of nitrosylation at a variety of nucleophilic centers in biological molecules represent another intervention accessible by GSH therapy. Nitrosation reactions are sustained at sulfur, oxygen, nitrogen and aromatic carbon centers. Thiols are the most reactive, and pre-nitrosation reduction of protein tertiary structure resulted in polynitrosylation, as more free thiols were exposed by the pre-nitrosation reduction. While some polynitrosylated proteins, like bovine serum albumin (BSA), exhibited physiologic nitric oxide properties such as vasodilator and anti-platelet activities, nitrosylation of enzymes generally had an adverse effect on enzymatic activities. Nitrosation of tyrosine residues in enzymes leads to the potential disruption to phosphorylation-dependent processes. While nitrosation of enzymes and formation of S-nitro groups at their active centers was found to be potentially reversible with thiol agents that restored activity, the nitrosation of other proteins, and in particular nitrotyrosine formation, is pathogenic. The inflammatory reactions engendered by monocytes/macrophages, although studied within atherosclerotic arteries, provide valuable information on RNS pathology for inflammation elsewhere. In many instances, the basic molecular pathologic processes are similar.

Pathology results from superoxide excesses arising from leucocyte-derived NAD(P)H oxidase complexes, and the simultaneous consumption of nitric oxide by leucocyte-derived myeloperoxidase. The net result is compromised NO physiologic effects by this simultaneous, dual action of: (i) removing NO by the formation of peroxynitrite, and (ii) the consumption of NO by myeloperoxidase activity. This same "mix" of activated leucocytes, with their NAD(P)H oxidase complexes, and myeloperoxidase, plus activated monocytes/macrophages elaborating nitric oxide, is found at sites of inflammation and infection, as in smallpox lesions. The formation of Nitrotyrosine has important implications for the inhibition of pox virus DNA topoisomerase discussed and referenced, further on, under the fourth property of GSH. In addition to GSH affecting the thiol reactions of these topoisomerase SH enzymes, there is a critical Tyrosine-274 residue in vaccinia topoisomerase, which forms a 3'-phosphodiester bond with the DNA backbone. If NO attacks it (targeting protein hydroxyls (OH), SH, and other moieties), then the resulting nitrotyrosine could effectively convert the topoisomerase into an endonuclease forming a 60 bp duplex DNA with a 3'-phosphate terminated product. This potential, to create a crippling nitrotyrosine within a critical site in a pox virus DNA topoisomerase, may be practical as discussed under property number four, particularly if ample GSH is present to prevent wasteful, and harmful formation of peroxynitrites that prevent the useful functions of nitric oxide. One of the hypotheses described further on considers that GSH can reduce functional disulfide formation and reduce inter- and intra-chain disulfides in topoisomerase, thereby making cysteines and the Tyr-274 accessible to nitrosating reactions. Nitrosation of proteins involves nucleophilic side chains such as SH and OH. Nitrosations and glutathionylations can be selective versus pox virus topoisomerases, because it is the monocyte/macrophages/dendritic cell population that harbors much of the viral load, and it is this cell population that generates significant quantities of nitric oxide. In the presence of sufficient GSH, ROS and RNS can be curtailed to permit orderly formation of S-nitrosoGSH, a long lasting, diffusible NO donor that would be available and in close, intracellular proximity to the NO-sensitive hydroxyl of Tyr-274 of pox virus DNA topoisomerase. Further details are provided under property number 4 of GSH.

IL-4 enhancement of vaccinia virus is suppressed the IFNγ-NO-mediated clearance of virus. Diminishing the morbidity and mortality of smallpox infections requires the enhancement and preservation of the anti-viral, microbial clearance properties of nitric oxide, but without the RNS-mediated pathology. Ample, consistent concentrations of intracellular GSH do provide the balance, potency, and safety required to prevent excessive ROS/RNS reactions that otherwise deplete GSH, and then lead to perpetually worsening tissue toxicities. The viability of these macrophages is diminished, under their experimental conditions, by exposure to an NO-releasing compound, S-nitroso-N-acetyl penicillamine (SNAP). When the GSH concentration was experimentally reduced in these macrophages, cell viability was decreased further. However, the macrophages were protected when the thiol, NAC, was used as a pretreatment.

Increasing GSH levels attenuates the decline in myocyte CK (Creatine Kinase) activity following exposure to the NO donor, S-nitroso-N-acetylcysteine (SNAC). On the other hand, when GSH levels in the myocytes were decreased, the S-nitrosation of creatine kinase by SNAC was enhanced and enzyme activity diminished. Peroxynitrite has cytotoxic effects in human venous endothelial cells and in rat aortic smooth muscle cells. GSH attenuates the peroxynitrite induced suppression of mitochondrial respiration formation of nitrotyrosine protein oxidation DNA single strand breakage and activation of the nuclear enzyme poly (ADP-ribose) synthase. When GSH concentrations were lowered experimentally, the peroxynitrite-induced cell toxicities worsened. The synergistic toxicity of NO and ROS occurs by forming peroxynitrite and other cytotoxic agents was amenable to inhibition by antioxidant enzymes.

Insulin-producing RINm5F cells were bioengineered against cytokine-mediated toxicity. Catalase, GSH Peroxidase and Cu/Zn SOD were protective, apparently because of an inactivation of ROS generated in the signal cascades of the cytokines used in the experiments. GSH is effective in preventing peroxynitrite formation from NO and $.O_2^-$, generated simultaneously in microglia via iNOS, and NADPH-oxidase, respectively. Peroxynitrite formation in continuously nitric oxide-producing microglial cells is rather limited. However, activation of the superoxide-generating enzyme, NADPH-oxidase, dramatically increased (peroxynitrite) within a few minutes. Superoxide is therefore the limiting factor for peroxynitrite formation. GSH, but not ascorbate, significantly decreased peroxynitrite formation.

The thiol redox state controls membrane transport systems in mitochondria. The three major redox-active factors within mitochondria, are the electron transporters of the reparatory chain, protein thiols, and matrix GSH. These are inter-related by the availability of NADPH, a co factor for GSH reductase, which is essential for the maintenance of the redox state of intra mitochondrial GSH. Free SH groups, as in reduced GSH, are essential for the activity of all metabolite carriers in the inner mitochondrial membrane, otherwise, extensive thiol oxidation results in: the inhibition of transport activity, and the dissipation of the mitochondrial inner transmembrane potential ($\Delta\psi[m]$), an early, potentially reversible event observed in mitochondrial related apoptotic processes, bioenergetic failure, also an early event that is part of the dissipation of $\Delta\psi[m]$, and an increase in the permeability of the mitochondrial membrane, a later event in mitochondrial related apoptotic processes.

Mitochondrial GSH concentrations are higher than those in the cytosol, 10 mM compared to 7 mM, respectively. Since mitochondria cannot synthesize GSH, for lack of the two enzymes (gamma glutamylcysteine synthase and glutathione synthase), it is transported against a concentration gradient into the mitochondrial matrix by a high-affinity component (Km, approximately 60 μM; V max, approximately 0.5 nM/min per mg of protein) stimulated by ATP and a lower affinity component. The need for GSH in mitochondria is its catalytic activity, to reduce $H_2O_2$ produced by MnSOD acting on superoxide anion. Since there is no catalase produced in, or transported into mitochondria, mitochondrial GSH is indispensable. In the cytosol of all cells, plasma, and red blood cells, superoxide dismutase (in the form of CuZn SOD) functions in concert with catalase to prevent accumulations of $H_2O_2$. Without catalase, or the catalytic activity of GSH, $H_2O_2$ would accumulate, eventually producing highly injurious hydroxyl radicals (.OH). The consequences can lead to bioenergetic failure of strategic cells and to exaggerated, apoptotic processes. GSH depletion is related to bioenergetic failure, with the later development of apoptotic processes. GSH depletion will lower a cell's capacity to buffer against endogenous oxidants, and it may set a time limit on continued mitochondrial function and thus indirectly on total ATP levels and membrane integrity.

Thymocytes exhibit disruption of the mitochondrial $\Delta\psi[m]$, and a depletion of non-oxidized GSH that was near-to-simultaneous. They felt this represented a first step in a two-step apoptotic process. The loss of $\Delta\psi[m]$ represents bioenergetic failure with diminished ATP synthesis. This state can progress to later apoptotic processes as step 2. Apoptotic processes sometimes benefit the patient, as in the eradication of cancer cells, and perhaps microbe-laden cells, provided the microbes in the cell fragments that are phagocytosed by non-infected cells are not infectious or are rapidly rendered so. Apoptotic processes in vaccinia virus-infected macrophages (murine line J774.G8), include changes of mitochondrial membrane potential. Vaccinia virus (VV) infection shows early gene expression which seemed to be required for induction of apoptosis, while late gene expression was not. Induction of apoptosis by VV in macrophages induces a decrease in mitochondrial membrane potential and is associated with altered levels of Bcl-x (L) an anti-apoptotic member of the Bcl-2 family. Although monkey pox is not readily transmitted among humans it, along with variola, vaccinia and cow pox cause cutaneous lesions that share similarities. The lower airway epithelium served as the principal target, but the involvement of lymphoid tissues in the tonsils, and mandibular nodes suggested these lymphoid tissues were infected early. The pathology indicated widespread lymphatic dissemination of the virus through a monocytic cell-associated viremia and the mononuclear phagocyte dendritic cell system was the principal target within lymphoid tissues and may also have provided the means of entry into other systemic sites. Lesions of monkey pox infection. All sites were necrotizing. Terminal deoxynucleotidyl transferase mediated deoxyuridine triphosphate nick-end labeling (TUNEL) staining of select lesions suggested that cell death within lymphoid and epithelial tissues was due in large part to apoptosis. Based on pathologic, and virologic similarities (monkey pox, vaccinia, cow pox, and variola are members of the genus orthopox virus, and can infect humans and cause cutaneous lesions), it would seem that smallpox lesions also develop, in part, by apoptotic processes.

The molecular pathologic processes believed to occur in smallpox take a toll on GSH concentrations: (a) induction of iNOS with increased NO production, (b) the generation of superoxide, (c) formation of peroxynitrite, (d) GSH-consuming chain reactions of ROS and RNS, (e) TNFα related oxidative stress, the induction of Cox-2 with increased oxidation of arachidonic acid, (g) oxidative bursts from macrophages engaged in phagocytosis at sites of infection and inflammation, and related cascades. With losses of intracellular GSH, the types of apoptotic processes induced in smallpox infections would include those driven by GSH losses and diminished redox in mitochondria and cytosol. Penninger summarized the role of mitochondria, including the $\Delta\psi[m]$, the mitochondrial permeability transition pores (PT), the disruption of outer mitochondrial membrane integrity leading to the release of cytochrome c and apoptosis inducing factors, and the temporal aspects of several modifying factors which included GSH.

A significant amount of pro-caspase-3 is found in mitochondria. Jurkat cell studies indicate the pro-caspase-3 is in a pre-apoptotic complex, within mitochondria with "chaperone" proteins. In other apoptosis studies, wherein GSH was depleted with buthionine sulfoximine, the Bcl-2 protein, which is crucial in preventing, or slowing apoptosis, was degraded. The beneficial effect of adding GSH to cells in this study was not a direct effect of GSH but possibly a prevention of the degradation of Bcl-2 protein. When Fas triggers apoptosis in human activated neutrophils, inhibition of the subsequent apoptotic processes may be achieved by increasing the intracellular GSH levels with exogenous GSH. Fas induced signaling for neutrophil apoptosis can be inhibited in a redox sensitive manner.

Monovalent thiol-reactive compounds inhibit apoptosis induced by their model systems in thymocytes, and further, the critical thiols are likely to be located in the mitochondrial matrix. Hypergeneration of superoxide anion, oxidation of compounds of the inner mitochondrial membrane, depletion of non-oxidized GSH were are to various apoptotic models. The presence of GSH transporters on plasma membranes and on mitochondria has been well delineated and these provide the molecular/cellular means to assure intracellular and intra mitochondrial distribution of administered GSH.

GSH, via GSH peroxidases and GSH S-transferases, helps control oxidations of arachidonate, thereby decreasing lipid hydroperoxides, isoeicosanoids and eicosanoids that can be overly proinflammatory and disadvantageously apoptogenic and immunosuppressive. Regarding terminology, eicosanoids include prostaglandins, thromboxanes, leukotrienes and lipoxins formed by enzymes, whereas isoeicosanoids are non-enzymatically formed isomers driven by free radical reactions. The GSH peroxidases and S-transferases are protective and normally disassemble lipid hydroperoxides before they can expand cell injury. But, they require GSH which may become compromised by oxidative stress induced by several factors in the course of serious infections, such as oxidative bursts by activated macrophages, hypergeneration of superoxide, TNFα-generated oxidative stress, induction of Cox-2 with increased arachidonate oxidations, and induction of iNOS with increased formation of nitric oxides and nitrosated GSH.

The C-2 of the glycerol backbone of phosphoglycerides is generally esterified to a polyunsaturated fatty acyl chain such as arachidonate, and the C-2 ester may be acted on by phospholipase $A_2$ ($PLA_2$) thereby releasing free arachidonate. These polyunsaturates are highly subject to peroxidation, either spontaneously or enzymatically by cyclooxygenases and lipoxygenases, because their unsaturated (double bonded) carbons are un conjugated, i.e., separated by an interposed, singly bonded carbon, classified as alpha methylenic because its C—H bonds are activated due to the distribution of bonding electrons over a "spread" of four to five carbons. Abstraction of a hydrogen from the α-methylenic carbon therefore occurs readily by molecular oxygen radicals, leaving a carbon radical that is instantly attacked by other activated species, with the final product generally being a hydroperoxide (—OOH) attached to the carbon (LOOH). These lipid peroxides are unstable and undergo schism, producing an alkoxy and a hydroxyl radical that can attack other alpha methylenic carbons [LOOH→LO.+.OH]. Peroxidation of arachidonate and other polyunsaturates can occur within membranes, and micelles, and their schism products can initiate cytotoxic chain reactions that alter membrane structure and also attack membrane proteins, and membrane associated DNA. There are a number of controls that protect cells from rampant lipid peroxidation, including inherent membrane structure, normally low levels of $PLA_2$ activity, lipophilic antioxidants, and enzymes that disassemble LOOH's before they can undergo schism, such as the GSH peroxidases, and GSH S-transferases.

VV that have been bioengineered to express IL-4. In one case, recombinant VV expressing a Respiratory Syncytial Virus epitope (M2), either alone or in combination with IL-4 (vv M2/IL-4) become more difficult to clear, fail profoundly to elicit antiviral cytotoxic lymphocyte responses, and kill the infected laboratory animal more rapidly. These disadvantageous effects of over-expressed IL-4 in acute viral infections can occur without bioengineering. Insufficient intracellular GSH concentrations resulting from aging, diabetes, prior exposures to chemical toxins, or during the course of serious infections, will skew immune response patterns to Th2 pathways and result in disadvantageous up-regulation and increased expression of IL-4. Among the IL-4 disadvantages during an acute viral infection, is the up-regulation of the cyclooxygenases (COX-2), and the lipoxygenases (5-, 12-, 15-), resulting in excess formation of lipid hydroperoxides (LOOH's) and the simultaneous down-regulation of the protective enzymes that disassemble LOOH's (GSH peroxidases and GSH S-transferases). Human peripheral monocytes studies of this inverse regulation by IL-4, show these regulatory processes also occur in vivo. Arachidonic acid oxygenase and phospholipid hydroperoxide GSH peroxidase activity were assayed in various tissues of transgenic mice that systemically overexpress IL-4. In lung, spleen, kidney and heart, an increased arachidonic acid oxygenase activity was detected when transgenic mice were compared with inbred controls. The phospholipid hydroperoxide GSH peroxidase activity was impaired in lung, liver, and spleen of the transgenic animals. 15-HPETE, derived from 15-lipoxygenase activity, and several other hydroperoxy fatty acids are lethal to a T cell line that is chronically HIV infected (8E5) because of a marked reduction in GSH peroxidase activity inherent in the 8E5 T cell line. IL-4, therefore, when overexpressed by viral engineering, or insufficient GSH concentrations that skew T helper response patterns to Th2, can result in lethal accumulations of hydroperoxyls by up-regulating 12- and 15-lipoxygenases to produce increased quantities of 12- and 15-HPETE's.

These cannot be reduced to the less toxic 12- and 15-HETE's because the relevant GSH peroxidases have been down-regulated by IL-4. In addition, in the course of acute inflammation and NFκB activation, Cox-2 is induced. Induction of Cox-2 could be inhibited, in their model systems, by GSH, N-acetyl cysteine, and pyrrolidine dithiocarbamate (PDTC).

GSH therapy that effectively replenishes and maintains intracellular concentrations should be able to down regulate IL-4 produced as a result of overly favored Th2 response patterns, and also correct the GSH insufficiencies that may lead to Th2 cytokines in people over 45, in diabetics, in the chemically exposed, and in those with serious, overwhelming infections. The results of GSH therapy could include down regulation of 12- and 15-lipoxygenases, up-regulation of GSH peroxidases, and down regulation of the NFκB cascades that include the induction of Cox-2. These favorable biochemical results would help lead to the prevention and reduction of cyto- and tissue toxicities associated with smallpox infections.

Th2 cytokines pose an additional disadvantage during an overwhelming infection in fostering expression of a group of phospholipase A2's (PLA 2) that are preferentially expressed in Th2 cells. PLA2's release arachidonate by carrying out interfacial catalytic activity at the interface of the aqueous phases on either side of a cell membrane, and the condensed lipid phase that is the membrane. PLA2 enzymes are structurally diverse in mammalian cells and are responsive to different conditions. One group of PLA2's was found to be inducible by cytokines such as IL-1, TNFα and IL-6 and to be suppressed by anti-inflammatory glucocorticoids. A new group of PLA2's (group XII, specifically, GXII-2 PLA2) were identified that selectively expressed in murine Th2 clones and in vitro differentiated mouse CD4 Th2 cells as compared with Th1 clones and cells. Anti-CD3 stimulation up-regulated GXII PLA2's in Th2 cells compared to Th1 cells. This novel PLA2 group would enhance the responsiveness of Th2 cells through release of immediate second signals and generation of downstream eicosanoids. If Th2 response patterns are up-regulated during a serious infection because GSH concentrations have been eroded by a multiplicity of factors, as described previously, the enhanced catalytic activity of a specific PLA2 in Th2 will speed the cumulative cyto- and tissue toxicities.

Finally, lipid hydroperoxides (LOOH's) that are not reduced to their corresponding LOH's generate toxic, apoptogenic products, including 4-hydroxy nonenal (HNE). The LOOH product, HNE, induced significant tissue injury and apoptosis. GSH, in a particular experimental model of monocyte-macrophages, protected against macrophage death by conjugation of HNE, thereby rendering it nontoxic, the last example of this property of GSH of neutralizing reactive intermediates that otherwise cause cellular and tissue toxicities. GSH can prevent and reduce cyto- and tissue toxicities produced by multiple pathways which, although different, share a capacity for amelioration by GSH by virtue of the carefully positioned thiol of GSH with a zwitterion from the gamma glutamyl residue.

As occurs with GSH vs. HIV, the thiol moiety of GSH is capable of safe, post translational protein modifications that may disable thermodynamically less stable viral proteins synthesized during infections. Variola proteins that may be hindered include those involved in viral replication, specifically, encoded viral DNA topoisomerases, and evasion of host immunologic defenses.

Cysteine residues and amino acid sequences are among the major factors determining the folded conformation of proteins for structural and functional utility. Considerable "effort" is expended by the normal cell as it forms disulfides for intramolecular and interchain bonds that have the requisite thermodynamic stability for the particular protein. Some protein disulfides must be readily accessible in order to undergo the redox changes that allow for regulation of enzymes, orderly signaling and responsive receptors. Still other proteins are designed for rapid turnover and must be easily unfolded and dismantled in preparation for replacement.

The folding of normal host proteins is guided by complex, controlled interactions that stabilize the final folded state. A number of factors, in addition to the amino acid sequence, affect folding, including [H+] and enzymes such as protein disulfide isomerase (PDI), peptidyl propyl isomerases (PPIases), and molecular chaperones. PDI accelerates disulfide interchange in kinetically trapped intermediates, shuffling these disulfides until the most stable protein configuration is achieved. PDI speeds this shuffling by several thousand fold. PPIases speed cis to trans isomerization since the peptide bonds are almost always in the trans configuration. Molecular chaperones inhibit improper intermolecular interactions of protein intermediates, literally consuming ATP to untangle trapped intermediates. These steps are necessary for protein stability, and require considerable energy resources along with PDI's, PPI's, and molecular chaperones.

Heat Shock Protein (HSP33 is a very potent molecular chaperone, which is itself dependent on disulfide bonds. Hsp 33 has six cysteinyl residues. When these are in their chemically reduced form, Hsp33 is inactive and displays no folding helper activity. However, under oxidizing circumstances, such as hydrogen peroxide, Hsp 33 becomes active and resumes its functions in untangling trapped protein/polypeptide intermediates within the easily clogged protein-folding subcellular compartment of the endoplasmic reticulum. Mass spectrometry (matrix-assisted laser desorption/ionization MS, MALDI-MS) demonstrated that Hsp 33 activation by $H_2O_2$ was accompanied by the formation of two intramolecular disulfide bonds with Hsp33: Cys (232)-S—S Cys (234) and Cys (265)-S—S (268). Accessibility of the cysteinyl residues was also emphasized. For example, Cys (239), one of the six cysteinyl residues, is poorly accessible when Hsp 33 is active, and remains reduced despite $H_2O_2$ exposure, and does not therefore react with the sixth cysteinyl, Cys (141), which is highly reactive toward chemical modifications, demonstrating that other factors such as amino acid sequence, and other amino acid/peptidyl properties also are important in protein folding.

In non-malignant, non-infected eukaryotic cells, considerable ATP-consuming "quality control" goes into disulfides. Pox virus protein synthesis, by contrast, proceeds within cytoplasmic enclaves inside infected cells, and does not have the benefits of orderly testing of the thermodynamic stability of their protein disulfides, nor is there a reliable, sufficient supply of ATP to support the ongoing synthesis of the three groups of "testing" proteins (protein disulfide isomerases, peptidyl prolyl isomerases and molecular chaperones). This provides a basis for the post translational selectivity of GSH in safely reducing and/or glutathionylating the critical protein thiols of Variola, without cytotoxicity, particularly DNA topoisomerase and the evasion proteins.

The redox environment within some viral infected host cells, such as mononuclear cells/macrophages, is generally low, secondary to the over-utilization of GSH in curbing reactive intermediates generated by: TNFα; NADPH oxidase; the alkoxy and hydroxyl free radicals resulting from the homolytic schism of lipid hydroperoxides (LOOH's→LO.+.OH) produced in excess by the induced COX-2; and by the Reactive Nitrogen Species (RNS) that accompany iNOS induction. Low GSH concentrations in HIV and other infections foster an oxidative environment conducive to disulfide formation and extensive protein folding in the viral proteins synthesized within the infected mononuclear cells/macrophages. HIV replication rates are rapid when GSH redox decreases, triggering the redox-sensitive activation of NFκB, which in turn activates nuclear-integrated HIV proviral DNA through NFκB binding sites on the long terminal repeat (LTR). The HIV proteins would be expected to have their cysteinyl residues bound as disulfides in this oxidative environment.

An encoded HIV TAT protein that specifically activates transcription from the viral long terminal repeat was studied, whose activity is dramatically inhibited by the preincubation of the protein with strongly reducing agents. These results suggest that the cysteine residues of TAT are involved in the formation of intramolecular disulfide bonds. Exogenous GSH strongly suppresses virus infectivity budding and release of virus particles from chronically infected cells (either macrophages or lymphocytes), together with a selective decrease in the expression of gp120, the major envelope glycoprotein, rich in intra chain disulfide bonds, and thus potentially sensitive to the effect of a reducing agent such as GSH. GSH can interfere with late stages of virus replication, similar to cells exposed to herpes virus type 1 (a DNA virus) or to Sendai (an RNA virus), showing that the suppression of virus replication by GSH is related to the selective inhibition of envelope glycoproteins.

Intracellular GSH content has an effect on HIV replication in human macrophages. In vitro HIV-1 infection induces a significant decrease in intracellular reduced GSH in human macrophages. Such a decrease was observed at the time of infection corresponding to maximum release of virus from infected cells and was not related to cell cytotoxicity. Treatment of macrophages with BSO (buthionine sulfoximine) significantly increased the HIV yield in the supernatant. Exogenous GSH strongly suppressed the production of p24 gag protein as well as the virus infectivity. GSH antiviral effect occurred at late stages of virus replication and was related to the selective decrease of specific glycoproteins, such as gp120, which are particularly rich in disulfide bonds. In addition to the disulfide involvement in HIV TAT protein, and gp120.

The two conserved cysteines of the HIV-1 protease may be involved in regulating protease activity. Diglutathionylated wild type protease (Cys-67-SSG, Cys-95-SSG) and the monogluthionylated protease mutants (C67A, Cys-95-SSG and C95A, Cys-67-SSG) are potential substrates for thioltransferase (glutaredoxin). At low thioltransferase concentrations (5 nM), deglutathionylation occurred almost exclusively at Cys-95-SSG. With substantially more thioltransferase (100 nM) Cys-67-SSG was partially deglutathionylated but only at 20% of the rate of Cys-95-SSG reduction. Treatment of the diglutathionylated protease with thioltransferase not only restored protease activity but generated an enzyme preparation that had a 3- to 5-fold greater specific activity relative to the fully reduced form. The results implicate thioltransferase in the regulation and/or maintenance.

Gp120 protein of HIV not only serves as the means of attachment of the virus to CD4+ receptors, it also amplifies the activity of a toxic cytokine, TNFα (causes free radical reactions and also weight loss). TNFα also activates NFκB, which in turn stimulates HIV replication. Hence, gp120 protein potentiates TNFα, which activates NFκB, and increases HIV replication. The gp120 protein alters the redox state of cells, and increases $H_2O_2$ production, ensuring disulfide formation in proteins. This activity of gp120 causes a reduction of GSH and an increase in oxidized GSSG. The gp120 protein exerts these effects through the p56 lck protein tyrosine kinase, which transmits a signal that increases free radical oxidative stress. In these HIV studies, wherein critical HIV disulfides were biochemically reduced, to the detriment of HIV, there were no findings apparently of cytotoxicity. In other HIV studies, where exogenous GSH was added, and viral inhibition was evident, specific observations were made regarding the sustained anti HIV effects of GSH for 35 days, in vitro, without producing detectable cellular toxicity in monocytes/macrophages.

Topoisomerases are SH proteins that nick one or both strands of supercoiled, double stranded DNA for processes that require separating the strands, for example, transcription, recombination and replication. This is accomplished by cleaving the DNA, one or both strands; and religation of the DNA break(s). There are many topoisomerases, and James Wang, one of the discoverers of these enzymes, has described them further. The two major categories, among others, are Type I topoisomerases that cleave only one strand, and Type II, which cleave both strands. After Type II topoisomerases cleave the DNA (requires ATP), the 5'-phosphate terminus of each cleaved DNA strand remains attached to the enzyme by linking to a specific tyrosine residue at the active site. The two ends of the cleaved DNA, therefore, remain "anchored" to the topoisomerase. Otherwise, the two cleaved ends will rotate freely and massively disturb the topology and functions of the DNA. Topoisomerases have been successfully targeted for antibiotics vs. bacteria, and chemotherapeutic agents vs. cancer. With regard to antibiotic use, DNA gyrase (150) in prokaryotes is more sensitive than the one in eukaryotes. The quinolone antibiotics are powerful pharmaceuticals and specifically inhibit topoisomerase II (DNA gyrase) and topoisomerase IV. The concept of differential sensitivities of topoisomerases to inhibitors in viruses, compared to human cells is relevant. A particular vulnerability of all topoisomerases is their complex mechanisms of action in modifying the topology of DNA by generating transient double-strand breaks. The dual function of Topoisomerases, i.e., catalysis and religation, requires unimpeded reactivities of the cysteinyl residues that bind and affect the inter-subunit interactions of topoisomerase to achieve "global" effects.

These cysteinyl residues are accessible and have been targeted. Quinoid inhibitors are described below. In addition to the reactivity and accessibility of these protein thiols, the active site Tyr-274 can serve as a target for nitric oxide which is generated by the viral-laden, activated macrophages. The formation of Nitrotyrosine, within the infected, nitric oxide-generating macrophages, may be enhanced by GSH actions: (a) reducing the protein disulfides, and/or glutathionylating the free protein thiols allows for some unfolding, as intramolecular and interchain disulfides are reduced and/or glutathionylated; the subunits of topoisomerases rely, in part on inter chain disulfides for their dual actions of catalysis and religation; and (b) preventing peroxynitrite formation and thereby maintaining nitric oxide availability for nitrosation of Tyr-274; NitrosoGSH forms spontaneously and serves as an "orderly" nitric oxide donor.

Replacement of the active site tyrosine of vaccinia DNA topoisomerase converts the enzyme into a site-specific endonuclease. Normally, Tyr-274 of this enzyme links to a specific phosphate in the DNA via a 3[1]-phosphodiester bond VV topoisomerase forms a covalent protein-DNA intermediate at recognition sites in duplex DNA. The nucleotide is linked via a 3'-phosphodiester bond to Tyr-274 of the enzyme. Substitutions of Tyr-274 by glutamate, cysteine or histidine remain enzymatically active insofar as cleaving the duplex DNA, but religation does not occur since the 3'-phosphodiester bond doesn't form, it requires the OH of Tyr-274. The product of the mutant substitutions is an endonucleolytically cleaved 60 bp duplex DNA at the recognition site with a 3'-phosphate termination. With biochemical reduction of the viral protein cysteinyl residues, or their glutathionylation, the active site tyrosine, Try-274, may become exposed and available for nitrosating reactions, to form Nitrotyrosine. GSH decreases aberrant reactions of Reactive Nitrogen Species (RNS), and protects Nitric Oxide so that peroxynitrite is less likely to form, and more is available for antiviral protein nitrosation.

Since the virus is within infected, activated mononuclear cells/macrophages, which now generate increased Nitric Oxide, secondary to the induction of iNOS, there would be a measure of selectivity in forming Nitrotyrosine in viral topoisomerase within these cells and thereby safely inhibit the enzyme.

Thiol alkylation of topoisomerase II by a variety of thiol-reactive compounds, including quinones that react with thiols, and three other potent, thiol-reactive agents: N-ethyl maleimide (NEM); disulfiram; and an organic disulfide [2,2'-dithiobis (5-nitropyridine)] can interrupt "global" activity. All of these caused topoisomerase II-mediated DNA cleavage. The topoisomerase acted as an endonuclease. These agents in fact reacted adversely with cysteinyl residues in topoisomerase by using mutant yeast TOP2 with all cysteine residues replaced with alanine (cysteineless TOP2). This replacement completely abolished the TOP2-mediated DNA cleavage induced by thiol-reactive quinones. The topoisomerase cysteinyl residues, in some cases, are accessible to thiolating substances, e.g. GSH, that can glutathionylate accessible cysteines, as shown in the prior subsection on HIV. The thiol residues on the topoisomerase II-DNA complex were exposed and were alkylated by naphthoquinones, thereby providing a biomimetic model of topoisomerase II poisoning by quinones. Topoisomerase II is a model system of a SH-containing enzyme to determine the reactivities of the quinone metabolites of chlorinated biphenyls (environmental contaminants). Binding of these quinones to GSH paralleled their binding to protein SH groups in topoisomerase II, and this is a possible mechanism for the observed DNA strand breaks generated by PCB metabolism. Topoisomerase cysteinyl residues may be accessible and susceptible to exogenous GSH, with perhaps greater vulnerability by viral topoisomerases, analogous to some bacterial topoisomerase inhibitors, like quinolone antibiotics vs. the topoisomerase II (DNA gyrase) of a number of bacteria.

The formation of intramolecular and interchain disulfide bonds, to fold proteins into their optimum configurations, proceeds under normal circumstances through "quality control" testing, as previously described PDI's, PPIases, molecular chaperones, abundant ATP for the chaperones and for the syntheses of these "quality control" proteins. By contrast, viral proteins, ex HIV Tat, gp120, and protease, are generally produced under less than optimum circumstances because the intracellular environment of a viral infected cell, that is activated and responding, is chaotic, with compromised bioenergetics and host responses that include nitric oxide from NFκB induced iNOS. The NO, unless diverted to form peroxynitrite, is available to form adducts with tyrosyl residues and cysteinyl residues that are relatively more exposed when the viral proteins are forming as nascent polypeptide chains. The potential to form Nitrotyrosine and Nitrosothiols in these nascent chains, within activated, infected mononuclear cells/macrophages may be significant. However, the pathologically successful pox viruses, such as smallpox, encode proteins that allow the viruses to evade host immunologic responses. These evasion proteins, as described more fully below, correlate with virulence. They interact, directly and indirectly, with host defense factors to nullify them: NFκB, TNFα, IFNγ, IL-18, most of the components of the proinflammatory cytokine cascades, complement, chemokines, and inhibitors of dendritic cells, and thereby negate innate immunity via NK cells, and acquired immunity through T cells. The result in the lethal pox virus infections is early, "silent", unimpeded viral replication, and spread. When host cells do begin to react by inflammatory responses, around 10 days post variola exposure, defense factors are overwhelmed by the large numbers of virions. The patient is now prostrate, with hyperpyrexia, and facing death.

An erosion of intracellular GSH, which is most severe in the responding mononuclear cells-macrophages and T cells, shifts the Th0 cells into Th2 response patterns that include increased IL-4 production, with suppression of: IL-12, IFNγ, and specific anti-Variola cytolytic cells, the opposite of what is required to have a chance at recovery. Based on the properties of GSH, the nature of preferred GSH formulation, and the ubiquitous presence of GSH transporters, the following reactions should occur with GSH administration: Accessible cysteinyl residues in pox proteins (for virion structure, for viral replication, and for evasion) will be reduced, if present as thermodynamically inadequate disulfides; and exposed cysteinyl residues, particularly on the nascent Variola polypeptide chains, can be glutathionylated through formation of mixed disulfide bonds.

The genomes of poxviruses encode many proteins which interact with host processes at both cellular and systemic levels some of which blocked the development of a chemotactic substance, or interfered with the activation of the classical complement pathway. A 38-kDa protein of cowpox virus inhibits the generation of chemotactic molecules which are elicited during virus replication.

Various examples of evasion proteins vs. host responses: oppose apoptosis, capture chemokines, counteract complement, interfere with interferon, and intercept interleukins. The following represent a sampling of the range of evasion proteins encoded by pox viruses and produced by infected cells: IL-18 binding proteins by ectromelia, vaccinia and cow pox; TNF receptors by cowpox, ectromelia, and camelpox, CC-chemokine inhibitor by vaccinia virus 35-kDa protein (VV-35 kDa); NFκB inhibition by cowpox virus; Complement regulatory protein by vaccinia virus, inactivates human C3b and C6; CD 30 homologue by ectromelia, induces reverse signaling in cells, blocks the generation of interferon gamma-producing cells, and strongly inhibits Th1 responses, but not Th2.

High GSH levels have been demonstrated to be necessary for proper functioning of platelets, vascular endothelial cells, macrophages, cytotoxic T-lymphocytes, and other immune system components. Recently it has been discovered that HIV-infected patients exhibit low GSH levels in plasma, in other fluids, and in certain cell types like macrophages, which does not appear to be due to defects in GSH synthesis.

Smallpox

Smallpox is categorized a Class A Bioterror Agent along with *Bacillus anthracis, Yersinia pestis, Francisella tularensis,* Botulinum toxin, and the Filo and arenaviruses such as Ebola and the Hemorrhagic fevers. Experts believe that only a few virions are necessary for transmission of smallpox. Somewhat of an uncertainty is the thought of bioengineered smallpox with additional gene copies of Interleukin-4 (IL-4), a cytokine, which, if over-expressed, suppresses IL-12, IFNγ, and specific cell mediated immunity, the critical factors needed for survival and recovery from an acute viral infection. Pharmaceuticals that serve to decrease morbidity and mortality would help to supplement the successful management of smallpox bioterrorism, biowarfare and its threats. Safe drugs "fill in" where there may be logistical encumbrances to orderly, "screened" vaccinations. In the overall strategy vs. smallpox terrorism, an important point is to deliver and administer vaccine to the possibly exposed individuals within the "seven day window" of incubation. Pharmaceutical GSH is safe and can "fill in" where there is a doubt as to whether an individual is within the seven-day period after initial exposure. Pharmaceutical GSH can serve as part of a comprehensive shield to augment education, and vaccination. The administration of pharmaceutical GSH would not hinder the efficacy of vaccination, rather it would help in view of the favorable effects of GSH in fostering Th1 over Th2 immunologic response patterns described and referenced below. Smallpox vaccine given by bifurcated needle induces strong vaccinia virus-specific CD8 (+) CTL and IFNγ-producing T cell responses. These are the responses that GSH enhances, provided it is present in normal intracellular concentrations within monocytes/macrophages, dendritic cells and B lymphocytes. Central to the pharmaceutical-based reduction of morbidity for people beyond the "seven day window" of the vaccine and others within "the herd", is the question of the major processes comprising the molecular pathology of smallpox at the tissue and cellular levels, host factors responsible for progression, and cause(s) of death. The cytopathic effects of smallpox cause death, and the data did not support previously promulgated theories attributing death to a bacterial sepsis syndrome seeded from the pustules. Death, which usually occurs during the second week of illness, (3-4 weeks after initial exposure) most likely results from the toxemia associated with circulating immune complexes and soluble Variola antigens. High doses of pharmaceutical GSH would serve in a safe, proactive capacity to replenish and maintain intracellular GSH concentrations and thereby interdict smallpox pathology at the tissue, cellular, and molecular levels. In case of exposure to smallpox, GSH should be able to interdict full development of the infection, perhaps converting it to a mild form comparable to smallpox occurring in a person vaccinated (10 years-20 years earlier, or to alastrim, i.e., Variola minor). GSH transporters are present on cell membranes as well as in mitochondria, and thus GSH from the extracellular fluid has access to cellular compartments. GSH can increase IFNγ, which in turn induces nitric oxide synthase (iNOS), which increases the potent antimicrobial .NO that clears viremias; reduce toxemia related to excessive, pro inflammatory cytokines since GSH can suppress NFκB activation, along with TNFα, IL-1β, COX-2 and other cytokines contributing to the "toxic" state of the patient.

The sequential clinical presentation of smallpox, starting from exposure, to asymptomatic viral replication with two early viremias, to prodroma, to rash, and then to complications, or recovery, or demise reveals unique stepwise pathogenesis: blocked initial host defense cellular reactions accompanied by unimpeded and asymptomatic viral replication with viremias, and later on, cascades of severe unregulated inflammatory reactions, localization of adherent Variola-laden leucocytes within dermal capillaries, leucocyte diapedesis from the capillaries to infect the skin, destructive rash, toxemias, circulating immune complexes with soluble Variola antigens, and complement activation, among others.

Poxviruses, including Variola, normally encode proteins for replication, such as DNA topoisomerase, and others, which when expressed by the infected host cells, blunt host immunologic strategies to contain and eradicate the infection, including blocking NFκB activation, chemokines, cytokines, IFNγ, complement fragments, and cell mediated immunity. Further, weaponized, biologically engineered pox variants can be instilled with added, encoded proteins that may blunt the immunologic strategies of immunized hosts, and lead to patterns of disease spread and severity not previously encountered.

Administration of GSH offers protective mechanisms through its properties, detailed and referenced previously, that can safely counter the Variola pathology in this phase. GSH is known to up-regulate Th1 response patterns and may, if used early, increase IL-12, IL-18, IFNγ, enhance specific cytotoxic lymphocytes, enhance NK cell activity, and increase Redox-sensitive protective responses.

In the early stage of asymptomatic Variola infection, many of the dendritic cells, macrophages and lymphocytes have not yet become infected and remain optimally responsive to GSH; however, host responses may be blocked by expressed viral proteins that are soluble and secreted. These can adversely affect neighboring cells that are as yet uninfected. Poxviruses encode soluble versions of receptors for the cytokines tumor necrosis factor, IL-1β, IFN-γ, IFN-α/β, and chemokines. These soluble viral proteins were found to bind to both uninfected and infected cells, thereby nullifying the protective, anti-viral effects of interferons and other host reactions. The soluble viral proteins serve as receptors as they bind to all cell surfaces, assuring unimpeded viral access and entry to new, uninfected cells. The infection therefore neutralizes host cell defenses even before the new cells have become infected. The counter strategy, in addition to timely quarantines, education and vaccinations can now include GSH as a safe pharmaceutical that: (a) raises numerically challenging quantities of defensive biomolecules vs. the viral proteins by up-regulating Th1 responses, (b) increases Redox-sensitive defense cells, like NK cells, and (c) attacks (reduces) the sensitive conformational disulfide bonds of viral evasion and replicatory proteins.

The fact that the smallpox vaccine is highly effective from the acute administration within seven days of likely exposure, among those that can safely take the vaccine and are assuredly within the 7 days, means that uninfected, or perhaps even the early-infected cell populations, can rapidly produce sufficient quantities of IL-12, IL-18, IFNγ, and factors to stimulate NK cells, and Variola-specific CTL's to overcome the viral evasion proteins and stop the infection in this early phase. Smallpox vaccine induces strong vaccinia virus-specific CD8+ CTL, and IFNγ-producing T cell responses. These are the same biochemical and cell responses that GSH rapidly enhances by fostering Th1 responses, NK cell activity, and protective Redox-sensitive responses. The pox proteins react directly and biochemically with host proteins, often via thiols and disulfides. Protein-protein interactions occur normally, and in other pathologic states. Some tend to be stoichiometric, and others not. This provides a rationale for the early use of high dose GSH treatment to quantitatively enhance host immune responses and numerically overwhelm the blocking pox virus protein(s). Upregulation of Th1 response patterns includes development of specific cytotoxic lymphocytes (CTL's) to kill and clear Variola infected cells.

Natural infection occurs following implantation of the virus on the oropharyngeal or respiratory mucosa. The infectious dose is unknown but is believed to be only a few virions. After the migration of the virus to, and multiplication in, regional lymph nodes, an asymptomatic viremia develops on about the third or fourth day, followed by multiplication of virus in the spleen, bone marrow, and lymph nodes.

GSH helps to eliminate the source of the offending pox proteins and represents an advantageous, non-stoichiometric result in favor of the host. GSH is non-toxic, as manufactured by ThyoGen and Kyowa Hakko, Co., Ltd. In Phase ½ studies, an increasing range of oral doses provided safe, significant, dose related increases in GSH in the Peripheral Blood Mononuclear Cells (PBMC's)

Another useful property of GSH, in addition to fostering Th1 pathways and Redox-sensitive protection, involves GSH and direct post translational modifications of viral proteins. GSH, as a function of changes in concentrations and in Redox Potentials, regulates proteins, cell signaling and other reactions by reducing disulfide bonds, or by glutathionylating the thiols of cysteine residues. This unfolds many proteins, and generally, inhibits enzymes and ligand binding to receptors. Unfolding of proteins may also expose crucial tyrosine sites that may be advantageously nitrosylated into nitrotyrosine, for example, within an activated macrophage producing nitric oxide that can now attack the active site tyrosine in viral DNA topoisomerase.

The probability of decreased thermodynamic stability of viral proteins expressed by the infected host cells, compared to host proteins, provides an interventional opportunity, based on the lower stability. Examples of this property, specifically in viral infections, include, among other HIV examples, glutathionylating HIV protease. Two conserved cysteines of HIV-1 protease (Cys-67, Cys-95) are readily glutathionylated, resulting in an enzyme preparation with significantly lower specific activity. Removal of the GSH restored the full activity of the enzyme preparations. Examples of inactivating disulfide bonds are studies of HIV gp120. Replicating HIV-1 with GSH exposure, in vitro, resulted in the selective decrease of specific glycoproteins, such as gp120, which are particularly rich in disulfide bonds. The effect of GSH on HIV gp120, was previously demonstrated in studies showing decreased viral infectivity, in vitro. This is likely due to selective inhibition of envelope glycoproteins, specifically the major such protein, gp120, rich in intra chain disulfide bonds. These GSH modifications of viral proteins are achieved without cytotoxicity.

The secondary viremia, early symptomatic phase, with fever and toxemia, occurs at days 8-14 post exposure, and herald the activation and loss of control of the NFκB family of transcription factors. The oxidative stress accompanying infections, the NADPH activation on macrophage plasma membranes, and the GSH consumption activate histone acetylation, and DNA unwinding that gives access to the extensive gene network that is NFκB dependent. Meanwhile, NFκB has been activated and there is excess production of: proinflammatory cytokines including Th1 cytokines IL-12 and IFNγ, IFNγ-dependent factors, IL-18, and Th2 cytokines IL-4; excess production of IL-4; excess production of adhesion molecules; induction of matrix metalloproteinases; uncontrolled cyclooxygenase-2 (COX-2); accelerated synthesis of eicosanoids; activation of inducible nitric oxide synthase (iNOS); chemokines, among other factors in the gene network of NFκB. These reactions, such as uncontrolled LOOH's; excesses of RNS; and the free radical reactions engendered by TNFα erode GSH concentrations. This leads to further declines in the Redox potential, and further exaggeration of the acute inflammatory reactions. Th1 response patterns decline further, and IL-12 and IFNγ are suppressed as GSH levels fall. The non-development of specific cytotoxic lymphocytes (CTL's) is part of the down-regulated Th1 response patterns and results in the unimpeded spread of Variola-infected mononuclear cells.

The expression of adhesion molecules on the infected mononuclear cells and on activated endothelium causes adherence of the mononuclear cells to injured endothelium. This is followed by diapedesis of the infected cells through the injured capillaries to form perivascular infiltrates in the dermis. Variola viruses then emerge to infect and destroy the skin cells, particularly those of the sebaceous glands of the face and "the bathing suit" regions. There is a reasonable surrogate example of pathologic processes that involve NFκB activation, its cascades, including adhesion molecules such as ICAM-1. Middle cerebral artery occlusions (MCAO) performed in Sprague-Dawley rats, produce inflammatory gene expression, including adhesion molecules, in cerebral ischemia, measurable using quantitative real-time RT-PCR analysis. Ischemia-reperfusion brain injury initiates an inflammatory response involving the expression of adhesion molecules cytokines, some of which are regulated by NFκB; the induced molecules, which are involved in the initiation of the inflammatory cascade may thus contribute to secondary cellular responses that lead to further brain damage.

Various types of pathologic changes occur in blood vessels that are damaged by oxidative stress (lipid peroxides, reactive oxygen species, reactive nitrogen species), as occurs in serious infections, ischemia, and other conditions characterized by GSH depletion. The junction between two endothelial cells is a "Tight Pavement" so nothing can leak. It is a slick, non-stick pavement so that blood flows smoothly. These lining cells actively produce molecules (e.g., Nitrous Oxide and $PGI_2$) that keep the blood vessels wide open and non-stick. GSH is mandatory to help Nitrous Oxide and $PGI_2$ carry out their critical functions. Otherwise, blood vessels narrow greatly, and blood components, like platelets and white blood cells, "gum up" the vessels. Adherent leucocytes in a small artery, approximate diameter 200 μm, also release substances that injure blood vessels, and some can move through the wall by diapedesis to attack surrounding tissue cells. This occurs in serious infections, ischemia and in other disorders due to elaboration of adhesion molecules on the leucocytes and on the endothelial cells, secondary to decreased GSH. This is the type of process seen when Variola laden mononuclear cells lodge in the dermal capillaries preparatory to invading the skin cells. Some leucocytes activate their surface NADPH oxidases which produce a variety of directly destructive reactive oxygen species. The effect could create large craters, and other ultra-structural irregularities in the endothelium. The aftermath of an adherent leucocyte that has caused free radical damage to the endothelium of a small artery can also be seen by SEM. Cratering and the overriding of lining cells can be observed. This occurs in serious infections, ischemia and other disorders characterized by GSH deficiency. Craters like these are seen only at times when adherent leucocytes are present and may represent direct erosion by ROS and RNS produced by monocytes/macrophages. The overriding of the endothelial cell is probably caused by increased production of matrix MMP that affect basement membrane materials and other supportive molecules of blood vessels.

A secondary viremia begins on about the eighth day and is followed by fever and toxemia. The virus, contained in leucocytes, then localizes in small blood vessels of the dermis and beneath the oral and pharyngeal mucosa and subsequently infects adjacent cells. The typical skin lesion starts with changes in the capillaries of the corium and is characterized by dilation, endothelial proliferation and perivascular mononuclear infiltration. In the adjacent epidermis, reticular degeneration of the cells occurs. The cells swell and the characteristic Guarneri bodies make their appearance. These are spherical bodies lying close to the nucleus and consist of collections of virus elementary bodies ranging in size from 2 to 8 microns. The swollen cells rupture, forming a vesicle, and the cells beneath the vesicle undergo a different type of degeneration resembling the "ballooning degeneration" that occurs in chickenpox.

MMP's (collagenases, gelatinases, and others constitute a family of 21 enzymes that attack the known components of the extra cellular matrix) are up-regulated by inflammatory cytokines and are operative in the spread of malignancies. The diapedesis of Variola-infected mononuclear cells, out of dermal capillaries, and their subsequent spread through the tight collagenous matrix of the dermis, to the epidermal layers, or penetrating through, into sebaceous glandular structures, are steps that are enhanced by MMP's. Maintaining high GSH concentrations can help to stem MMP activities and be of material benefit in curtailing the particularly destructive rash.

The cumulative tissue toxicities progress unabated in the approximately 30% to 60% of vaccination-naïve patients who succumb. The survivors make a recovery through a stormy course, and some are left with pitted scars in the skin. Along with the out-of-balance Th2 response patterns and unregulated inflammatory cascades that predominate as GSH levels fall, additional pathologic mechanisms are amplified. RNS stemming from excessive production of nitric oxide (.NO), combine with ROS and lipid peroxides (LOOH) to form RNS such as peroxynitrite (.NOO). Lipid peroxidation expands as IL-4 enhances 12- and 15-lipoxygenases, while simultaneously suppressing GSH peroxidases and other enzymes that normally dismantle LOOH's. Host proteins are attacked by the uncontrolled ROS, RNS, alkoxy radicals (LO.) and other reactive intermediates. There is therefore a substantial increase in oxidative stress which erodes GSH and other antioxidant defenses. Defenses give way as Th2 responses, IL-4, exaggerated inflammatory reactions, and oxidative stress cyclically amplify one another.

The intracellular GSH concentrations in this phase are probably quite low. There are several inducers of iNOS, including the proinflammatory cytokines, TNFα, IL-1β, and IFNγ. The latter, IFNγ, is probably not a significant factor since there are powerful Th2 processes in effect that serve to suppress IFNγ. In other inflammatory diseases, increased production of IFNγ can have undesirable consequences, since it is a potent activator of iNOS. By the time smallpox infections reach this imminently life-threatening stage, the number of unregulated and interacting pathways has become very complex. The processes that precede this complex late phase of smallpox infection would be more responsive to restoration of control mechanisms if GSH therapy starts early. However, strong public health measures, education of health professionals and other logistical systems must be in place to identify those who may have been exposed so that screened vaccinations, quarantines, and early GSH therapy can be instituted.

In the Toxic Phase, day 14 to day 30 post exposure, the patient typically experiences high fever, malaise, and prostration with headache and backache. A maculopapular rash then appears on the mucosa of the mouth and pharynx, face, and forearms, and spreads to the trunk and legs. Death, which usually occurs during the second week of illness, most likely results from toxemia associated with circulating immune complexes and soluble Variola antigens. There is little information about how individuals with different types of immune deficiency responded to natural smallpox infection. Smallpox was eradicated . . . before suitable techniques became available for measuring cell-mediated immunity. However, it is possible that the underlying cause of some cases of malignant and hemorrhagic smallpox resulted from defective immune responses.

The stoichiometry of using GSH, when starting in the late phase, is daunting because of the sheer number of pathways involved. While GSH has controlling properties, it is dependent upon its amplifying enzymes, such as GSH peroxidases, S-transferases, and GSH reductases. These enzymes are subject to the same oxidative, free radical damage as are other proteins, with the formation of carbonyls. Mitochondrial oxidative phosphorylation is also at risk when GSH levels decline, and lead to impaired synthesis of cellular macromolecules and to apoptosis. Apoptotic losses of macrophages, and antigen processing cells may be avoidable when low mitochondrial GSH levels are responsible. In vitro, GSH additions can prevent threatening mitochondrial induced apoptosis.

In overall summary, the maze of complex interactions described above have a central feature. They run out of control, and this is due, to some significant extent, to the heightened demands on a molecule that has limited availability to begin with: GSH. It is normally in high demand in all tissues, but past age 45 years, even apparently healthy individuals become comparatively deficient. GSH insufficiencies are worsened by tobacco, alcohol, intercurrent infections, diabetes mellitus, the use of pharmaceuticals such as the anti-inflammatory corticosteroids.

With the administration of GSH, which is orally bioavailable in a suitable formulation, shattered biomolecules, apoptogenic cell fragments, toxic by-products of lipid peroxidation, collapse of mitochondrial bioenergetics, and other progressive, irreparable, late pathologic events must be averted.

AIDS

GSH has been shown to inhibit HIV replication in chronically-infected cells and in cells acutely infected in vitro. This makes GSH replacement therapy attractive, because it has the potential to interfere with the expression of the integrated HIV genome, a site that is not attacked by the currently employed antiretrovirals (AZT, ddI, ddC, D4T). GSH may also have benefits in countering the excess free radical reactions in HIV infection, which may be attributable to: the hypersecretion of TNF-α by B-lymphocytes, in HIV infection, and the catalysis of arachidonic acid metabolism by the GP-120 protein of HIV. The physiologic requirements for GSH by key cell types of the immune system, and the ability of macrophages to take up intercellular GSH, as well as to metabolically interact with T-lymphocytes to indirectly cause their GSH to increase, offer additional reasons to attempt to correct the GSH deficiency in HIV/AIDS.

GSH deficiency is a key determinant of survival in HIV disease. GSH deficiency is associated with impaired survival in HIV disease (PNAS. Vol. 94, pp. 1967-1972 (1997)). The quest to raise GSH levels in cells is widely recognized as being extremely important in HIV/AIDS and other disorders, because the low cellular GSH levels in these disease processes permit more and more free radical reactions to propel the disorders. HIV is known to start pathologic free radical reactions that lead to the destruction of GSH, as well as exhaustion of other antioxidant systems and destruction of cellular organelles and macromolecules. In pre-clinical studies, GSH stops the replication of the virus at a unique point, and specifically prevents the production of toxic free radicals, prostaglandins, TNF-α, interleukins, and a spectrum of oxidized lipids and proteins that are immunosuppressive, cause muscle wasting and neurological symptoms. Restoring GSH levels could slow or stop the diseases progression, safely and economically.

In mammalian cells, oxidative stresses, i.e., low intracellular levels of reduced GSH, and relatively high levels of free radicals, activate certain cytokines, including NFκB and TNF-α, which, in turn, activate cellular transcription of the DNA to mRNA, resulting in translation of the mRNA To A Polypeptide Sequence. Antioxidants have been shown to block the induction of NFκB by oxidant agents. In a virus-infected cell, the viral genome is transcribed, resulting in viral RNA production, generally necessary for viral replication of RNA viruses and retroviruses. These processes require a relatively oxidized state of the cell, a condition which results from stress, low GSH levels, or the production of reduced cellular products. The mechanism that activates cellular transcription is evolutionarily highly conserved, and therefore it is unlikely that a set of mutations would escape this process, or that an organism in which mutated enzyme and receptor gene products in this pathway would be well adapted for survival. Thus, by maintaining a relatively reduced state of the cell (relatively reduced redox potential), viral transcription, a necessary step in late stage viral replication, is impeded.

The amplification effect of oxidative intracellular conditions on viral replication is compounded by the actions of various viruses and viral products that degrade GSH. For example, GP-120, an HIV surface glycoprotein having a large number of disulfide bonds, and normally present on the surface of infected cells, oxidizes GSH, resulting in reduced intracellular GSH levels. On the other hand, GSH reduces disulfide bonds of GP-120, decreasing or eliminating its biological activity, which in turn is necessary for viral infectivity. GSH therefore interferes with the production of such oxidized proteins, and degrades them once formed. GSH also participates in the destruction of hydrogen peroxide, which is a long-lived oxidative messenger which has been implicated in activating NFκB. Reactive oxygen intermediates as apparently widely used messengers in the activation of the NF-κB transcription factor and HIV-1.

In a cell which is actively replicating viral gene products, a cascade of events may occur which allow the cell to pass from a relatively quiescent stage with low viral activity to an active stage with massive viral replication and cell death, accompanied by a change in cellular redox potential; by maintaining adequate GSH levels, this cascade may be impeded.

Thus, certain viral infections, such as HIV, are associated with reduced GSH levels, and it is believed that by increasing intracellular GSH levels in infected cells, as well as increasing extracellular GSH, the replication of HIV may be interfered with, and the cascade of events delayed or halted. It is noted that AIDS may also be associated with reduced GSSG levels, implying an interference with de novo synthesis of GSH as well as the oxidation of existing GSH discussed above.

Initially after infection with HIV, there is an intense viral infection simulating a severe case of the flu, with massive replication of the virus. This acute phase passes within weeks, spontaneously, as the body mounts a largely successful immune defense. Thereafter, the individual has no outward manifestations of the infection. However, the virus continues to replicate, insidiously, within immune system tissues and cells, like lymph nodes, lymphoid nodules and special multidendritic cells that are found in various body cavities. This infection is not just a viral problem. The virus, in addition to replicating, causes excessive production of various free radicals and various cytokines in toxic or elevated levels. The latter are normally occurring biochemical substances that signal numerous reactions, usually existing in minuscule concentrations. Eventually, after an average of 7-10 years of seemingly quiescent HIV infection, the corrosive free radicals and the toxic levels of cytokines begin to cause symptoms, and failures in the immune system begin. Toxic factors, such as 15-HPETE, which is immunosuppressive, and TNF-α, which causes muscle wasting, are produced. The numbers of viral particles increase and the patient develops the Acquired Immune Deficiency Syndrome, AIDS, which may last 2-4 years before the individual's demise. AIDS, therefore, is not simply a virus infection, although the viral infection is believed to be an integral part of the etiology of the disease.

HIV has a powerful ability to mutate. It is this capability that makes it difficult to create a vaccine or to develop long-term anti-viral pharmaceutical treatments. As more people continue to fail the present complex pharmaceutical regimens, the number of resistant viral strains is increasing. This is a particularly dangerous pool of HIV and poses a considerable threat. These resistant mutants also add to the difficulties in developing vaccines. This epidemic infection is out of control, and the widely popularized polypharmaceutical regimens that are aimed only at lowering the number of viruses are proving to be too complex, too toxic, too costly, and too narrow. As a result, since the introduction of protease inhibitors, in combination with AZT-type drugs, increasing numbers of people are failing such therapies. Further, the continuing production of free radicals and cytokines, which may become largely independent of the virus, perpetuates the dysfunctions of the immune system, the gastrointestinal tract, the nervous system, and many other organs in AIDS. The published scientific literature indicates that many of these diverse organ system dysfunctions are due to systemic GSH deficiencies that are engendered by the virus and its free radicals. GSH is consumed in HIV infections because it is the principal, bulwark antioxidant versus free radicals. An additional cause of erosion of GSH levels is the presence of numerous disulfide bonds in HIV proteins, such as the GP-120 discussed above. Disulfide bonds react with GSH and oxidize it.

The current HIV/AIDS pharmaceuticals take good advantage of the concept of pharmaceutical synergism, wherein two different targets in one process are hit simultaneously. The effect is more than additive. The drugs now in use were selected to inhibit two very different points in the long path of viral replication. The pathway of viral replication can be depicted simply: point #1: Virus attacks and enters the cell; Viral gp120 protein and CD4+ cell receptors and others are involved; point #2: Virus makes DNA from its RNA; Reverse transcriptase is the enzyme involved (susceptible to AZT, ddI, ddC); point #3: Viral DNA is integrated into cells'

DNA; Integrase is the enzyme involved; point #4: Proviral DNA is inactive for a long time, but activators will start HIV replicating rapidly; NFκB is the activator of dormant HIV DNA and GSH levels must be low for activation to occur; and point #5: Viral RNA is produced, along with viral membranes and proteins, which are assembled; Viral protease is involved (susceptible to GSH, Protease Inhibitors). Point #2 was the earliest point of attack, using AZT-types of drugs, including ddI, ddC and others. These are toxic and eventually viruses become resistant to these Reverse Transcriptase inhibitors. Point #5 is a late replication step, and this is where protease inhibitors function. The drug blocks viral protease, an enzyme that snips long protein chains to just the right length so the viral coat fits exactly around the nucleic acid core, and that proteins having different biological activities are separated. By themselves, protease inhibitors foster the rapid development of resistant, mutant strains.

By combining Reverse Transcriptase inhibitors plus protease inhibitors, synergism was obtained and the amounts of viral particles in the plasma plummeted, while the speed of the developing mutant resistant viral strains was slowed, compared to using only one type of inhibitor. The initial promise of these combination therapies or "cocktails" has been tainted by increasing numbers of failures, which are expected to rise as resistant mutants develop, albeit more slowly than the use of the drugs separately.

New therapies include additional drugs in the classes of Reverse Transcriptase inhibitors and protease inhibitors. Also, drugs are in development to block point #3, wherein the enzyme, integrase, integrates the HIV DNA into the infected cell's DNA, analogous to splicing a small length of wire into a longer wire. Vaccine development also continues, although prospects seem poor because HIV appears to be a moving target and seems to change as rapidly as a chameleon. Vaccine development is also impaired by the immune cell affinity of the virus.

Human Immunodeficiency virus-infected individuals have lowered levels of serum acid-soluble thiols and GSH in plasma, peripheral blood monocytes, and lung epithelial lining fluid. In addition, it has been shown that CD4+ and CD8+ T cells with high intracellular GSH levels are selectively lost as HIV infection progresses. This deficiency may potentiate HIV replication and accelerate disease progression, especially in individuals with increased concentrations of inflammatory cytokines because such cytokines stimulate HIV replication more efficiently in GSH-depleted cells. GSH and GSH precursors such as N-acetyl cysteine (NAC) can inhibit cytokine-stimulated HIV expression and replication in acutely infected cells, chronically infected cells, and in normal peripheral blood mononuclear cells.

It is noted that depletion of GSH is also associated with a processes known as apoptosis, or programmed cell death. Thus, intercellular processes that artificially deplete GSH may lead to cell death, even if the underlying process itself is not lethal.

Diabetes Mellitus

Diabetes mellitus is found in two forms, childhood or autoimmune (type I, IDDM) and late-onset or non-insulin dependent (type II, NIDDM). The former constitute about 30% and the remainder represent the bulk of cases seen. Onset is generally sudden for Type I, and insidious for Type II. Symptoms include excessive urination, hunger and thirst with a slow steady loss of weight in the first form. Obesity is often associated with the second form and has been thought to be a causal factor in susceptible individuals. Blood sugar is often high and there is frequent spilling of sugar in the urine. If the condition goes untreated, the victim may develop ketoacidosis with a foul-smelling breath similar to someone who has been drinking alcohol. The immediate medical complications of untreated diabetes can include nervous system symptoms, and even diabetic coma.

Because of the continuous and pernicious occurrence of hyperglucosemia (very high blood sugar levels), a non-enzymatic chemical reaction occurs called glycation. Since glycation occurs far more frequently inside cells, the inactivation of essential enzyme proteins happens almost continually. One of the most critical enzymes, γ-glutamyl-cysteine synthetase, is glycated and readily inactivated. This enzyme is the crucial step in the biosynthesis of GSH in the liver. The net result of this particular glycation is a deficiency in the production of GSH in diabetics. Normally, adults produce 8-10 grams every 24 hours, and it is rapidly oxidized by the cells. GSH is in high demand throughout the body for multiple, essential functions, for example, within all mitochondria, to produce chemical energy called ATP. Brain cells, heart cells, and others simply will not function well and can be destroyed through apoptosis.

GSH is the major antioxidant in the human body and the only one we are able to synthesize, de novo. It is also the most common small molecular weight thiol in both plants and animals. Without GSH, the immune system cannot function, and the central and peripheral nervous systems become aberrant and then cease to function. Because of the dependence on GSH as the carrier of nitric oxide, a vasodilator responsible for control of vascular tone, the cardiovascular system does not function well and eventually fails. Since all epithelial cells seem to require GSH, the intestinal lining cells don't function properly and valuable micronutrients are lost, nutrition is compromised, and microbes are given portals of entry to cause infections.

The use of GSH precursors cannot help to control the GSH deficiency due to the destruction of the rate-limiting enzyme by glycation. As GSH deficiency becomes more profound, the well-known sequellae of diabetes progress in severity. The complications described below are essentially due to runaway free radical damage since the available GSH supplies in diabetics are insufficient.

Reducing sugars are known to interact with free amino groups in proteins, lipids, and nucleic acids to form Amadori product and produce reactive oxygen species through the glycation reaction. Under diabetic conditions, glucose level is elevated and the glycated proteins increased. Cu,Zn-SOD has been shown to be glycated and inactivated under diabetic conditions and that ROS produced from the Amadori product caused site-specific fragmentation of Cu,Zn-SOD. Fructose, which is produced through polyol pathway, has stronger glycating capacity than glucose because the physiologic proportion of the linear form is higher than that of cyclized form. Fructose, as well as ribose, can bring about apoptosis in pancreatic β islet cell line. Levels of intracellular peroxides, protein carbonyls, and malondialdehyde are increased in the presence of fructose. In addition, methylglyoxal and 3-deoxyglucosone have also been shown to induce apoptotic cell death. 3-Deoxyglucosone, a 2-oxoaldehyde, is produced through the degradation of Amadori compounds. Both compounds are elevated during hyperglycemia and accelerate the glycation reaction. These compounds are toxic to cells, due to their high reactivity, and a scavenging system with NADPH-dependent reducing activity exists, including aldehyde reductase.

Cell-cell adhesion is critical in generation of effective immune responses and is dependent upon the expression of a variety of cell surface receptors. Intercellular adhesion molecule-1 (ICAM-1; CD54) and vascular cell adhesion molecule (VCAM-1; CD 106) are inducible cell surface glycoproteins. The expression of these surface proteins are known to be induced in response to activators such as cytokines (TNF-α, IL-1 α & β), PMA, lipopolysaccharide and oxidants. The ligands for ICAM-1 and VCAM-1 on lymphocyte are LFA-1 (CD11a/CD18) and VLA-4, respectively. The inappropriate or abnormal sequestration of leukocytes at specific sites is a central component in the development of a variety of autoimmune diseases and pathologic inflammatory disorders. Focal expression of ICAM-1 have been reported in arterial endothelium overlying early foam cell lesions in both dietary and genetic models of atherosclerosis in rabbits. A role of VCAM-1 in the progression of coronary lesions has also been suggested. Loss or gain of cell surface molecules is thought to determine the mobilization, emigration and invasiveness of epithelial cancer cells. Monocytes from patients with diabetes mellitus are known to have increased adhesion to endothelial cells in culture. Regulation of adhesion molecule expression and function by reactive oxygen species via specific redox sensitive mechanisms have been reported. Antioxidants can block induced adhesion molecule expression and cell-cell adhesion.

The diabetic will become more susceptible to infections because the immune system approaches collapse when GSH levels fall, analogous to certain defects seen in HIV/AIDS. Peripheral vasculature becomes compromised and blood supply to the extremities is severely diminished because GSH is not available in sufficient amounts to stabilize the nitric oxide (.NO) to effectively exert its vascular dilation (relaxation) property. Gangrene is a common sequel and successive amputations are often the result in later years.

Peripheral neuropathies, the loss of sensation commonly of the feet and lower extremities develop, often followed by aberrant sensations like burning or itching, which can't be controlled. Retinopathy and nephropathy are later events that are actually due to microangiopathy, excessive budding and growth of new blood vessels and capillaries, which often will bleed due to weakness of the new vessel walls. This bleeding causes damage to the retina and kidneys with resulting blindness and renal shutdown, the latter results in required dialysis. Cataracts occur with increasing frequency as the GSH deficiency deepens.

Large and medium sized arteries become sites of accelerated, severe atherosclerosis, with myocardial infarcts at early ages, and of a more severe degree. If diabetics go into heart failure, their mortality rates at one year later are far greater than in non-diabetics. Further, if coronary angioplasty is used to treat their severe atherosclerosis, diabetics are much more likely to have renarrowing of cardiac vessels, termed restenosis.

The above complications are due, in large measure, to GSH deficiency and ongoing free radical reactions. These sequellae frequently and eventually occur despite the use of insulin injections daily that lower blood sugar levels. Good control of blood sugar levels is difficult for the majority of diabetics.

Macular Degeneration

GSH may be used to treat Macular Degeneration. Age-related macular degeneration (ARMD) is the disease characterized by either a slow (dry form) or rapid (wet form) onset of destruction and irrevocable loss of rods and cones in the macula of the eye. The macula is the approximate center of the retina wherein the lens of the eye focuses its most intense light. The visual cells, known as the rods and cones, are an outgrowth and active part of the central nervous system. They are responsible and essential for the fine visual discrimination required to see clear details such as faces and facial expression, reading, driving, operation of machinery and electrical equipment and general recognition of surroundings. Ultimately, the destruction of the rods and cones leads to functional, legal blindness. Since there is no overt pain associated with the condition, the first warnings of onset are usually noticeable loss of visual acuity. This may already signal late stage events. It is now thought that one of the very first events in this pathologic process is the formation of a material called "drusen".

Drusen first appears as either patches or diffuse drops of yellow material deposited upon the surface of the retina in the macula lutea or yellow spot. This is the area of the retina where sunlight is focused by the lens. It is the area of the retina that contains the highest density of rods for acuity. Although cones, which detect color, are lost as well in this disease, it is believed to be loss of rods that causes the blindness. Drusen has been chemically analyzed and found to be composed of a mixture of lipids, much of which are peroxidized by free radical reactions. The Drusen first appears as small collections of material at the base of Bruch's membrane. This produces "bubbles" which push the first layer of cells up off the membrane. Vascular budding, neovascular growth, first appears in these channels.

This first layer of cells is unique. They are retinal pigmented epithelial (RPE) cells and these cells are distantly related to CNS microglia and have a phagocytic function. They are also the layer of cells immediately below the primary retinal cells, the rods and cones. The RPE cells are believed to serve a protective function for the rods and cones since they consume the debris cast off by the rods and cones. It is not known yet whether the pigmented material serves a protective function or is related to phagocytosis only. However, this pigment, although concentrated in organelles, is believed to be composed of peroxidized lipids and melanin.

It is believed, because of the order of events in model systems, that the loss of RPE cells occurs first in ARMD (Age Related Macular Degeneration). Once an area of the retinal macula is devoid of RPE cells, loss of rods, and eventually some cones, occurs. Finally, budding of capillaries begins and we see the typical microangiopathy associated with late stage ARMD. It is also known that RPE cells require large quantities of GSH for their proper functioning. When GSH levels drop severely in these cells, in cell cultures where they can be studied, these cells begin to die. When cultures of these cells are supplemented with GSH in the medium, they thrive. There is increasing evidence that progression of the disease is paced by a more profound deficiency in GSH within the retina and probably within these cells, as indicated by cell culture studies.

It is generally believed that "near" ultraviolet (UVB) and visual light of high intensity primarily from sunlight is a strong contributing factor of ARMD. People with light-colored irises constitute a population at high risk, as do those with jobs that leave them outdoors and in equatorial areas where sunlight is most intense. Additional free radical insults, like smoking, add to the risk of developing ARMD.

Several approaches have been recently tested, including chemotherapy, without success. Currently, there is no effective therapy to treat ARMD. Laser therapy has been developed which has been used widely to slow the damage produced in the slow onset form of the disease by cauterizing neovascular growth. However the eventual outcome of the disease, once it has started to progress, is certain.

GSH acts to combat both direct and indirect effects of free radical reactions, as well as altering redox-sensitive gene expression.

Use of GSH for Cellular Regulation with Respect to Reactive Oxygen Species

There are a number of types of messengers carrying signals between cells. One type of messenger which has received significant attention recently are small molecule oxidative or free radical agents, which include reactive oxygen species (ROS). These messengers often act by a non-specific interaction with biological macromolecules which may result in a change in configuration. For example, protein secondary structure is typically controlled by cysteine residues, which are susceptible to oxidation with the formation of disulfide bonds. Oxidization of these bonds forming linkages may result in substantial changes in protein configuration and function.

It has thus become increasingly apparent that $O_2^-$ and $H_2O_2$ are signaling molecules, changing the behavior of proteins as diverse as transcription factors and membrane receptors by virtue of their ability to undergo redox reactions with the proteins with which they interact, converting —SH groups to disulfide bonds, for example, and changing the oxidation states of enzyme-associated transition metals. As signaling molecules, $O_2^-$ and $H_2O_2$ are manufactured by several types of cells, including fibroblasts, endothelial and vascular smooth muscle cells, neurons, ova, spermatozoa and cells of the carotid body. All these cell types appear to use an NAD(P)H oxidase similar to the classical leukocyte NADPH oxidase to produce these oxidants. The stimuli that elicit oxidant production, however, and the purposes for which the oxidants are employed, vary from cell to cell.

Fibroblasts manufacture small but significant amounts of $O_2^-$ in response to inflammatory mediators such as N-formylated peptides and interleukin-1. The $O_2^-$ produced by these cells has been postulated to function as a signaling molecule. Optical spectroscopy has shown that fibroblast membranes contain a heme protein that is different from the flavocytochrome subunit of the leukocyte NADPH oxidase but has properties very similar to those of the leukocyte protein. This heme protein has been suggested as the source of the $O_2^-$ made by these cells.

Endothelial and vascular smooth muscle cells use an NAD(P)H oxidase to produce $O_2^-$ in response to angiotensin II, a peptide hormone that increases blood pressure. This increase in blood pressure appears to be due to the consumption by $O_2^-$ of the NO. that is generated on a continuing basis by the endothelial cells. The resulting fall in NO. concentration raises blood pressure by attenuating or eliminating the vasodilatory effect of NO. that normally prevails in the vascular tree.

Neuronal cells in culture produce oxidants when exposed to amyloid β-peptide, found in amyloid deposits seen in the brains of patients with Alzheimer's disease, or related peptides from other amyloid diseases. The possibility that this $O_2^-$ is produced by an NADPH oxidase is suggested by the observation that flavoprotein inhibitors known to act on the leukocyte NADPH oxidase also inhibit oxidant production in this system. The production of oxidants may be part of a defense used by the neuron against the peptide, with these oxidants perhaps reacting with the peptide to render it susceptible to proteolytic cleavage.

At the moment of fertilization, a membrane NADPH oxidase in sea urchin ova is activated to produce large amounts of $H_2O_2$. This oxidant cross-links the proteins of the fertilization membrane by forming dityrosyl bridges, making the membrane impermeable to spermatozoa and thereby preventing polyspermy. This mechanism is common to other species $O_2^-$ appears to be necessary for the normal function of spermatozoa. When stimulated by a calcium ionophore, normal spermatozoa generate a 3- to 5-min burst of $O_2$. The $O_2^-$ produced in this reaction is involved in capacitation of the spermatozoa, because the acrosomal response to a number of stimuli is suppressed by superoxide dismutase. On the other hand, spermatozoa that produce $O_2^-$ without stimulation are functionally abnormal, perhaps because of a generalized disruption in their signaling machinery.

The carotid body is a small organ located at the bifurcation of the common carotid artery that measures the oxygen tension of the blood. This organ manufactures $H_2O_2$ on a continuing basis, and immunological analysis has shown that its cells contain all 4 of the specific subunits of the leukocyte NADPH oxidase, or proteins very closely related to those subunits. It has been postulated that a carotid body NADPH oxidase very similar or identical to the leukocyte NADPH oxidase is a key component of the oxygen-measuring apparatus of the carotid body.

Thus, in addition to phosphorylation as a control mechanism over regulatory protein configuration and function, reactive oxygen species may also play an important role in cellular regulation and signaling. Selective cysteine oxidation-reduction also serves as an important mechanism for post-translational modification of protein function. This mechanism, termed "redox regulation", has been implicated in a variety of cellular processes such as DNA synthesis, enzyme activation, gene expression, and cell cycle regulation.

Thioredoxin (TRX) is a pleiotropic cellular factor which has thiol-mediated redox activity and plays important roles in regulation of cellular processes, including gene expression. TRX exists either in a reduced, or oxidized form and participates in redox reactions through the reversible oxidation of this active center dithiol. Activity of a number of transcription factors is post-translationally altered by redox modification(s) of specific cysteine residue(s). One such factor is NFκB, whose DNA-binding activity is altered by TRX treatment in vitro. The DNA-binding activity of AP-1 is modified by a DNA repair enzyme, Redox Factor-1 (Ref-1). Ref-1 activity is in turn modified by various redox-active compounds, including TRX. TRX translocates from the cytoplasm into the nucleus in response to PMA treatment to associate directly with Ref-1 and modulates not only the DNA-binding but also the transcriptional activity of the AP-1 molecule.

Human thioredoxin (hTRX) has thus been shown to be an important redox regulator in those biological processes. hTRX can function directly by interacting with the target molecules such as NFκB transcription factor, or indirectly via another redox protein known as redox factor 1 (Ref-1).

Cellular redox status modulates various aspects of cellular events including proliferation and apoptosis. TRX is a small (13 kDa), ubiquitous protein with two redox-active half-cystine residues in an active center, -Trp-Cys-Gly-Pro-Cys-, and is also known as adult T-cell leukemia-derived factor (ADF) involved in HTLV-I leukemogenesis. The pathway for the reduction of a protein disulfide by TRX entails nucleophilic attack by one of the active-site SH to form a protein-protein disulfide followed by intramolecular displacement of the reduced target proteins with concomitant formation of oxidized TRX. Besides the activity as an autocrine growth factor for HTLV-I-infected T cells and Epstein-Barr virus-transformed lymphocytes, numerous studies have shown the importance of ADF/TRX as a cellular reducing catalyst in human physiology.

In vitro and in vivo experiments showed that TRX augmented the DNA-binding and transcriptional activities of the p50 subunit of NFκB by reducing Cys 62 of p50. Direct physical association of TRX and an oligopeptide from NFκB p50 has been revealed by NMR study in vitro. Redox regulation of Jun and Fos molecules has also been implicated. Various antioxidants strongly activate the DNA-binding and transactivation abilities of AP-1 complex. TRX enhances the DNA-binding activity of Jun and Fos, in a process which requires other molecules, such as redox factor-1 (Ref-1).

NFκB regulates expression of a wide variety of cellular and viral genes. These genes include cytokines such as IL-2, IL-6, IL-8, GM-CSF and TNF, cell adhesion molecules such as ICAM-1 and E-selectin, inducible nitric oxidase synthase (iNOS) and viruses such as human immunodeficiency virus (HIV) and cytomegalovirus. Through the causal relationship with these genes, NFκB is considered to be causally involved in the currently intractable diseases such as acquired immunodeficiency syndrome (AIDS), hematogenic cancer cell metastasis and rheumatoid arthritis (RA). Although the genes induced by NFκB are variable according to the context of cell lineage and are also under the control of the other transcription factors, NFκB plays a major role in regulation of these genes and thus contributes a great deal to the pathogenesis. Therefore, biochemical intervention of NFκB should conceivably interfere the pathogenic process and would be effective for the treatment.

NFκB consists of two subunit molecules, p65 and p50, and usually exists as a molecular complex with an inhibitory molecule, IκB, in the cytosol. Upon stimulation of the cells such as by proinflammatory cytokines, IL-1 and TNF, IκB is dissociated and NFκB is translocated to the nucleus and activates expression of target genes. Thus activity of NFκB itself is regulated by the upstream regulatory mechanism. Not much is know about the upstream signaling cascade. However, there are at least two independent steps in the NFκB activation cascade: kinase pathways and redox-signaling pathway. These two distinct pathways are involved in the NFκB activation cascade in a coordinate fashion, which may contribute to a fine tune, as well as fail-safe, regulation of NFκB activity.

At least two distinct types of kinase pathways are known to be involved in NFκB activation: NFκB kinase and IκB kinase. NFκB kinase is a 43 kD serine kinase, associated with NFκB. This kinase phosphorylates both subunits of NFκB and dissociates it from IκB. There is another kinase or kinases that is known to phosphorylate IκB. Consistent with these findings, NFκB was shown to be phosphorylated in some cell lines and IκB was phosphorylated in others in response to stimulation with TNF or IL-1. In most of the cases, NFκB dissociation by kinase cascade is a primary step of NFκB activation.

After dissociation from IKB, however, NFκB must go through the redox regulation by cellular reducing catalyst, thioredoxin (TRX). TRX is known to participate in redox reactions through reversible oxidation of its active center dithiol to a disulfide. Human TRX has been initially identified as a factor responsible for induction of the A subunit of interleukin-2 receptor which is now known to be under the control of NFκB. It is known that NFκB cannot bind to the κB DNA sequence of the target genes until it is reduced.

NFκB appears to have a novel DNA-binding structure called beta-barrel, a group of beta sheets stretching toward the target DNA. There is a loop in the tip of the beta barrel structure that intercalates with the nucleotide bases and is considered to make a direct contact with the DNA. This DNA-binding loop contains the cysteine 62 residue of NFκB that is likely the target of redox regulation as a proton donor from TRX. A boot-shaped hollow on the surface of TRX containing the redox-active cysteines could stably recognize the DNA-binding loop of p50 and is likely to reduce the oxidized cysteine by donating protons in a structure-dependent way. Therefore, the reduction of NFκB by TRX is considered to be specific.

Not much is known about the initiation of the NFκB signaling cascades. However, pretreatment of cells with antioxidants such as N-acetyl-cysteine (NAC) or a-lipoic acid blocks NFκB. NAC can also block the induction of TRX. Therefore, anti-NFκB actions of antioxidants are considered to be two-fold: 1) blocking the signaling immediately downstream of the signal elicitation, and 2) suppression of induction of the redox effector TRX. It is noted that, in mammals without chronic diseases, such as HIV infection, diabetes, etc, which might impair physiologic GSH metabolism, a strategy for the pharmaceutical administration of other antioxidants which improve GSH metabolism or compounds which are themselves appropriate antioxidants may be employed. It is noted that NAC has been shown to have certain neurological toxicity in chronic administration, and therefore this compound is likely inappropriate. On the other hand, lipoic acid may be an advantageous antioxidant alone, or in combination with GSH. Because of the sensitivity of GSH oral administration to the particular method of administration, α-lipoic acid may have to be administered separately.

The intracellular redox cascade involves successive reduction of oxygen by addition of four electrons and redox regulation of a target protein. Among these ROI hydrogen peroxide has a longest half-life and is considered to be a mediator of oxidative signal. On the other hand, cellular reducing system such as TRX counteracts the action of hydrogen peroxide. The intensity of the oxidative signal may be modulated by the internal GSH level. Similarly, total GSH/GSSG content may influence the responsiveness of the cellular redox signaling. Therefore, intracellular cysteine required to produce GSH.

Membrane receptors and transporters, including, for example, the insulin receptor and receptors for certain neurotransmitters, are regulated by the redox state of the cell. A very large number of enzymes are also regulated by the cell's redox state. A partial list of proteins whose function is regulated by oxidation-reduction is provided. Enzymes: Collagenase p21Ras guanine nucleotide-binding protein; Protein tyrosine phosphatase; p56Lck protein tyrosine kinase; Glycogen phosphorylase phosphatase; Glycogen synthase; Phosphofructokinase; Fructose-1,6-bisphosphatase; Hexokinase; Pyruvate kinase; Glucose-6-phosphate dehydrogenase; 3-Hydroxy-3-methylglutaryl CoA reductase; Serotonin N-acetyltransferase; Guanylate cyclase; Medium-chain fatty acyl CoA dehydrogenase; Xanthine dehydrogenase; Chloroplast NADP-linked glyceraldehyde-3-phosphate dehydrogenase; Chloroplast NADP-linked malate dehydrogenase; Chloroplast sedoheptulose bisphosphatase; Fructose bisphosphatase; NADP-malic enzyme; 3a-Hydroxysteroid dehydrogenase; DsbA protein disulfide isomerase from *E. coli*; Creatine kinase; Sarcoplasmic reticulum Ca2+-ATPase; Transcription factors: NFκB; AP-1 (jun/fos); SoxR (132,133); SoxS; OxyR; Hypoxia-inducible factor 1; Thyroid transcription factor I; Glucocorticoid receptor; Sp1; Receptors: NMDA receptor; Insulin receptor; Ryanodine receptor; HoxB5; c-Myb; v-Rel; p53; Isl-1; Others: Erythropoietin RNA-binding protein Reactive oxygen species (ROS) are implicated in the pathogenesis of a wide variety of human diseases. Recent evidence suggests that at moderately high concentrations, certain forms of ROS such as $H_2O_2$ may act as signal transduction messengers. At least two well-defined transcription factors, nuclear factor (NFκB) and activator protein (AP)-1 have been identified to be regulated by the intracellular redox state. Binding sites of the redox-regulated transcription factors NFκB and AP-1 are located in the promoter region of a large variety of genes that are directly involved in the pathogenesis of diseases, e.g., AIDS, cancer, atherosclerosis and diabetic complications. Biochemical and clinical studies have indicated that antioxidant therapy may be useful in the treatment of disease. Critical steps in the signal transduction cascade are sensitive to oxidants and antioxidants. Many basic events of cell regulation such as protein phosphorylation and binding of transcription factors to consensus sites on DNA are driven by physiological oxidant-antioxidant homeostasis, especially by the thiol-disulfide balance. Endogenous glutathione and thioredoxin systems may therefore be considered to be effective regulators of redox-sensitive gene expression. By controlling redox cascades by using antioxidants, for example, treatments for several diseases may be possible, such as hematogenic cancer cell metastasis and AIDS.

The heat-shock (HS) response is a ubiquitous cellular response to stress, involving the transcriptional activation of HS genes. $H_2O_2$ has been shown to induce a concentration-dependent transactivation and DNA-binding activity of heat-shock factor-1 (HSF-1). DNA-binding activity was, however, lower with $H_2O_2$ than with HS, thus providing evidence of a dual regulation of HSF by oxidants. The effects of $H_2O_2$ in vitro were reversed by the SH reducing agent dithiothreitol and the endogenous reductor thioredoxin (TRX). In addition, TRX also restored the DNA-binding activity of HSF oxidized in vivo, while it was found to be itself induced in vivo by both HS and $H_2O_2$. Thus, $H_2O_2$ exerts dual effects on the activation and the DNA-binding activity of HSF: on the one hand, $H_2O_2$ favors the nuclear translocation of HSF, while on the other hand, it alters HSF-DNA-binding activity, most likely by oxidizing critical cysteine residues within the DNA-binding domain. HSF thus belongs to the group of ROS-modulated transcription factors.

The mammalian stress response evokes a series of neuroendocrine responses that activate the hypothalamic-pituitary-adrenal (HPA) axis and the sympathetic nervous system. Coordinated interactions between stress response systems, occurring at multiple levels including the brain, pituitary gland, adrenal gland, and peripheral tissues, are required for the maintenance of homeostatic plateau. Glucocorticoids, as a major peripheral effector of the HPA axis, play an essential role in re-establishing homeostatic status in every peripheral tissue in human. On the other hand, the adaptive responses are also operated against various intrinsic or extrinsic forces that disturb cellular homeostasis as a part of local host-defense mechanisms at a cellular level. Currently, reduction/oxidation (redox) reactions are intimately involved in the control of biological processes including modulation of the function of transcription factors, e.g., AP-1 and NFκB. Cells contain endogenous buffering systems against excessive production of reactive oxygen intermediates (ROIs) to preserve cellular metabolism through the expression and regulation of many enzymes.

Glucocorticoids, on binding to the glucocorticoid receptor (GR), promote the dissociation of heat shock proteins (HSPs), and the ligand-receptor complex translocates to the nucleus then binds to palindromic DNA sequences, called glucocorticoid response elements (GREs). After binding to DNA, the GR differentially regulates target gene expression to produce hormone action, interacting with or without other transcription factors and coactivators/corepressors. The GR has a modular structure mainly consisting of a central DNA binding domain (DBD), nuclear localization signals, a ligand binding domain (LBD), and several transcription activation functions. The human GR contains 20 cysteine residues, concentrated in the central region spanning the DBD and LBD. The cysteine residues in each domain have been shown to be crucial for maintaining both structure and function of those domains. For examples, it has already been shown that conversion of SH in the DBD to disulfides blocks GR binding to DNA cellulose, and that metal ions, which have high affinity for thiols interfere with the DBD-DNA interaction.

The TRX system operates as an endogenous defense machinery for glucocorticoid-mediated stress responses against oxidative stress. TRX is considered to be involved in transcriptional processes: for example, NFκB activation is inhibited, whereas AP-1 activity is induced by TRX. Moreover, the GR in the isolated rat cytosol is shown to be stabilized and maintained in their reduced, ligand-binding form by TRX. The functional interaction between cellular oxistress, TRX, and GR, and indicate that cellular redox state and TRX levels are important determinants of cellular sensitivity to glucocorticoids. Thus, TRX systems may control homeostasis not only by, for example, sequestrating ROIs, but also by fine tuning of hormonal signals. These phenomena appear to be rationale, for example during inflammation, where cells are believed to be exposed to severe oxidative stress, where suppression of glucocorticoid action may potentiate endogenous defense mechanisms and prevent premature termination of the cascade of inflammatory reactions for self-defense. Increase in cellular TRX levels may restore the receptor activity and permit the GR to efficiently communicate with target genes. Resultant activation of anti-inflammatory genes and/or repression of inflammatory genes may prevent overshoot of inflammation. This process may be modulated by an alteration of the redox potential of the cell and the concentration of reduced GSH in the intracellular fluid. Therefore, glucocorticoid function may be modulated by glutathione administration. Thus, treatment of chronic inflammatory conditions, such as rheumatoid arthritis, as well as other immune and autoimmune disorders, may also benefit from treatment with glutathione.

The role of NFκB in HIV life cycle is critical especially in virus reactivation process within the latently infected cells has been widely accepted. After activation through intracellular signaling pathways such as those elicited by T cell receptor antigen complex or by receptors for IL-1 or TNF, NFκB initiates HIV gene expression by binding to the target DNA element within the promoter region of HIV LTR. Then, the virus-encoded trans-activator Tat is produced and triggers explosive viral replication. Since activation pathway of HIV gene expression by cellular transcription factor NFκB conceptually precedes activation by viral trans-activators, it is conceptual to ascribe NFκB as a determinant of the maintenance and breakdown of the viral latency. Antioxidants may be effective in treating AIDS by blocking HIV replication.

Another situation where NFκB plays a role is hematogenic cancer cell metastasis. NFκB induces E-selectin (also known as ELAM-1) on the surface of vascular endothelial cells. Since some cancer cells constitutively express a ligand for E-selectin, called sialyl-LewisX antigen, on their cell surface, induction of E-selectin is considered to be a rate determining step of cancer cell-endothelial cell interaction. For example, when primary human umbilical venous endothelial cells (HUVEC) are treated with IL-1 or TNF, nuclear translocation of NFκB is observed, followed by the augmented expression of E-selectin. In one study, the cell-to-cell interaction between HUVEC and QG90 cell, a tumor cell line derived from human small cell carcinoma of the lung expressing sialyl-LewisX antigen was studied, and it was found that IL-1 was able to induce the attachment of cancer cells to HUVEC. However, pretreatment of HUVEC with N-acetylcysteine, aspirin or pentoxyphillin efficiently blocked the cell-to-cell attachment in a dose-dependent manner.

Pigmented Epithelium Derived Factor (PEDF)

It is well known that solid tumors, such as carcinomas, require neovascularization to continue growth beyond a few millimeters in size. This is because, as with all tissues, they need oxygen and must rid themselves of toxic metabolic products. Further, rapidly growing tumors may have demands well in excess of that of normal tissues due to a high rate of cell replication. Therefore, one technique which has been sought to be employed in fighting tumors is the use of pharmaceuticals and agents that block neovascularization, for example tumor necrosis factor, endostatin, angiostatin, and other agents. One agent that has aroused interest is Pigmented Epithelium Derived Factor (PEDF), a protein of the serine protease inhibitor (serpin) supergene family, but with characteristics of a substrate rather than inhibitor. PEDF was named for its association with the pigmented RPE cells of the macula, described above.

PEDF is a potent autocrine and paracrine hormone which blocks epithelial cell proliferation (including vascular epithelial cells, necessary for neovascularization), and promotes cellular differentiation, and is neurotrophic and neuroprotective. Subsequent studies have confirmed that PEDF or its isoforms are widely distributed throughout the body, but with relatively high concentration in the pigmented epithelial cells of the retina and central nervous system. PEDF may help cells resist apoptosis. Glutathione depletion has also been directly associated with failure of differentiation. PEDF binds to extracellular matrixes. Pigment epithelium-derived factor (PEDF) binds to glycosaminoglycans: analysis of the binding site. PEDF is among the most potent direct angiogenesis factors known. In the eye, it prevents ingrowth of blood vessels in the lens, retina and vitreous body of the eye. PEDF is a dramatic enhancer of cellular differentiation, and is capable, for example, of inducing retinoblastoma cells to retrotransform into normal appearing cells. PEDF protects neural tissue against an array of injurious factors, for example, against the excitatory neurotoxicity of glutamate.

PEDF is produced by the stromal cells of the endometrium and has a strong effect on the growth and differentiation of the glandular epithelium. When stromal cells become deciduous cells, in response to hormones and pregnancy, PEDF production is considered crucial to prevent (i) uncontrolled growth and penetration of the otherwise highly invasive trophoblastic cells of the placenta, into the uterine wall, and (ii) uncontrolled ingrowth of the blood vessels from the chorionic villi, into the uterine wall.

PEDF controls the cell cycle in many different cell types, by a direct effect on cell cycle control factors. The source of PEDF, namely the retinal pigment epithelium (RPE), may be crucial to the normal development and function of the neural retina. A variety of biologically active molecules, including growth factors, are synthesized and secreted by RPE cells. The RPE develops prior to and lies adjacent to the neural retina, and that it functions as part of the blood-retina barrier. In addition to growth factors, nutrients and metabolites are also exchanged between the RPE and the retina. For example, the RPE supplies to the retina the well-known growth factors PDGF, FGF, TGFα, and TGFβ. It is very likely that these and other unknown factors supplied by the RPE influence the organization, differentiation, and normal functioning of the retina.

In order to study and determine the effects of putative differentiation factors secreted by the RPE, cultured cells have been subjected to retinal extracts and conditioned medium obtained from cultures of human fetal RPE cells. For example, U.S. Pat. No. 4,996,159 discloses a neovascularization inhibitor recovered from RPE cells that is of a molecular weight of about 57,000±3,000. Similarly, U.S. Pat. Nos. 1,700,691, 4,477,435, and 4,670,257 disclose retinal extracts and the use of these extracts for cellular regeneration and treatment of ocular disease. Furthermore, U.S. Pat. Nos. 4,770,877 and 4,534,967 describe cell proliferation inhibitors purified from the posterior portion of bovine vitreous humor.

PEDF has been isolated from human RPE as a 50-kDa protein. Specifically, PEDF has been demonstrated to induce the differentiation of human Y79 retinoblastoma cells, which are a neoplastic counterpart of normal retinoblasts. The differentiative changes induced by PEDF include the extension of a complex meshwork of neurites, and expression of neuronal markers such as neuron-specific enolase and neurofilament proteins. This is why the synthesis and secretion of PEDF protein by the RPE is believed to influence the development and differentiation of the neural retina. Furthermore, PEDF is only highly expressed in undifferentiated human retinal cells, like Y79 retinoblastoma cells, but is either absent or down-regulated in their differentiated counterparts. It was also reported that PEDF mRNA is expressed in abundance in quiescent human fetal W1 fibroblast cells and not expressed in their senescent counterparts.

Further study of PEDF and examination of its potential therapeutic use in the treatment of inflammatory, vascular, degenerative, and dystrophic diseases of the retina and central nervous system (CNS) necessitates obtaining large quantities of PEDF. Unfortunately, the low abundance of PEDF in fetal human eye and, furthermore, the rare availability of its source tissue, especially in light of restrictions on the use of fetal tissue in research and therapeutic applications, make further study of PEDF difficult at best. Therefore, a recombinant technique was developed to procure a supply of the factor. See, U.S. Pat. No. 5,840,686.

Based upon the protein amino acid sequence, PEDF has been found to have extensive sequence homology with the serpin gene family, members of which are serine protease inhibitors. Many members of this family have a strictly conserved domain at the carboxyl terminus which serves as the reactive site of the protein. These proteins are thus thought to be derived from a common ancestral gene. However the developmental regulation differs greatly among members of the serpin gene family and many have deviated from the classical protease inhibitory activity. Becerra SP, Structure-function studies on PEDF. A noninhibitory serpin with neurotrophic activity. Although PEDF shares sequence homology with serpins, analysis of the cDNA sequence indicates that it lacks the conserved domain and thus may not function as a classical protease inhibitor.

Genomic sequencing and analysis of PEDF has provided sequences of introns and exons as well as approx. 4 kb of 5'-upstream sequence. The gene for PEDF has been localized to 17p13.1 using both in situ hybridization and analyses of somatic cell hybrid panels. This is very close to the p53 tumor suppressor gene as well as to the chromosomal localization of a number of hereditary cancers unrelated to mutations in the p53 gene product PEDF thus becomes a prime candidate gene for these cancers.

Although PEDF is particularly highly expressed by RPE cells, it is detectable in most tissues, cell types, tumors, etc. by Northern and Western blot analyses. It is readily detected, for example in vitreous and aqueous humors. The important question of subcellular localization of PEDF has also been addressed. Although the bulk of the PEDF appears to be secreted, PEDF is also associated with the nucleus as well as with very specific cytoskeletal structures in the cytoplasm. Importantly, this varies as to the age of the cells and the specific cell-cycle state. For example, the protein appears to concentrate at the tips of the pseudopods of primate RPE cells that interact with the substratum during the initial stages of attachment. Later though, this staining disappears and there is appearance of the protein in association with specific cytoskeletal structures and the nucleus. Thus it appears that PEDF plays an important intracellular role in both nucleus and cytoplasm.

There is PEDF expression in dividing, undifferentiated Y-79 cells and little or no expression in their quiescent, differentiated counterparts. The synthesis of PEDF in WI-38 fibroblast cells is restricted to the $G_0$ stage of the cell cycle in young cells. Moreover, in old senescent cells, PEDF messenger RNA is absent. In the retina, PEDF inhibits the Muller glial cells. Since Muller cells are similar to astroglia, PEDF would be similarly effective in blocking gliosis in conditions such as retinal detachment, diabetes, Retinitis Pigmentosa, etc. as well as sparing the lives of the retinal neurons. Thus, administration of GSH, to alter cellular redox potential, and thereby alter PEDF expression, may have particular value.

Apparently, in macular degeneration, the pigmented RPE cells become defective, and die, resulting in a functional loss of PEDF in the macula. Without the continuous presence of PEDF, vascular epithelial cells undergo a de-differentiation and enter into a proliferative stage, resulting in neovascularization, with invasion of the cornea in vitreous with blood vessels. The amount of inhibitory PEDF produced by retinal cells is positively correlated with oxygen concentration. Thus, PEDF is presumed to play a role in ischemia-driven retinal neovascularization. In fact, studies have shown that it is not necessary to kill the RPE cells to reduce PEDF availability. The availability of PEDF is sensitive to the redox potential of the cell, being more available in a reduced state and less available when the cell is in an oxidized state. (Ischemia is associated with a state in which cells produce an excess of free radicals. These may be due to exhaustion of antioxidants, cell death or apoptosis, or accumulation of toxic metabolic waste). This feedback regulation, which is applicable to other PEDF producing cells, thus induces vascularization where blood flow is needed (relatively oxidized redox potential) while maintaining an appropriate balance and allowing certain privileged tissues to remain unvascularized or with highly controlled vascularization. The oxidative control over PEDF is believed to be at the translative or post-translative levels, as mRNA levels are generally unchanged. It is noted that other classes of biologically active agents respond to redox state through transcriptional modification or sensitivity.

Efforts to directly administer PEDF, a peptide hormone, are met with difficulty, due to both the unavailability of bulk quantities of PEDF and difficulties in administration thereof.

Clinical Use of GSH

Ten elderly patients with normal glucose tolerance and ten elderly patients with impaired glucose tolerance (IGT) underwent GSH infusion, 10 mg/min for 120 min, for a total dose of 1,200 mg in 2 hr, under basal conditions and during 75 g oral glucose tolerance tests and intravenous glucose tolerance tests. Basal plasma total GSH levels were essentially the same for normal and IGT groups, and GSH infusion under basal conditions increased GSH to similar levels. This study demonstrated that GSH significantly potentiated glucose-induced insulin secretion in patients with IGT. No effect was seen on insulin clearance and action.

The antihypertensive effect of an i.v. bolus of 1,844 mg. or 3,688 mg. GSH was studied in normal and mild to moderate essential hypertensive subjects and in both hypertensive and non-hypertensive diabetics, both type I and type II. The administration of 1,844 mg. GSH produced a rapid and significant decrease in both systolic and diastolic blood pressure, within ten minutes, but which returned to baseline within 30 minutes, in both groups of hypertensive patients and in non-hypertensive diabetics, but had no effect in normal healthy subjects. At the 3,699 mg. dose, not only did the blood pressure decrease in the hypertensive subjects, but GSH produced a significant decrease in the blood pressure values in normal subjects as well. GSH, 1,200 mg/day intravenously administered to chronic renal failure patients on hemodialysis was found to significantly increase studied hematologic parameters (hematocrit, hemoglobin, blood count) as compared to baseline, and holds promise to reverse the anemia seen in these patients.

Toxicological Effects of GSH

The reported $LD_{50}$ of GSH in rats and mice via various routes of administration are listed in the table below. GSH has an extremely low toxicity, and oral $LD_{50}$ measurements are difficult to perform due to the sheer mass of GSH which has to be ingested by the animal in order to see any toxic effects.

Mouse data shows the following $LD_{50}$ for GSH: Oral 5,000 mg/kg (Modern Pharmaceuticals of Japan, IV Edition, Tokyo, Japan Pharmaceutical, Medical and Dental Supply Exporters' Association, 1972, p 93.); Intraperitoneal 4,020 mg/kg (Modern Pharmaceuticals of Japan, IV Edition, Tokyo, Japan Pharmaceutical, Medical and Dental Supply Exporters' Association, 1972, p 93.); Intraperitoneal 6,815 mg/kg (Toxicology, vol. 62, p. 205, 1990.); Subcutaneous 5,000 mg/kg (Modern Pharmaceuticals of Japan, IV Edition, Tokyo, Japan Pharmaceutical, Medical and Dental Supply Exporters' Association, 1972, p 93.); Intravenous 2,238 mg/kg (Japanese J. of Antibiotics, vol. 38, p. 137, 1985.); Intramuscular 4,000 mg/kg (Modern Pharmaceuticals of Japan, III Edition, Tokyo, Japan Pharmaceutical, Medical and Dental Supply Exporters' Association, 1968, p 97.). GSH can be toxic, especially in cases of ascorbate deficiency, and these effects may be demonstrated in, for example, ascorbate deficient guinea pigs given 3.75 mmol/kg daily (1,152 mg/kg daily) in three divided doses, whereas in non-ascorbate deficient animals, toxicity was not seen at this dose, but were seen at double this dose.

GSH impacts many aspects of the circulatory system, including interactions with nitric oxide signaling, ischemia, and control over vascular endothelium.

Use of High-Dose Oral GSH in Cancer Patients

In one published study, eight patients with hepatocellular carcinoma were treated with 5 g oral reduced GSH per day. Two patients withdrew shortly after receiving GSH due to intolerable side-effects (gastrointestinal irritation and sulfur odor). The remaining patients, aged 27-63, three male and three female, did not experience side-effects from this high dose of GSH and continued to take 5 g oral GSH for periods ranging from 119 days (at which time the patient died from her tumor) to >820 days (this patient was still alive at the time of publication and was still taking 5 g oral GSH daily; his tumor had not progressed and his general condition was good). Two of the female patients survived 1 year and exhibited regression or stagnation of their tumor growth. The remaining two patients, both male, died as expected within 6 months.

Experience in HIV-Infected Patients

A commercially available nutritional formulation containing 3 grams of reduced GSH was given daily to a group of 46 AIDS patients for a period of three months by a group of private physicians. No significant GSH-related adverse effects were reported. No evidence of toxicities from laboratory studies or from clinical examinations was reported; however, no benefit was conclusively demonstrated.

As apparent from the discussion above, there are a wide variety of pathologic and degenerative disorders which are impacted by either the level of GSH and/or ratio of oxidized to reduce species, or secondary influences based on said level or ratio. In general, it is believed that, within a pharmaceutically acceptable range, as determined by toxic ranges, increased levels of GSH tend to improve health, and low oxidized to reduced ratios are beneficial. Thus, the present invention advocates administration of reduced GSH for both healthy persons, which are all subject to aging and constant oxidative insult, and persons suffering from pathology as discussed above. As shown, GSH can itself be administered orally with good bioavailability, and therefore this mode of administration is preferred. It is, of course possible, to administer pharmaceutically acceptable derivatives of GSH or use other routes of administration. Likewise, GSH may be administered alone or in combination with an additive or synergistic composition, or to remediate toxicity of a co-administered agent.

There is supportive literature for the use of GSH, and other SH-antioxidants) demonstrating: (i) immediate radiation protection, safely; (ii) rapid inactivation of sulfur mustard gas, safely; (iii) immediate modification of the three exotoxins of anthrax, safely, such that the formation of either of the two heterotoxins becomes impossible and the toxins are muted, thereby preventing cell entry and the subsequent cytokines; (iv) rapid protection vs. Sepsis, as occurs with serious complications following smallpox vaccination, smallpox infection, burns and trauma, among others.

Thus, GSH is useful against a variety of nuclear, biological and chemical agents, and indeed its broad spectrum activity makes it particularly useful as a "first line" defense against unknown ill-defined threats. Its low toxicity also permits long term prophylactic use, during times of alert or imminent threat.

GSH is available in a formulation which renders this otherwise difficult molecule safe, stable, and bioavailable (80% is absorbed and intracellular in 1.5 hours following oral dosing) with dose responsive pharmacokinetics. In Phase 1 studies on non-symptomatic HIV positive people, the inherent safety of this naturally produced substance (10 grams/24 hours) was affirmed for the Anti Viral Division, of the FDA.

GSH is useful to combat and protect against unusual microbial agents, sepsis, anthrax toxins, small pox vaccination complications, smallpox, and genetically engineered smallpox carrying copies of the Interleukin 4 (IL-4) gene, (based on GSH suppression of the oxidative stress; GSH suppression of excess cytokine production; GSH suppression of the excess prostaglandin synthesis; GSH suppression of viral replication at the level of the proviral DNA integrated in host cells; GSH up-regulation of T helper 1 response patterns and down regulation of T helper 2 response patterns which includes IL-4). Sepsis kills more people than all the cancers of the lung, breast, prostate and colon, combined, and also results in extraordinary costs in the Intensive Care Units; biowarfare microbes, like smallpox, kill as a result of the Sepsis induced. GSH is also useful in the treatment of radiologic and chemical injuries, and as prophylaxis against prospective exposure.

GSH is also useful to treat prevalent neurologic disorders that are pharmaceutically underserved: Alzheimer's and Parkinson's.

GSH is useful for its properties of safely neutralizing poisonous chemicals, like sulfur mustard gas, and radioactive substances. The supporting literature also indicates that GSH has the ability to stem the lethal "cytokine storms" of rampant inflammation seen with anthrax toxins, smallpox vaccination complications, smallpox infections, and infections with Interleukin 4 (IL-4) enhanced smallpox and other "exotic microbes".

The preferred formulation and method of administering GSH, directly and rapidly replenishes the body's stores of bioprotectant, GSH. Cellular concentrations of this substance are vulnerable to erosion by many factors including age, diabetes, smoking, infections and exposures to toxins and radioactive compositions. It is essential to ensure that GSH levels are kept at high concentrations, in order to be protective, and to allow GSH to carry out its regulatory processes in cells . . . it is the most crucial biochemical in a cell . . . life processes cease rapidly without it. GSH can be deployed easily, to help protect military personnel and civilians from wartime and terrorist dispersions of poison gas, radioactive materials, and lethal microbes.

GSH levels can be restored and augmented, inside cells, starting approximately 30 minutes after oral administration. This is well within the "window of therapy" for most of the survivable exposures. The large safety factor of oral GSH, and the proven high acceptability of restorative/augmentive regimens (4 to 9 grams/day for 12 months) makes it possible to enhance and maintain high GSH levels, ahead of time, among first responders, and special military personnel on the ground. These available regimens appear to be sufficient since normal, prime production is 10 grams per 24 hours, in humans. There are no significant toxicities.

The drug is preferably provided as the stabilized, pharmaceutical GSH, in powder form, readily dissolvable in any convenient fluid. The taste is benign and citrus-like. Shelf life of the powder is 2.5 years. It is also available in a more costly, encapsulated dosage form.

The ease, safety and high acceptability of the regimen make it practical to treat radiation survivors at long term risk for cancer, on a continuous multi-year regimen. Cancer risks among such survivors is one of the major considerations in the aftermath of radiation exposures. GSH, aside from its immediate actions in neutralizing toxic free radicals caused by radiation, also is an essential cell regulator that helps control several classes of genes, including suppressing genes, such as the Ras family of oncogenes, that promote growth of cancer cells, and genes that promote growth of new blood vessels that cancers need for growth and spread. These long term properties of GSH are thought to help in decreasing the risks of cancer, and may offer synergistic approaches to the cancer treatment.

GSH is a major bioprotectant substance in cells. It combines with many chemicals that do not belong, and carries them out as excretory products, for example, sulfur mustard, or internalized uranium and plutonium. GSH is an integral part of the physiology of the Immune System; depletions of GSH impair this and permit fulminating infections. GSH stems the molecular pathology of anthrax and of Sepsis as seen in certain viral infections characterized by intense inflammation, such as smallpox. GSH turns on or off regulatory proteins and genes by setting the redox potential. GSH, in concert with specific enzymes (peroxidases and transferases), dismantles toxic fat molecules that have become peroxidized (rancid). This class of toxic substances causes inflammation and immune suppression. GSH destroys the hydrogen peroxide ($H_2O_2$) routinely formed in mitochondria, the cell "furnaces" that efficiently produce energy for cell functions. Without sufficient GSH the mitochondria become "executioners" and induce unscheduled apoptotic cell death in strategic cells by leaking cytochrome c and caspaces via SH-sensitive pores (permeability transition pores). This property of maintaining mitochondria is central in treating Parkinson's and Alzheimer's diseases. GSH inhibits the elaboration of excessive growth factors, and blood vessel growth factors found in cancers. GSH stems the activation of transcription factors, such as the NFκB's, that switch on disease-linked genes, as in inflammatory disorders, Sepsis, infections and cancers. Suppressing NFκB helps to curb the inflammation from sulfur mustard gas, anthrax, Sepsis, and smallpox. GSH is critical for phagocytic cells that are essential to clear away debris and microbes in tissues. High GSH levels in macrophages enhance local tissue defenses against microbes. This is a factor in the rationale for using GSH to combat microbes used in Biologic Warfare, and microbes causing Sepsis.

High GSH concentrations are needed during antigen processing by macrophages, dendritic cells and B type lymphocytes, to maintain a productive balance between the T helper 1 (Th1) and Th2, response patterns which are reciprocally related. GSH up-regulates Th1 and down regulates Th2 response patterns. This is relevant to decreasing the life threatening risks of smallpox immunization and of potential import in countering IL-4 enhanced viruses (e.g. IL-4 enhanced smallpox)

The GSH properties of setting the redox potential, dismantling lipid LOOH's, neutralizing ROS and RNS help to keep the family of NFκB transcription factors inactive, and out of the nucleus. The NFκB family of transcription factors activate several groups of genomic sequences, including proviral DNA sequences that have been incorporated in the infected host cells (e.g., HIV proviral DNA has been successfully studied in a number of peer-reviewed publications; it is likely that other, incorporated viral DNA sequences, like those of smallpox, may share a similar dependence on NFκB translocation into the nucleus and subsequent activation-binding to the proviral DNA).

GSH controls arachidonic acid metabolism and the products of the cyclo-oxygenases and lipoxygenases. These are pro-inflammatory, stimulate DNA synthesis and are also immunosuppressive. This why cyclo-oxygenase-2 inhibitors (e.g. Vioxx) are anti-inflammatory and also decrease cancer risks.

One aspect of the present invention provides a method for the treatment of smallpox infections. While smallpox is a terrifying scourge, having killed 500 million people in the 20th Century, the molecular pathologic mechanisms have been defined, and high dose GSH regimens pose a block vs. these mechanisms. The major organ involved in smallpox is the skin, with massive numbers of ulcerated pox lesions that may become secondarily infected. It is partially analogous to a patient with infected, third degree burns covering 80%-90% of the body, except smallpox is worse in that its inflammation assures the destruction of dermal GSH and GSH in macrophages and white blood cells. The basic pathology is analogous to that of Burns and Sepsis, but with added large numbers of circulating antigens, antigen antibody complexes, and cytokines. GSH levels in most cells are not measurable in severe Sepsis and Burns. The GSH losses are profound and well documented in the Burns and Sepsis literature. "Cytokine Storms" characterize some of the pathology, and it is feasible to down regulate inflammatory cytokine production by inactivating Nuclear Factor κB ("NFκB") with GSH. This works in inflammatory situations characterized by excess activation of NFκB.

GSH may also hinder the replication of the smallpox virus because GSH fosters the T helper 1 ("Th1") response patterns that include IL-12 and Interferon gamma (IFNγ) production . . . one of the body's most potent antivirals. GSH is known to up-regulate Th1 responses, which then reciprocally hinder Th2 responses, thereby hindering IL-4 production, a Th2 cytokine that can blunt IFNγ production, and foster unbridled viral replication.

Basically, high dose therapy of smallpox infection with Rx GSH may blunt the excess NFκB activation, which will decrease the production of the toxic, inflammatory cytokines. Also, Rx GSH can foster Th1 responses and up-regulate IFNγ production, a potent antiviral. When Th1 patterns are up-regulated, the reciprocal down-regulation of IL-4 is helpful, since IL-4 would otherwise interfere with IFNγ. Through NFκB, GSH is also likely to have anti-viral properties that would hinder replication of the smallpox virus, similar to how Rx GSH significantly inhibits HIV replication from its proviral DNA. Pox viruses have been genetically engineered with IL-4 genes in rodents, and possibly in smallpox strains as well. In animal models, IL-4 enhanced pox viruses have proven lethal, despite successful immunization vs. the particular, natural pox virus. Among the pathologic consequences of excess IL-4, by such "super pox" viruses, is the suppression of IFNγ. Rx GSH may be able to overcome this molecular pathology.

Another aspect of the present invention provides a method designed to help protect against the chemical, sulfur mustard gas, an inexpensive, easily prepared, dangerous substance that has been used in wars, and is thought to be a "favorite" of some terrorist groups. Accordingly, oral administration of GSH according to the present invention can restore and raise GSH levels inside cells, to safely help protect against this chemical. The blistering by this poison gas is not immediate, and its presence becomes obvious because of its odor. There is, therefore, time to orally administer GSH. It starts to raise cellular levels in 30 minutes, well within the "window of therapy".

A further aspect of the present invention provides a method for protection against radioactive dispersions. This has significant utility not only for Counterterrorism, but also in peacetime uses in the U.S. and in countries like Japan and France with their heavy reliance on nuclear power for energy generation. Accidents, contamination, and waste problems continuously expose people, in the U.S. and globally. In the case of significant radiation exposures, GSH can safely be used as a multi-year therapy to lower the risk of cancers, a major concern in radiation survivors.

A still further aspect of the present invention provides a method to help control anthrax infections and the dangerous, lingering effects of three toxins. These are three proteins and specific combinations of these must form chemically in order for the toxins to penetrate into cells wherein they cause the cell to produce prodigious amounts of injurious cytokines. GSH has the ability to prevent the formation of penetrating toxins, and it has the ability to slow down cytokine production through its gene suppressing functions. Patients can die even with appropriate use of doxycycline and ciprofloxacin, because of the exotoxins. GSH may help in this regard.

Because GSH is proven safe, and is a natural protectant produced by the body, it can be taken orally routinely, on a daily basis, to provide consistently high levels in all cells throughout the body; therefore, first responders and people in high risk situations can be continuously maintained at high GSH levels. There are no toxicities, and the majority of individuals using high doses report positive salutary effects. The health benefits of GSH are broad. Basically, there is no "downside" to having people become well-endowed with GSH.

It is well known from recent literature that GSH synthesis falls after 45 years of age. At all ages it can be destroyed by excess of alcohol, dietary fat, carbohydrates, tobacco, sun, and aerobics.

Alzheimer's Disease is believed to represent a gradual loss of brain cells by the process of apoptosis, a form of cell death wherein the cell breaks up into fragments. This process is believed to start with a depletion of GSH within the mitochondria, the "power plants" of cells. Some brain cells have several hundred mitochondria per cell because of their high energy requirements. If mitochondria are deficient in GSH, energy production fades, and in addition, the mitochondria release highly destructive biochemicals that initiate apoptosis. Medical scientists in this field believe effective, safe restoration of GSH in the brain could blunt the progression of Alzheimer's disease, particularly if detected and treated in the early stages.

Microvascular pathology has also been delineated in the Dementias, and contributes to perpetual, pathologic cycles. The microcirculation in the cerebrum of animal models was first defined with Scanning Electron Microscopy by H. B. Demopoulos and colleagues. Rx GSH counters this type of microvascular pathology by maintaining PGI2 synthesis in endothelium, and ensuring the desirable physiologic properties of vascular nitric oxide (.NO).

New methodologies that combine psychometrics (the ability of the patient to recite, verbatim, as much of a paragraph read to him/her, and other standardized short term memory tests) and brain imaging can detect early Alzheimer's and also chart the progression of this disorder.

These advances in modern Neurology make it feasible to conduct a clinical trial with early Alzheimer's patients, with placebo and treated groups, double blind, and randomized. It would be possible to follow the two groups and to compare the rates of progression to determine statistically significant differences. It is believed that GSH can intercede and slow or stop this process, and even allow a return of some function, in patients suffering from chronic dementias associated with progressive apoptosis of brain cells. Other chronic diseases associated with progressive apoptosis may also be treated with GSH. Likewise, GSH may be useful in treating or preventing acute events which lead to pathological apoptosis of cells in the brain and elsewhere. The preferred drug dosage form is safe, stable, is well absorbed (starting at 0.5 hours and reaching 70-80% within 1.5 hours) and readily distributed into cells.

Parkinson's Disease is a GSH depletion disorder that occurs in the specialized brain cells in the basal ganglia, ex., the Substantia Nigra. These cells produce a powerful neurotransmitter known as dopamine. The starting substance, DOPA, and the biochemical pathway leading to dopamine production are fraught with free radical reactions that use up considerable antioxidants, including ascorbic acid and GSH. While the initiating, etiologic agent(s) are not known, the supporting science indicates that the development and progression of the disorder involve inadequacies of GSH. According to the present invention, GSH levels are safely restored.

An important point for all GSH therapeutic programs is the fact that virtually all cells in the body, and especially brain cells, have active GSH transporters on their surface membranes that actively take up GSH from the surrounding tissue fluid and pump it into the cells, resulting in a major concentration increase inside the cells.

GSH is orally bioavailable, and efficiency may be increased by the administration of pharmaceutically stabilized reduced GSH in a bolus on an empty stomach. GSH is efficiently absorbed from mucous membranes, especially the sublingual mucosa and lumen of the duodenum and initial part of the ileum. GSH may be administered pharmacologically, to alter a redox state within the cells of an organism, and to therefore alter an expression of redox-dependent factors, such as NFκB and PEDF. Therefore, e.g., as a result of bioavailable administration of GSH (GSH), the redox balance of the tissues will be shifted toward the reduced state. This is especially the case in the event of tissues with a high or abnormally high metabolic demand, wherein a production of free radicals is excessive. In that case, the presence of pharmacologically administered reduced GSH will be expected to have an even greater impact in altering a redox balance in the cells. Thus, it is believed that the influence of exogenous GSH will be particularly seen in proximity to those tissues that are at risk of ischemia.

It is noted that GSH's effects are not limited to increasing or sustaining levels of PEDF, but rather the action of GSH may be exerted on many different tissues and cell functions. It is particularly noted that GSH regulated redox state may control cell function through gene induction, transcriptional, translational, posttranslational, or receptor-mediated effects, on a variety of factors.

In the case of PEDF, the administration of GSH would be expected to act as an antineoplastic therapy by (a) reducing neovascularization, (b) serving as an influence toward differentiated states of cells, and (c) supporting the normal function of tissues, such as neurons. It is particularly noted that, in this respect, the action of GSH as an antioxidant and free radical scavenger is believed to be distinct and separate.

In the case of NFκB, GSH administration would be expected to forestall the cascade which activates certain viral replication, including HIV.

GSH may also alleviate certain immune and autoimmune disorders, including rheumatoid arthritis, and alter glucocorticoid effects.

It is thought that transplantation of neurons (or their precursor cells) may cure or alleviate certain pathologies. For example, in Parkinson's disease, transplantation of specific fetal brain cells into patients could alleviate or cure certain problems associated with the disease. However, the transplanted cells would have to appropriately differentiate, and remain differentiated, in situ to functionally replace the pathological or dead cells. This involves creating and maintaining a microenvironment for the cells having the appropriate growth factors and stimuli. The maintenance of a high concentration of reduced GSH could promote, for example, the secretion of PEDF by the astroglia, or assist genetically modified (transfected) astroglia to produce high levels of PEDF, thus providing an environment rich in neural growth factors.

Ischemia Reperfusuion injury is also a particular concern in transplantation, and the pretreatment of the cells with relatively high levels of GSH may reduce the free radical damage to the cells as well as the levels of secondary redox messengers.

As used herein, the term "pharmaceutically stabilized GSH" refers to GSH which is maintained in a reduced form without substantial cyclization. This stabilization may be effected by the addition of one or more agents that, together with the GSH, provide a pharmaceutical formulation which is capable of delivering native reduced GSH.

The present invention also includes novel combinations of GSH and other pharmacological agents and in novel dosage forms and means for administration.

The oral administration of pharmaceutically stabilized reduced GSH, presented as a charge transfer complex in relatively high concentration may produce a significant, predictable increase in intracellular GSH levels in humans.

It has been found that, in otherwise healthy HIV infected humans, the intracellular GSH levels in the peripheral blood mononucleocytes (PBMs) was significantly increased after oral administration of stabilized GSH. This is achieved by providing a GSH formulation which ensures delivery of adequate dose of pharmaceutically stabilized, reduced GSH, with rapid dissolution before the duodenum. The formulation is administered to efficiently provide a high concentration of GSH in the duodenum, i.e., on an empty stomach, to enhance uptake.

A preferred formulation includes 250 mg. or more of reduced GSH with at least equimolar ascorbic acid, to fulfill three functions: acts as a sacrificial non-specific antioxidant during preparation, storage and after ingestion; reduces or neutralizes static electrical charge of GSH powder, allowing dense packing of capsules; and acts as a lubricant for the encapsulation device. The ascorbic acid also maintains an acidic and reducing environment, which pharmaceutically stabilizes the GSH molecule. Ascorbic acid is believed to form a charge couple with GSH which enhances penetration through cell membranes, and reduces the tendency for the gamma-glutamyl and glycinyl residues to assume a cyclic conformation or to form an internal cyclic amide. The ascorbate thus complexes with the GSH in solution to maintain a linear conformation. This linear conformation, in turn, stericly hinders the free cysteinyl thiol group. This steric hindrance stabilizes a free radical that may be formed, and thus maintains the biological activity of GSH.

A cyclic form of GSH, which may occur under certain conditions, such as neutral to basic pH, exposes the SH moiety, making it more reactive. Under alkaline pH, cyclic amide formation is promoted, leaving a potentially toxic compound. The cyclic GSH composition is a potential structural analog that may inhibit GSH reductase, GSH peroxidase and specific GSH transporter proteins.

Likewise, oxidizing conditions promote disulfide formation (GSSG and Pr—S—S-G), which may reduce bioavailability of GSH and counteract some of the potential benefits of GSH administration. Further, oxidizing conditions also promote desulfuration, resulting in ophthalmic acid formation (or other compounds), which may be toxic or inhibit efficient GSH absorption.

A preferred oral formulation thus preferably includes an effective amount of GSH mixed with a stabilizing agent, which is administered under such conditions that the concentration of GSH attained in the lumen of the latter portion of the duodenum is higher than the plasma GSH concentration, and preferably higher than the intercellular concentration of the epithelial lining cells. Thus, for example, a GSH and ascorbic acid capsule is taken on an empty stomach. The reducing agent, preferably ascorbic acid, prevents oxidation of the GSH during packaging and storage, and further may stabilize the GSH in the relatively alkaline conditions of the duodenum prior to absorption. Desulfuration of GSH leads to the formation of ophthalmic acid, the serine analog of GSH, which inhibits GSH uptake. This protocol is in contrast to prior art administration methods, which direct taking GSH capsules after meals. By diluting GSH with food, degradative enzymes are diluted and alkaline conditions buffered; however, the rapidity of absorption allows high bioavailability with only a small amount of degradation.

GSH may also be combined and another pharmaceutically active composition, wherein the other composition is selected from a broad group consisting of: easily oxidized compositions, antioxidant compositions, compositions with oxidant effects, compositions for the treatment of pathology associated with: suppressed total GSH levels, suppressed reduced GSH levels, relatively oxidized conditions in the organism, uncontrolled free radical or oxidizing reactions, or conditions where a more reduced state is desirable.

GSH may be used alone or in combination with other known compositions for the treatment or palliation of AIDS, HIV infection or retroviral replication (e.g., HTLV I, HTLV-II, HTLV-III, etc.), herpes virus replication (e.g., Herpes simplex type I, Herpes simplex type II, Herpes zoster (varicella), CMV, EBV, HHV-8, etc.), rabies, ebola virus, influenza virus, CHF, coronary artery disease, status post coronary artery restenosis, Diabetes mellitus, Macular Degeneration, and/or hepatitis (toxic or infectious). In addition, certain neurological conditions, such as amyotrophic lateral sclerosis, Parkinson's disease, Alzheimer's disease and others may also benefit from antioxidant therapies. Further, a number of pharmaceutical therapies, especially those that cross the blood brain barrier, are associated with side effects that relate to oxidative effects. Other drugs, such as Tamoxifen, are associated with macular degeneration. Thus, GSH may be administered to treat viral or certain bacterial infections, chronic diseases, detoxify drugs, treat or alleviate oxidative and lipid peroxidative disorders, and to reduce the long-term effects of oxidant agents, such as superoxide, which include carcinogenesis and aging.

It is noted that in the case of diseases which have as a part of their etiology a precipitation of proteins, such as amyloid diseases, e.g., Alzheimer's disease, the alteration of redox potential of the medium may have a dramatic effect on protein solubility. Thus, as the medium becomes more oxidized, the proteins will typically have more disulfide linkages, both defining the secondary structure of the peptide, and potentially forming cross linkages with other moieties. On the other hand, the administration of reduced GSH will result in a reducing environment, with correspondingly more free SH groups. Therefore, it is expected that administration of GSH will provide an effective treatment, or part of a treatment regimen, for such diseases. It is also noted that precipitated peptides may be involved in free radical reactions, which will also be countered by GSH administration.

GSH may also be used, alone or in combination with other therapies for the treatment of free radical associated neurological conditions, for example, Alzheimer's disease, Parkinson's disease, catecholamine toxicities, other free-radical associated toxicities, stroke and transient ischemic events, spinal chord injury and other traumatic injuries to nerve tissue, peripheral neuropathies, possibly prion-associated illness, infectious agent pathology and inflammatory pathology, or to reduce the free-radical associated toxicity of drugs administered to treat these conditions.

*Mycoplasma* infections, such as *mycoplasma* pneumonia, are believed to cause pathology due to free radical reactions within cells by these intracellular parasites. Therefore, GSH may be administered alone or in combination with an anti-*mycoplasma* antibiotic for the treatment of *mycoplasma* infections. GSH may also have benefit in the prophylaxis or treatment of pathology caused by cell-wall lacking or deficient organisms, such as *mycoplasma* or *mycoplasma*-like organisms, or L-form bacteria.

GSH may also be used to increase or supplement the GSH levels in normal mammals. This may be desired, for example, for prophylaxis against ischemic events, free radical damage from sun, chemicals, or other environmental exposure, and to reduce a cancer risk.

In fact, since oxidizing conditions in an organism are generally undesirable, and where necessary the mechanisms for producing oxidizing conditions typically overpower ingested antioxidants, a large number of medications and drugs are appropriate for combination with GSH. However, certain conditions may require care in the administration of GSH. Further, certain cancer chemotherapy regimens rely on exhaustion of cellular free radical quenching mechanisms to selectively kill target cells. Finally, cellular apoptosis, or programmed cell death, relies on exhaustion of reduced GSH levels in cells (mitochondria), resulting in death. Where this mechanism is required or physiologically correct, interruption by exogenous GSH may be undesirable. Further, GSH may interact with some compositions, either to non-specifically reduce or combine with the chemical moiety, or to alter a metabolism after ingestion; unless accounted for, these effects may be undesirable.

GSH may have efficacy in treatment of male infertility. Thus, glutathione may remedy mitochondrial defects or deficiency.

A known anti-HIV therapy, 3'-azidothymidine (Zidovudine®, AZT), acts as a potent reverse transcriptase inhibitor. This drug, however, generates free radicals and is toxic to mitochondria, and is associated with a myopathy. GSH may therefore be administered in conjunction with AZT to reduce toxicity while not interfering with the reverse transcriptase inhibitory activity, thus increasing the therapeutic index. Likewise, GSH may also be used to increase the therapeutic index of other drugs that have a significant free-radical associated toxicity.

There are a number of conditions which are believed to be associated with reduced intracellular antioxidant levels, including AIDS, diabetes, macular degeneration, congestive heart failure, vascular disease and coronary artery restenosis, Herpes virus infection, toxic and infectious hepatitis, and rabies. Certain interstitial lung disease may be due to insufficient GSH levels. Further, various toxins and medications may also result in free radical reactions, including types of cancer chemotherapy. Therefore, the administration of GSH holds potential to treat these diseases and conditions by the use of a convenient, effective oral formulation of GSH. Thus, the administration of exogenous GSH supplements the hepatic output to help maintain reduced conditions within the organism. As noted above, the failure to quench free radical reactions allows an undesirable cascade resulting in damage to macromolecules, lipid peroxidation, and generation of toxic compounds. The maintenance of adequate GSH levels is necessary to block these free radical reactions.

GSH also has the ability to form complexes with metals. For example, as discussed above, GSH forms chelation complexes with nickel, lead, cadmium, mercury, vanadium and manganese. GSH also forms circulating complexes with copper in the plasma. GSH may be administered to treat metal toxicity. It is believed that the GSH-metal complexes will be excreted, thus reducing the metal load. Thus, GSH may be administered for the treatment of toxicity associated with iron, copper, nickel, lead, cadmium, mercury, vanadium, manganese, cobalt, transuranic metals, such as plutonium, uranium, polonium, and the like. As compared to EDTA, GSH has a reduced tendency to chelate calcium, providing a significant advantage. It is noted that the chelation properties of GSH are separate from the antioxidant properties; however, some metal toxicities are free radical mediated, for example iron, and therefore GSH administration for these conditions is particularly advantageous.

In order to provide high bioavailability, it has been found desirable to provide a relatively high concentration of reduced GSH in proximity to the mucous membrane, e.g., the duodenum for oral administration. Thus, in contrast to prior methods, the GSH is preferably administered as a single bolus on an empty stomach. The preferred dosage is between about 100-10,000 mg. GSH, and more preferably between about 250-3,000 mg. GSH. Further, the GSH formulation is preferably stabilized with a reducing agent (antioxidant), preferably ascorbic acid, to reduce oxidation both during storage and in the digestive tract prior to absorption. The use of crystalline ascorbic acid has the added benefit of reducing the static charge of GSH for improved encapsulation and serving as a lubricant for the encapsulation apparatus. However, other static dissipation methods or additives may be employed, and other antioxidants may be employed. The preferred dosage form is a capsule, e.g., a two-part gelatin capsule, which protects the GSH from air and moisture, while dissolving quickly in the stomach.

The digestive tract is believed to have specific facilitated or active transport carriers for GSH, which allow uptake of GSH from the intestinal lumen without degradation. The uptake through this mechanism is maximized by providing a high concentration gradient and avoiding the presence or production of transport inhibitors, such as ophthalmic acid. Thus, the preferred method of oral administration employs an uptake mechanism that differs from GSH administered using prior methods, as well as most other thiol compounds.

The oral mucosa have been found to allow rapid and efficient uptake of GSH into the blood. In contrast to the digestive tract, the significance of facilitated or active transport mechanisms in the oral mucosa is believed to be low; rather, a high concentration of GSH in the oral mucosa is believed to permit passive transport of the GSH through the cells or around the cells into the capillary circulation. Therefore, compositions intended for absorption through the oral mucosa, e.g., for sublingual administration, are preferably of high purity, as contaminants may be absorbed similarly to GSH, and as relatively small, uncharged molecules. Therefore, the composition preferably includes ascorbic acid that helps to maintain the GSH in a reduced state, maintains a somewhat acidic environment in the mouth to avoid deprotonation of the glutamic acid residue, without causing substantially all of the amines to be protonated.

It has been found, contrary to reports of other scientists, that GSH is not substantially degraded in the stomach, and therefore, the release of the GSH need not diluted in the stomach or release be delayed. In fact, the GSH formulation is preferably released and dissolved in the stomach. The addition of stabilizer, i.e., ascorbic acid, further improves the ability of the GSH to reach its site of absorption in the intestine un-degraded. Once past the stomach, it is important that the GSH be immediately available for absorption, as the desulfurases and peptidases from the pancreas, as well as the increase in pH, do tend to degrade the GSH. The desulfurase produces ophthalmic acid, which interferes with GSH absorption. Thus, by providing a high concentration of GSH in the duodenum, without substantial dilution, the GSH may be absorbed at a maximum rate. While the degradation of GSH in the latter part of the duodenum and ileum may compete with the absorption process, the present method provides significant bioavailability. In fact, studies have demonstrated about 90% bioavailability of orally administered GSH.

The capsule is preferably a standard two-part hard gelatin capsule of double-O (OO) size, which may be obtained from a number of sources. After filling, the capsules are preferably stored under nitrogen, to reduce oxidation during storage. The capsules are preferably filled according to the method of U.S. Pat. No. 5,204,114, using crystalline ascorbic acid as both an antistatic agent and stabilizer. Further, each capsule preferably contains 500 mg of GSH and 250 mg of crystalline ascorbic acid. A preferred composition includes no other excipients or fillers; however, other compatible fillers or excipients may be added. While differing amounts and ratios of GSH and stabilizer may be used, these amounts are preferable because they fill a standard double-O capsule, and provide an effective stabilization and high dose. Further, the addition of calcium carbonate, a component of known high dose GSH capsules, is avoided as there may be impurities in this component. Further, calcium carbonate acts as a base, neutralizing stomach acid, which accelerates degradation of GSH in the small intestine.

Because the GSH and ascorbic acid are administered in relatively high doses, it is preferred that these components be highly purified, to eliminate impurities, toxins or other chemicals, which may destabilize the formulation or produce toxic effects or side effects. As stated above, the formulation may also include other pharmaceutical agents, of various classes.

GSH is advantageously administered over extended periods. Therefore, one set of preferred useful combinations include GSH and drugs intended to treat chronic conditions which are well absorbed on an empty stomach, and do not have adverse interactions or reduced or variable combined absorption.

One particular class of drugs includes central or peripheral adrenergic or catecholenergic agonists, or reuptake blockers, which may produce a number of toxic effects, including neurotoxicity, cardiomyopathy and other organ damage. These drugs are used, for example, as cardiac, circulatory and pulmonary medications, anesthetics and psychotropic/antipsychotic agents. Some of these drugs also have abuse potential, as stimulants, hallucinogens, and other types of psychomimetics. Other free radical initiation associated drugs include thorazine, tricyclic antidepressants, quinolone antibiotics, benzodiazepines, acetaminophen and alcohol.

An oral pharmaceutical formulation may be made comprising GSH in an amount of between about 50 mg-10 gm, and an effective amount of a pharmacological agent capable of initiating free radical reactions in a mammal. The pharmacological agent is, for example, an adrenergic, dopaminergic, serotonergic, histaminergic, cholinergic, gabaergic, psychomimetic, quinone, quinolone, tricyclic, and/or steroid agent.

Hepatic GSH is consumed in the metabolism, catabolism and/or excretion of a number of agents. The depletion of hepatic GSH may result in hepatic damage or a toxic hepatitis. Such agents may include, for example, aminoglycoside antibiotics, acetaminophen, morphine and other opiates. High dose niacin, used to treat hypercholesterolemia, has also been associated with a toxic hepatitis. An oral pharmaceutical formulation may be provided comprising GSH in an amount of between about 50-10,000 mg, administered in conjunction with and an effective amount of a pharmacological agent that consumes hepatic GSH reserves.

A number of pathological conditions result in hepatic damage. This damage, in turn, reduces the hepatic reserves of GSH and the ability of the liver to convert oxidized GSH to its reduced form. Other pathological conditions are associated with impaired GSH metabolism. These conditions include both infectious and toxic hepatitis, cirrhosis, hepatic primary and metastatic carcinomas, traumatic and iatrogenic hepatic damage or resection. A pharmaceutical formulation may be provided comprising GSH and an antiviral or antineoplastic agent. The antiviral or antineoplastic agent is, for example, a nucleoside analog.

GSH is broken down, and cysteine excreted, possibly in the urine. Very high doses of GSH may therefore result in cysteinuria, which may result in cysteine stones. Other long term toxicity or adverse actions may result. Therefore, a daily intake of greater than about 10 gm. for extended period should be medically monitored. On the other hand, individual doses below about 50 mg. are insufficient to raise the concentration of the duodenal lumen to high levels to produce high levels of absorption, and to provide clinical benefit. Therefore, the preferred formulations have GSH content greater than 50 mg, and provided in one or more doses totaling up to about 10,000 mg per day.

In the treatment of HIV infection, it is believed that the oral administration of a relatively high dose bolus of GSH, i.e., 1-3 grams per day, on an empty stomach, will have two beneficial effects. First, HIV infection is associated with a reduction in intracellular GSH levels in PBMs, lung, and other tissues. It is further believed that by increasing the intracellular GSH levels, the functioning of these cells may be returned to normal. Therefore, the administration of GSH will treat the effects of HIV infection. Therefore, GSH and ascorbic acid may be provided in an oral formulation, optionally in combination with an antiretroviral agent. It is noted that the transcription mechanisms and control involved in retroviral infection is believed to be relatively conserved between various types. Therefore, late stage retroviral suppression is expected for the various types of human retroviruses and analogous animal retroviruses.

Second, it has been found in in vitro tests that by increasing the intracellular levels of GSH in infected monocytes to the high end of the normal range, the production of HIV from these cells may be suppressed for about 35 days. This is believed to be related to the interference in activation of cellular transcription by cytokines, including NFκB and TNFα. Therefore, the infectivity of HIV infected persons may be reduced, helping to prevent transmission. This reduction in viral load may also allow the continued existence of uninfected but susceptible cells in the body.

GSH, administered according to the present method, is believed to be effective in the treatment of congestive heart failure (CHF). In CHF, there are believed to be two defects. First, the heart muscle is weakened, causing enlargement of the heart. Second, peripheral vasospasm is believed to be present, causing increased peripheral resistance. GSH is effective in enhancing the effects of nitric oxide, and therefore is believed to be of benefit to these patients by decreasing vasoconstriction and peripheral vascular resistance, while increasing blood flow to the tissues. While nitroso-GSH is more effective at preventing platelet aggregation than at vasodilation, it is nevertheless a potent vasodilator with a longer half-life than nitric oxide alone. Further, since a relative hypoxia of the tissues is associated with free radical-mediated cellular damage, the presence of GSH will also help to block this damage. GSH may be orally administered in conjunction with a congestive heart failure medication, for example, digitalis glycosides, dopamine, methyldopa, phenoxybenzamine, dobutamine, terbutaline, amrinone, isoproterenol, beta blockers, calcium channel blockers, such as verapamil, propranolol, nadolol, timolol, pindolol, alprenolol, oxprenolol, sotalol, metoprolol, atenolol, acebutolol, bevantolol, tolamolol, labetalol, diltiazem, dipyridamole, bretylium, phenytoin, quinidine, clonidine, procainamide, acecainide, amiodarone, disopyramide, encainide, flecanide, lorcainide, mexiletine, tocainide, captopril, minoxodil, nifedipine, albuterol, pargyline, vasodilators, including nitroprusside, nitroglycerin, phentolamine, phenoxybenzamine, hydrazaline, prazosin, trimazosin, tolazoline, trimazosin, isosorbide dinitrate, erythrityl tetranitrate, asprin, papaverine, cyclandelate, isoxsuprine, niacin, nicotinyl alcohol, nylidrin, diuretics, including furosemide, ethacrynic acid, spironolactone, triamterine, amiloride, thiazides, bumetanide, caffeine, theophylline, nicotine, captopril, salalasin, and potassium salts.

It has been found that elevated levels of homocysteine as a significant risk in vascular disease, such as atherosclerosis, venous thrombosis, heart attack and stroke, as well as neural tube defects and neoplasia. Homocysteine promotes free radical reactions. In patients with defective homocysteine metabolism, relatively high levels of homocysteine are present in the blood. GSH may be administered to patients with elevated homocysteine levels.

It was believed that, because hepatocytes produce reduced GSH through a feedback-inhibited pathway, hepatocytes would not effectively absorb reduced GSH from the plasma. Therefore, an insult to hepatocytes, for example from toxic or infectious origin, which otherwise suppressed GSH production, would result in cellular damage or death. In fact, the present inventors believe that this is not the case, at least in the case of compromised hepatocytes. Therefore, hepatitis, of various types, may be treated with orally administered GSH. For example, both alcohol and acetaminophen are both hepatotoxic, and result in reduced hepatocyte GSH levels. Therefore, these toxicities may be treated with GSH. GSH may also be effective in the treatment of other types of toxicities, to various cells or organs, which result in free radical damage to cells or reduced GSH levels. Hepatitis may also have viral etiology, and the use of GSH may be beneficial in a similar manner to the use of GSH in the treatment of management of HIV infection. The GSH may act to reduce expression of viral genes, as well as reduce the oxidative challenge resulting from active viral replication. GSH may also reduce viral disulfide bonds, reducing viral infectivity.

Diabetes, especially uncontrolled diabetes, results in glycosylation of various enzymes and proteins, which may impair their function or control. In particular, the enzymes which produce reduced GSH (e.g., GSH reductase) become glycosylated and non-functional. Therefore, diabetes is associated with reduced GSH levels, and in fact, many of the secondary symptoms of diabetes may be attributed to GSH metabolism defects. GSH may therefore be applied to supplement diabetic patients in order to prevent the major secondary pathology. An oral pharmaceutical formulation comprising GSH and an anti-hyperglycemic agent may also be administered to a patient in need of such treatment.

GSH, due to its strong reducing potential, breaks disulfide bonds. It is believed that most normal proteins are not denatured, to a great extent, by normal or superphysiologic levels of GSH. It is believed, however, that opiate receptors are deactivated by high normal levels of GSH. It is therefore believed that GSH administration may be of benefit for the treatment of obesity and/or eating disorders, other addictive or compulsive disorders, including tobacco (nicotine) and opiate additions.

GSH may be administered in conjunction with nicotine. The physiologic effects of nicotine are well known. GSH, due to its vasodilatory effects, improves cerebral blood flow, resulting in a synergistic cerebral function-enhancing effect.

In mammals, the levels of GSH in the plasma are relatively low, in the micromolar range, while intracellular levels are typically in the millimolar range. Therefore, the intracellular cytosol proteins are subjected to vastly higher concentrations of GSH than extracellular proteins. The endoplasmic reticulum, a cellular organelle, is involved in processing proteins for export from the cell. It has been found that the endoplasmic reticulum forms a separate cellular compartment from the cytosol, having a relatively oxidized state as compared to the cytosol, and thereby promoting the formation of disulfide links in proteins, which are often necessary for normal activity. In a number of pathological states, cells may be induced to produce proteins for export from the cells, and the progression of the pathology interrupted by interference with the production and export of these proteins. For example, many viral infections rely on cellular production of viral proteins for infectivity. Interruption of the production of these proteins will interfere with infectivity. Likewise, certain conditions involve specific cell-surface receptors, which must be present and functional. In both these cases, cells that are induced to produce these proteins will deplete reduced GSH in the endoplasmic reticulum. It is noted that cells that consume GSH will tend to absorb GSH from the plasma, and may be limited by the amounts present. Therefore, by increasing plasma GSH levels, even transiently, the reducing conditions in the endoplasmic reticulum may be interfered with, and the protein production blocked. Normal cells may also be subjected to some interference; however, in viral infected cells, or cells abnormally stimulated, the normal regulatory mechanisms may not be intact, and the redox conditions in the endoplasmic reticulum controlled by the availability of extracellular GSH. In these conditions, the pharmaceutical administration of GSH may produce significant effects.

Reproduction of herpes viruses, which are DNA viruses, is inhibited or reduced in cell culture by the administration of extracellular GSH. Herpes virus infections may be treated by administering GSH. The known herpes viruses include herpes simplex virus I, herpes simplex virus II, herpes zoster, cytomegalovirus, Epstein Barr virus, as well as a number of other known viruses.

It is also believed that infection by the rabies virus, an RNA virus, may be treated by the administration of GSH. While standard treatments are available, and indeed effective when timely administered, GSH may be useful in certain circumstances. Therefore, rabies virus infection may be treated, at least in part. One available treatment for rabies is an immune serum. GSH may be parenterally administered in combination with an antibody, such as a monoclonal antibody, humanized antibody, or donor antibodies derived from human or animal sources. GSH may also be administered separately.

Coronary heart disease risk is increased by the consumption of a high-fat diet, and reduced by the intake of antioxidant vitamins, including vitamin E and vitamin C, as well as flavonoids. High fat meals impair the endothelial function through oxidative stress, resulting in impaired nitric oxide availability. It has been found that vitamin C and vitamin E restores the vasoconstriction resulting from nitric oxide production by endothelium after a high fat meal. GSH may be administered as a prophylaxis against vascular disease.

In utilizing antioxidants as advanced therapeutic approaches, the following principles have been developed over time: Different disorders generate different types of free radicals, in different environments. Therefore, different specific antioxidants are needed for these various radicals and related compounds. The commonest species and related molecules includes superoxide, $.O_2—$; hydroxyl, .OH; peroxy, .OOH; hydrogen peroxide, $H_2O_2$ (splitting into hydroxyl radicals); alkoxy, RO.; delta singlet oxygen, $^1O_2$; nitric oxide, .NO; lipid hydroperoxides, LOOH (splitting into alkoxy and hydroxyl radicals). See, Montagnier, Luc, Olivier, Rene, Pasquier, Catherine (Eds.), Oxidative Stress in Cancer, AIDS, and Neurodegenerative Diseases, Marcel Dekker, NY (1998).

In addition to qualitative differences among several species of free radicals, their rates of formation will differ, as will the different types of inciting agents that may have to be simultaneously controlled. For example, continued, unprotected exposures of the eyes, in Macular Degeneration, to strong sunlight and to tobacco smoke, would limit benefits from an antioxidant used as a therapeutic agent for control of this disease. Synergistic therapies may be provided to patients by increasing antioxidant levels systemically or in specific organs as well as reducing oxidative, free radical generating and ionizing influences. In this case, GSH therapy would be complemented with ultraviolet blocking sunglasses, and a tobacco smoking cessation plan, if necessary. A particularly advantageous antioxidant for combination with GSH is alpha tocopherol succinate.

Free radicals occur in different parts or subparts of tissues and cells, with different inciting agents. For example, in trauma to the brain or spinal cord, the injurious free radicals are in the fatty (lipid) coverings that insulate nerve fibers, the myelin sheaths. Extremely high doses of a synthetic corticosteroid, 5 to 10 grams of methyl prednisolone sodium succinate (MPSS), given for just 24 hours, rapidly reach the brain and spinal cord and diffuse rapidly into the myelin, neutralizing the trauma-induced radicals, specifically: .OH, .OOH, and RO.. A pharmaceutical composition may be provided comprising a combination of GSH and a glucocorticoid agent.

TRX has been shown to modulate the signaling processes of programmed cell death (apoptosis). TRX and other thiol compounds exert a protective activity against cytotoxicity and apoptosis induced by various oxidative stresses. For example, Fas and TNF-α dependent cell death may be protected by intracellular as well as extracellular TRX. The activity of the ICE (interleukin 1b-converting enzyme) family proteases (caspases), with cysteine residue in their active site, which are involved in apoptosis, are regulated by a redox mechanism. For example, the activity of caspase-3 (CPP32), an important member of caspases, is markedly inhibited by oxidizing agents, which is counteracted by dithiothreitol or TRX. In contrast, on exposure to diamide or hydrogen peroxide, a marked increase of CPP32 protease activity was observed after a few hours, suggesting that intracellular redox state profoundly modulates the signaling processes of apoptosis by regulating the activity of caspases. Many transcription factors and DNA-binding proteins are redox regulated by TRX, including NFκB, AP-1, PEBP2/AML-1, and p53. Junji Yodoil, Shugo Ueda, Masaya Ueno, Tetsuro Sasada, and Hiroshi Masutani, Redox control of Thioredoxin (TRX) on the cytotoxic/death signal.

Superoxide ($O_2^-$) is the compound obtained when oxygen is reduced by one electron. Oxidants related to superoxide include $H_2O_2$ and alkyl peroxides, hydroxyl radical and other reactive oxidizing radicals, oxidized halogens and halamines, singlet oxygen, and peroxynitrite. These molecules are thought to participate in the pathogenesis of a number of common diseases, including among others malignancy, by their ability to mutate the genome, and atherosclerosis, by their capacity for oxidizing lipoproteins. Oxidizing agents are, however, are physiologically important for host defense, where they serve as microbicidal and parasiticidal agents, in normal apoptosis, or programmed cell death, and in biological signaling, where their liberation in small quantities results in redox-mediated changes in the functions of enzymes and other proteins. It is generally believed that host defense mechanisms are mediated by such strong effects that pharmacological antioxidants would not be able to overcome the powerful oxidant effects. On the other hand, it is believed that antioxidant pharmaceuticals may play an important role in modulating redox-mediated signaling and early steps in biological cascades, such as apoptosis.

The accepted, published, peer-reviewed literature has repeatedly demonstrated the multiple properties of GSH in the body. The abundant physiological and biochemical properties of GSH led others into an extensive series of clinical trials wherein precursors of GSH were administered, because the prevailing belief was that GSH itself could not be effectively absorbed if it was simply given as GSH. Hence, the popularity of the relatively ineffective and potentially damaging GSH precursor N-acetyl cysteine (NAC) is currently being misused in the homosexual (high AIDS risk) community. The further belief was that GSH would not cross the membranes of lymphocytes and other cells, whereas NAC could. The view was that to try to correct the GSH deficiency in HIV/AIDS, with GSH itself, was a hopeless task, because it would be degraded before uptake across membranes. However, the precursors of GSH have failed to raise intracellular GSH levels. A suitable regimen for oral administration of GSH to achieve high bioavailability and increased intracellular levels of GSH is provided.

While prior studies have employed GSH dissolved in orange juice to administer GSH to AIDS patients, resulting in GSH uptake, this method does not provide the advantages of an encapsulated or pill form, and there was no recognition for the need to prevent digestive dilution or GSH derived impurities from being present.

GSH has also proven to be an effective anti-viral agent and interferes with HIV replication at a critical site that is not affected by other current drugs, viral mRNA transcription. GSH keeps viral DNA quiescent, especially when potent activators are present, like NFκB, and TNF-α. GSH's anti-viral target appears to be at a point where the virus can not readily mutate. The dependence of HIV replication on binding activated NFκB onto its Long Terminal Repeat (LTR) appears to be central to the virus.

Orally administered GSH can safely raise cell levels beyond correcting GSH deficiencies. A number of pathologic processes can be inhibited by these higher levels, for example, curtailing the virtually self-perpetuating, powerful biochemical cycles producing corrosive free radicals and toxic cytokines that are largely responsible for the signs and symptoms of AIDS. These biochemical cycles destroy considerable quantities of GSH but they can eventually be brought under control, and normalized with sufficient, ongoing GSH therapy. A typical example is the over production of a substance, 15 HPETE (15-hydroperoxy eicosatetraenoic acid), from activated macrophages. The 15 HPETE is a destructive, immunosuppressing substance and requires GSH for conversion into a non-destructive, benign molecule. The problem is that once macrophages are activated, they're difficult to normalize.

Once inside cells, GSH curtails the production of free radicals and cytokines, corrects the dysfunctions of lymphocytes and of macrophages, reinforces defender cells in the lungs and other organs, halts HIV replication in all major infected cell types, by preventing the activation of the viral DNA by precluding the activation of NFκB, inhibits the TAT gene product of HIV that drives viral replication, dismantles the gp120 proteins of the virus coat. These gp120 proteins are the projections of the virus that normally allow it to lock onto susceptible CD4+ cells thereby helping the spread of the virus to uninfected CD4+ cells. By disrupting the gp120 protein, GSH offers a potential mode of preventing transmission not only to other cells in the patient, but perhaps in precluding transmission to others.

Besides classic antiviral or antiretroviral agents (reverse transcriptase inhibitors, protease inhibitors), a number of other therapies may be of benefit for AIDS patients, for example combinations of GSH with the following drugs: cyclosporin A, thalidomide, pentoxifylline, selenium, desferroxamine, 2L-oxothiazolidine, 2L-oxothiazolidine-4-carboxylate, diethyldithiocarbamate (DDTC), BHA, nordihydroguairetic acid (NDGA), glucarate, EDTA, R-PIA, α-lipoic acid, quercetin, tannic acid, 2'-hydroxychalcone, 2-hydroxychalcone, flavones, α-angelicalactone, fraxetin, curcurmin, probucol, and arcanut (areca catechul).

Inflammatory responses are accompanied by large oxidative bursts, resulting in large numbers of free radicals. Therefore, GSH may have application in the therapy for inflammatory diseases. GSH may advantageously reduce the primary insult a well as undesired aspects of the secondary response. GSH may be administered to patients suffering from an inflammatory disease process, such as arthritis, inflammatory bowel disease, etc. Combination pharmaceutical therapy may be provided including GSH and an analgesic or antiinflammatory agent, for example opiate agonists, glucocorticoids or non-steroidal antiinflammatory drugs (NSAIDS), including opium narcotics, meperidine, propoxyphene, nalbuphine, pentazocine, buprenorphine, asprin, indomethacin, diflunisal, acetominophen, ibuprofen, naproxen, fenoprofen, piroxicam, sulindac, tolmetin, meclofenamate, zomepirac, penicillamine, phenylbutazone, oxyphenbutazone, chloroquine, hydroxychloroquine, azathiaprine, cyclophosphamide, levamisole, prednisone, prednisolone, betamethasone, triamcinolone, and methylprednisolone.

GSH may also hold benefit for the treatment of parotitis, cervical dysplasia, Alzheimer's disease, Parkinson's disease, aminoquinoline toxicity, gentamycin toxicity, puromycin toxicity, aminoglycoside nephrotoxicity, paracetamol, acetaminophen and phenacetin toxicity.

GSH need not be orally ingested in order to provide the beneficial effects noted. While the drug may be administered intravenously or parenterally, it may also be administered through mucous membranes, including sublingually, as a vaginal or rectal suppository, and by pulmonary inhaler, for topical applications to the alveolar surface cells of the lungs to enhance pulmonary protection against unusual pneumonias. Systemic administration of GSH may be used to concentrate GSH in lymph nodes, and lymphoid tissues.

GSH tends to be unstable in solution. Therefore, a pharmaceutical administration apparatus is provided having a dual chamber distribution pouch, having a frangible interconnection, allowing mixing between an aqueous phase and a dry GSH preparation. The aqueous phase may be, for example, a gel, cream or foam. Either pouch may also contain another pharmaceutical agent, as described above.

A GSH administration appliance may be used for delivering an effective dose of GSH to an accessible mucous membrane, such as the oral, vaginal, urethral or anal cavities. A dry GSH preparation, for example in a dehydrated gel, matrix or polymer, having a high surface area per unit volume ratio, is provided in a foil bag or pouch. The dehydrated mass includes GSH, as well as an optional stabilizing agent, such as ascorbic acid. The dehydrated mass is hydrated by the mucosal membrane or by an externally applied fluid, and the GSH is then present to protect the mucous membrane from viral infection.

The ability of GSH to chemically dismantle the gp120 protein of HIV by chemically destroying structural disulfide bonds, indicates that transmission of the infection may be curtailed to some extent. If gp120 is dismantled, the virus cannot lock onto CD4+ cells. The oral GSH treatment of patients may suffice to dismantle gp120 of viruses from treated patients. The topical applications of GSH to mucous membranes might possibly serve to protect a sex partner if unsafe sexual practices occur.

Another effect is seen when GSH or nitroso-GSH is placed in the male urethra. In this case, the GSH or GSH derivative is absorbed. The vasodilatory effects of nitroso-GSH, which is formed by interaction of GSH with nitric oxide or provided directly, vasodilates the penis, resulting in an erection. Thus, a urethral GSH or nitroso-GSH suppository has potential for the treatment of impotence. GSH or nitroso-GSH may also be used to treat female sexual dysfunction. Direct application of GSH or nitroso-GSH to the mucous membranes, for example, as a cream or in a gel formulation, will result in local vasodilation, lubrication, and engorgement of erectile tissue.

It is noted that the effects of various pharmacological agents which act to increase the production of nitric oxide, for example the substrate for formation of nitric oxide, the amino acid arginine, the stability of nitric oxide in the blood, or the effect of nitric oxide, may be used synergistically. Likewise, drugs which act on differing systems, such as the central nervous system and peripheral vascular system, may also be used synergistically. Thus, GSH may be used alone or in combination to achieve its effects on the circulatory system and vascular tissues.

GSH or a GSH derivative may also be co-administered with yohimbine, an alpha-2 receptor blocker, providing a synergistic effect. Yohimbine has been established to treat male sexual dysfunction, (e.g., impotence), among other effects. Apomorphine may also provide synergistic effects with GSH for the treatment of impotence. It is noted that, in many cases, female sexual dysfunction may be related to pelvic and genital vascular response, in particular vasodilation, and therefore GSH, alone or in combination with other vasoactive or neuroactive substances, may be beneficial in the treatment of both male and female sexual dysfunction.

GSH may be administered to mucous membranes in the form of a liquid, gel, cream, jelly, absorbed into a pad or sponge. Administration may also be provided by a powder or suspension.

The effective delivery of intact, pharmaceutically stabilized, bioavailable reduced L-GSH has been accomplished. By providing high-dose GSH for the body's general use, diabetics having either form of the disease may be provided with ample supplies of GSH. Correcting the GSH deficiency and also raising the levels inside cells to the upper range of normal will help to delay, or prevent the complications of diabetes.

GSH, orally administered, in moderately high doses, one to five gm/day, may be able to affect the outcome of macular degeneration. The avidity with which the RPE cells take up GSH indicates that they may have a critical role in ameliorating this disorder. Unlike rods and cones, RPE cells can divide and replenish themselves if allowed. If caught at an early stage, before significant losses of rods and cones, the condition may be halted and delayed.

Since GSH is relatively non-toxic, it may be used liberally for its advantageous properties. GSH may be added to a viral contaminated fluid or potentially contaminated fluid to inactivate the virus. This occurs, for example, by reduction of critical viral proteins. GSH may be added to blood or blood components prior to transfusion. The added GSH is in the reduced form, and is added in a concentration of the lower of about 100 mM-500 mM or to a solubility limit, and more preferably in a concentration of about 10-50 mM. The addition of GSH to whole blood, packed red blood cells or other formed blood components (white blood cells, platelets) may be used to increase the shelf life and/or quality of the cells or formed components.

It is also noted that other pharmacological agents may be employed to achieve alterations in redox balance or to acts free radical scavenging agents. These may be employed individually or in combination. For example, GSH may also be administered in conjunction with other antioxidants or redox-active drugs; a preferred formulation for oral administration of GSH includes ascorbic acid (Vitamin C). Other acceptable agents for administration include $\alpha$-tocopherol, either in the free state as an antioxidant or as a pharmaceutically acceptable ester thereof as a Vitamin E precursor. In addition, $\alpha$-lipoic acid is believed to be a nontoxic, orally bioavailable and effective antioxidant. GSH is a most preferred agent due to its central role in maintaining cell oxidative balance, ubiquity in the body, and high therapeutic index. One traditional difficulty, obtaining high oral bioavailability for GSH, has been solved.

The inventors have developed and has successfully clinically tested a safe, stabilized, orally bioavailable formulation of GSH. This achievement had not been thought to be possible because: a high density of molecular charges precluded trans membrane transport; the thiol group is at some risk, and if there is extended oxidation, desulfuration may occur, with the consequent formation of ophthalmic acid, a toxic structural analogue that blocks mitochondrial GSH transporters; a commonly believed view held that the two amino peptide bonds would be hydrolyzed immediately by gastric acid, and/or the gastric and pancreatic proteases.

The preferred formulation and protocol for administration of GSH: dissipates the high density of molecular charges, without altering the structure or chemical properties of GSH; the thiol group was chemically stabilized, with no evidence of oxidative desulfuration during manufacture, storage, or in patient use at prolonged, high doses of 0-75 mg/kg, per day, divided into two equally divided doses; gastric acid in the human stomach is incapable of hydrolyzing the amino peptide bonds because such hydrolysis requires 6N HCl, and a temperature of 110° C. for 18 hours; the GSH formulation withstood acid degradation for 23 hours at pH 1.2; the proteases encountered by GSH in the stomach and in the duodenum do not attack these two amino peptide bonds; this type of information has served initial amino acid sequence efforts of proteins in the past: for example, trypsin hydrolyzes the carboxyl side of arginine and lysine residues; chymotrypsin is selective for the carboxyl side of the aromatic chains of tyrosine, tryptophane and phenylalanine; carboxypeptidase A hydrolyzes carboxyl terminals if the residue has an aromatic or bulky, aliphatic side chain; GSH is absorbed, intact, as a tripeptide over a short segment of upper jejunum, starting approximately at the Ligament of Treitze; however, further down in the small intestine, the non-specific endopeptidases do hydrolyze GSH into its three components.

Early clinical trials determined the pharmacokinetics of absorption and intracellular distribution in Peripheral Blood Mononuclear Cells in asymptomatic HIV (+) patients, using three doses of 1 gm, 2 gms and 3 gms/day over a 4 week period, with two weeks of baselines, plus two weeks of post drug exposure. Approximately 400 GSH assays were carried out on each patient, including 24-hour urine samples.

A total of 10,000 GSH assays were performed. The independent analyses demonstrated a dose response relationship. The GSH was absorbed and distributed within the PBMC, starting at 30 minutes after ingestion, and completed in 60 minutes. This study demonstrated safety, and good patient acceptance, with no evidence of toxicities.

A clinical study on far advanced AIDS patients who had exhausted the HAART combinations and averaged 300,000 copies (HIV RNA PCR) and 50 CD4+ cells/per cubic mm. The small group consumed 75 mg/kg in two equally divided doses for 3.0 years. Survival for the four who followed the regimen extended for 3 years after starting on GSH. Two individuals who started the regimen at approximately the same time as the four, but who dropped out, succumbed within 6 months. The four patients illustrated did not restore their CD4+ cell counts to any extent. GSH compliance began to fail between the second and third years. The Phase I/II data, was based on approximately 10,000 GSH assays of peripheral blood mononuclear cells (PBMC's) of HIV positive people given the drug regimen. A dose response relationship was demonstrated, and correction of the intracellular GSH insufficiency was evident.

It is therefore an object of the technology to provide an effective therapy for humans and animals which are deficient in GSH, or suffer from a disease or condition that consumes GSH. The therapy preferably includes oral administration of orally bioavailable GSH. The GSH is preferably administered on an empty stomach as a bolus, to generate a high intragastric glutathione concentration, which is then dumped into the duodenum, and then passes to the jejunum, where it is efficiently absorbed. The GSH is preferably in reduced form, as part of a charge transfer complex with ascorbic acid, that enhances absorption and cellular uptake. The GSH may be used to treat infectious disease, such as viruses, bacteria, and parasites (e.g., malaria), chemical and pharmaceutical toxins, radiation exposure, diabetes, and other diseases associated with suppression of GSH, either by decreased production or increased consumption. The GSH may also be used in humans over age 45 to restore youthful levels of GSH.

The technology provides a pharmaceutically acceptable glutathione formulation, comprising: at least 100 mg of reduced glutathione in powered form; at least 50 mg of crystalline ascorbic acid in powdered form, present in a quantity of at least 50% by weight with respect to the reduced glutathione; the reduced glutathione and crystalline ascorbic acid each being equilibrated at a relative humidity of about 20% or less, at a temperature of about 25° C. or less; and the equilibrated reduced glutathione and crystalline ascorbic acid being mixed under a dry gas flush to achieve a uniform mixture having triboelectrification and electrostatic association of reduced glutathione and crystalline ascorbic acid particles with each other.

Another aspect provides a pharmaceutically acceptable glutathione formulation in unit dosage form, comprising: at least 100 mg of particulate reduced glutathione; at least 50 mg of particulate ascorbic acid, present in a quantity of at least 50% by weight with respect to the reduced glutathione; a capsule, adapted to contain at least 250 mg of an electrostatically bound, uniform mixture of the reduced glutathione and the ascorbic acid at a ratio of reduced glutathione and the ascorbic acid of about 10-50% by weight; the reduced glutathione and crystalline ascorbic acid each being equilibrated prior to mixing at a relative humidity of about 20% or less, at a temperature of less than about 25° C.; and the equilibrated reduced glutathione and ascorbic acid being mixed under a dry gas flush to achieve a uniform triboelectrified mixture with electrostatic association of reduced glutathione and ascorbic acid particles, packaged under dry nitrogen.

A further aspect provides a method of formulating pharmaceutical glutathione, comprising: providing reduced glutathione in particulate form, equilibrated at a relative humidity of about 20% or less, at a temperature of about 25° C. or less; providing crystalline ascorbic acid in particulate form, equilibrated with air at a relative humidity of about 20% or less, at a temperature of about 25° C. or less; mixing a bulk quantity of the reduced glutathione and the crystalline ascorbic acid under a dry gas flush, the crystalline ascorbic acid powder being present in a quantity of at least 50% by weight with respect to the reduced glutathione, to achieve triboelectrification of the reduced glutathione and the crystalline ascorbic acid, wherein particles of the reduced glutathione become electrostatically associated with particles of the crystalline ascorbic acid to form a uniform mixture with neutralized net charge; and packaging the uniform mixture under an anoxic gas flush.

The environmental conditions may be achieved by an HVAC system in a production facility that consistently dehumidifies to a RH of less than about 20% (some excursions beyond that level are permissible, so long as the product equilibrates to a low moisture content), and temperatures below 25° C., e.g., 19-24° C. Very low temperatures, e.g., below freezing, may impair moisture removal, and are not preferred.

The formulation may comprising at least 250 mg reduced glutathione and at least 125 mg crystalline ascorbic acid, e.g., at least 500 mg reduced glutathione and at least 250 mg crystalline ascorbic acid. The reduced glutathione and crystalline ascorbic acid may be mixed under a nitrogen, argon, or $CO_2$ flush. Nitrogen is convenient and preferred. Preferably, the flush is anoxic (without molecular oxygen), to reduce oxidation. The formulation may comprise at least 95% by weight of reduced glutathione and crystalline ascorbic acid. The formulation may comprise at least 75% by weight of reduced glutathione and crystalline ascorbic acid. The formulation may consist essentially of reduced glutathione and crystalline ascorbic acid in a capsule, and in particular, in this embodiment preferably excludes oxidants, catalysts, and other materials that might reduce shelf-life. The formulation may also consist essentially of reduced glutathione, crystalline ascorbic acid, and an additional active ingredient, within a capsule.

The mixture may be packaged in a package comprising at least 100 mg of reduced glutathione and at least 50 mg of crystalline ascorbic acid. The package may comprise a unit dosage form capsule. The package may contain between about 100-500 mg reduced glutathione and between about 50-250 mg crystalline ascorbic acid in a capsule. Multiple capsules may be provided within a product package. The capsule may comprise at least 500 mg reduced glutathione and at least 250 mg crystalline ascorbic acid. The dry gas flush may comprise a nitrogen flush. The uniform mixture may comprise at least 95% by weight of reduced glutathione and crystalline ascorbic acid. The formulation may be provided substantially without any oxidant ingredients. The formulation is preferably provided substantially without a thiol odor to a human, either at time of manufacture, or before the end of the shelf-life.

The formulation may further comprise at least one of an antiviral agent, an antibiotic agent, an hyperglycemic agent, an anti-oxidant agent, a pro-oxidant agent, an anti-toxic agent, a nitric oxide precursor, a prostaglandin precursor, an anti-inflammatory agent, and an immune modulator agent.

DETAILED DESCRIPTION OF THE PREFERRED EMBODIMENTS

Example 1 Production of GSH-Ascorbic Acid Mixture

A preferred formulation of GSH according to the present invention provides capsules for oral use containing 500 mg reduced L-GSH (Kyowa Hakko "Setria"®), 250 mg USP grade crystalline ascorbic acid, and not more than 0.9 mg magnesium stearate, NF grade in an OO-type gelatin capsule. The powder may also be packaged in packets, for example containing 500 mg to 5 gm, and more preferably 1-3 grams per packet. The preferred packet preferably forms an oxygen impermeable barrier, to maintain the GSH in a substantially reduced state for at least about 2.5 years under standard temperature and pressure conditions. For example, a metallized (e.g., aluminized), heat sealable polymer film packet may be suitable.

The GSH is mixed with the ascorbic acid in a rotary mixer under dry nitrogen flush. Prior to preparation, the GSH should be stored under conditions of controlled temperature of 68-75° F. (19-24° C.) and humidity of about less than about 20% relative humidity (RH), which will tend to equilibrate with the raw material, prior to processing. It is noted that a RH as high as 30% might be tolerated, but should be actively controlled by dehumidification, so that the GSH raw material has a sufficiently low moisture content when processed. Likewise, the ascorbic acid crystals are also preferably stored at low humidity prior to processing, to ensure low humidity. These dry conditions ensure development of a high triboelectric charge on the glutathione and the ascorbic acid during the mixing, resulting in a charge transfer complex of the dry powder, which ensures consistent neutralization of the net charge and dense packing of the particles with consistent fill, in the capsule. In addition, because the GSH flakes are intimately surrounded by crystalline ascorbic acid particles, the later effectively serve as a sacrificial antioxidant for the former, both during processing and during storage. Finally, the triboelectric charging of the glutathione may lead to an enhanced susceptibility to oxidation. By excluding oxygen from the mixer, the formation of reactive-oxygen species free radical products of GSH is reduced, and the formation of glutathione dimers (GSSG) is favored. While any oxidation of the GSH is to be avoided, the GSSG has less toxicity than ROS-products of GSH, and indeed GSSG is known to be absorbed and available for hepatic reduction to GSH, though at the cost of increased metabolic load with respect to GSH administration. The ROS products of GSH oxidation are generally toxic, and to be avoided, especially where the product is to be administered to an animal or human in need of reduced GSH therapy.

According to prior technologies, at least the humidity in the facility was not effectively reduced to very low levels (e.g., maintained at 20-55% RH), resulting in inconsistent development of triboelectric charging of the particles, and therefore inconsistent density of the mixed particles, inconsistent capsule fill, possible separation of components, and inconsistent protection of the GSH from oxidation during manufacturing and storage before use. Because GSH is subject to non-specific oxidization to ophthalmic acid, a toxic desulfurated analog of GSH, particles/flakes of GSH which are not intimately bound to ascorbic acid crystal particles are more subject to oxidation, and can degrade the product over time.

In addition, it is believed that the charge transfer complex of the dry mixture is maintained after ingestion and during absorption; that is, as the capsule dissolves, the hydration results in a soluble mixture of the glutathione and ascorbic acid which retain their intimate association in solution as conjugated counterions. This, in turn, is believed to be responsible for rapid absorption of the glutathione and also rapid uptake into cells. In the absence of this charge transfer complex in the dry powder, the GSH is less rapidly absorbed, and is therefore more subject to enzymatic desurfuration to ophthalmic acid by pancreatic desulfurases, resulting in reduction of GSH, toxicity, and delayed uptake after absorption.

Thus, four distinct effects are achieved: greater shelf life, more consistent packaging of the flaky GSH powder, enhanced absorption, and enhanced cellular uptake.

Example 2 Therapeutic Regimen

The preferred regimen for treatment of humans with GSH according to the present invention is the administration of between 1 and 10 grams per day, in two divided doses, between meals (on an empty stomach), of encapsulated, stabilized GSH according to Example 1. The study detailed in Appendix B administered the GSH to HIV infected, otherwise healthy males between 18 and 65, with CD4+ cell counts above 500, not on any other medications. As detailed in Fig. 1, clinical responses were seen in the PBM intracellular GSH levels. Thus, at 1 hour after administration of a 1-gram bolus of encapsulated stabilized GSH in two 500 mg capsules, a three-fold increase in GSH was measured. It is noted that, since the human body produces large quantities of GSH, the effects of external GSH in individual cases may sometimes be masked or even appear paradoxical. However, as shown in Fig. 3, a statistical analysis shows a dose response effect of the administration of GSH to the subject population. Fig. 2 shows the response of a patient to sequential GSH doses.

Example 3 IND

In a compressed Phase I/II clinical trial (FDA IND#45012), in a well-defined GSH deficiency state, HIV infection, the composition according to Example 1 administered according to the protocol of Example 2 was demonstrated to rapidly and safely raises intracellular GSH levels two to three fold. Thus, by employing the composition according to Example 1 administered according to the protocol of Example 2, an oral pharmaceutical has been shown to treat the critical losses of GSH that are known to propel a range of major disorders. The GSH metabolism, especially the pharmacokinetics, of the subjects of the Phase II study is believed to be relatively normal. Therefore, the same regimen may be applied in the treatment of other conditions, including CHF, diabetes, early stroke or other ischemic event, toxic insult, viral infection or disease, or other condition in which free radical reactions are uncontrolled, aberrant, or contribute to pathology.

Example 4 Combination of GSH and Acetaminophen

A combination pharmaceutical is provided to ameliorate the detrimental effects of acetaminophen, a drug which consumes GSH in the liver during metabolism, and in excess doses causes liver damage due to oxidative damage. The composition includes 500 mg L-GSH, 250 mg crystalline ascorbic acid, and 350 mg acetaminophen.

Example 5 Combination of GSH and Chlorpromazine

A combination pharmaceutical is provided to ameliorate the detrimental effects of chlorpromazine, a phenothiazine drug that causes side effects, including tardive dyskinesia, possibly relating to excess free radical reactions. The composition includes 500 mg L-GSH, 250 mg crystalline ascorbic acid, and 200 mg chlorpromazine.

Example 6 Combination of GSH and Aminoglycosides

A combination pharmaceutical is provided to ameliorate the detrimental effects of Aminoglycoside drugs, which include, but are not limited to, neomycin, kanamycin, amikacin, streptomycin, gentamycin, sisomicin, netilmicin and tobramycin, a drug class which may be associated with various toxicities. This damage may be related to oxidative damage or consumption of GSH during metabolism. The composition is an intravenous formulation, including the aminoglycoside in an effective amount, and L-GSH in an amount of about 10-20 mg/kg. Ascorbic acid in an amount of 5-10 mg/kg may be added as a stabilizer.

Example 6 Vascular Disease Prophylaxis

An oral formulation is provided for prophylaxis of vascular disease, e.g., in men over 40. The composition includes 500 mg reduced L-GSH, 250 mg USP grade crystalline ascorbic acid, and 50 mg USP acetyl salicylic acid (aspirin) in an OO-type gelatin capsule. Typical administration is twice per day. Advantageously, the acetyl salicylic acid may be provided in enteric release pellets within the capsule, slowing release.

Example 7 Vascular Disease Prophylaxis

Arginine is the normal starting substrate for the production of nitric oxide. Arginine is normally in limited supply, and thus a relative deficiency of arginine may result in impaired vascular endothelial function.

An oral formulation is provided for prophylaxis of vascular disease. The composition includes 500 mg reduced L-GSH, 200 mg USP grade crystalline ascorbic acid, and 200 mg arginine, in an OO-type gelatin capsule.

Example 8 Vascular Disease Prophylaxis

Vitamin E consumption reduces the risk of heart attack and other vascular disease. Vitamin E succinate (α-tocopherol succinate) is a dry powder. An oral formulation is provided for prophylaxis of vascular disease. The composition includes 500 mg reduced L-GSH, 200 mg USP grade crystalline ascorbic acid, and 200 mg vitamin E succinate, in an OO-type gelatin capsule.

Example 9 Vascular Disease Prophylaxis

Nonspecific esterases are present in the plasma that have a broad substrate specificity. Esters are formed between agents that are useful combination therapies, in order to provide for efficient administration, high bioavailability, and pharmaceutical stability. Preferred esters include α tocopherol-ascorbate, a tocopherol-salicylate, and ascorbyl-salicylate. The tocopherol ester maintains the molecule in a reduced state, allowing full antioxidant potential after ester cleavage.

These esters may be administered alone or in combination with other agents, for example GSH. Typically, these are administered to deliver an effective dose of salicylate equivalent of 100 mg per day for prophylaxis or 750-1000 mg per dose for treatment of inflammatory diseases. Tocopherol is administered in an amount of 100-500 IU equivalent. Ascorbate is administered in an amount of up to 1000 mg equivalent. In order to enhance availability, a non-specific esterase may be provided in the formulation to cleave the ester after dissolution of the capsule. For example, a bacterial or *Saccharomyces* (yeast) non-specific esterase, such as enzyme or enriched enzyme preparation may be included, such as included as a powder or as pellets in the capsule.

Example 10 Vascular Disease Prophylaxis

Nordihydroguaretic acid is a known lipoxygenase inhibitor. This composition may therefore be used to treat inflammatory processes or as prophylaxis against vascular disease.

An oral formulation is provided for prophylaxis of vascular disease. The composition includes 500 mg reduced L-GSH, 200 mg USP grade crystalline ascorbic acid, and 100 mg nordihydroguaretic acid, in an OO-type gelatin capsule. Typical administration is twice per day.

Example 11 Prophylaxis

GSH packets containing mixed 2,500 mg reduced L-GSH, and 750 mg USP grade ascorbic acid powder are administered twice per day, by mouth, to otherwise healthy adult humans. The powder may be absorbed sublingually, swallowed as a bolus on an empty stomach, or dissolved in a liquid, such as water or orange juice, and drunk, on an empty stomach.

Example 12 Prophylaxis

GSH packets containing mixed 1,000 mg reduced L-GSH, and 500 mg USP grade ascorbic acid powder are administered, 1-2 packets, twice per day, by mouth, to otherwise healthy human children. The powder may be absorbed sublingually, swallowed as a bolus on an empty stomach, or dissolved in a liquid, such as water or orange juice, and drunk, on an empty stomach.

Example 13 Treatment

GSH is administered orally on an empty stomach, if tolerated, or intravenously, to affected individuals suffering from acute exposure to radiation or radioactive materials, biowarfare agents, chemical warfare agents, or sepsis. Dose is 5-20 grams per day, in divided doses or as a periodic or continuous infusion.

Example 14 Treatment

GSH is administered orally on an empty stomach to affected patients suffering from chronic neurological disease, including but not limited to Alzheimer's disease or Parkinson's disease. Dose is 2-10 grams per day, in two divided doses.

It should be understood that the preferred embodiments and examples described herein are for illustrative purposes only and are not to be construed as limiting the scope of the present invention, which is properly delineated only in the appended claims. The disclosures herein are intended to be considered separately, in combination, and in various subcombinations and permutations, without limitation, unless mutually incompatible.

Each reference cited herein is expressly incorporated herein by reference in its entirety.

What is claimed is:

1. A pharmaceutically acceptable glutathione formulation, comprising:
   at least 100 mg of reduced glutathione in a powdered form;
   at least 50 mg of crystalline ascorbic acid in a powdered form, present in a ratio of 10% to 50% by weight with respect to the reduced glutathione; and
   wherein the pharmaceutically acceptable glutathione formulation is a uniform mixture having triboelectrification and electrostatic association of the reduced glutathione and the crystalline ascorbic acid at a relative humidity of less than 20% at a temperature of 25° C., with neutral net charge.

2. The pharmaceutically acceptable glutathione formulation according to claim 1, comprising at least 250 mg of the reduced glutathione and at least 125 mg of the crystalline ascorbic acid.

3. The pharmaceutically acceptable glutathione formulation according to claim 1, comprising at least 500 mg of the reduced glutathione and at least 250 mg of the crystalline ascorbic acid.

4. The pharmaceutically acceptable glutathione formulation according to claim 1, wherein the pharmaceutically acceptable glutathione formulation is stable for at least 2.5 years under a standard temperature and pressure condition.

5. The pharmaceutically acceptable glutathione formulation according to claim 1, wherein the pharmaceutically acceptable glutathione formulation is present in a sealed packet impermeable to oxygen.

6. The pharmaceutically acceptable glutathione formulation according to claim 1, wherein the pharmaceutically acceptable glutathione formulation comprises at least 95% by weight of the reduced glutathione and the crystalline ascorbic acid.

7. The pharmaceutically acceptable glutathione formulation according to claim 1, comprising at least 75% by weight of the reduced glutathione and the crystalline ascorbic acid.

8. The pharmaceutically acceptable glutathione formulation according to claim 1, further comprising a capsule surrounding the reduced glutathione and crystalline ascorbic acid.

9. The pharmaceutically acceptable glutathione formulation according to claim 1, further comprising an additional active ingredient wherein the reduced glutathione, the crystalline ascorbic acid, and the additional active ingredient are present in a capsule.

10. A method of formulating the pharmaceutically acceptable glutathione formulation according to claim 1, comprising:
provided reduced glutathione in particulate form, equilibrated with air at a relative humidity of less than 20%, at a temperature of 25° C. or less;
providing crystalline ascorbic acid in particulate form, equilibrated with air at a relative humidity less than 20%, at a temperature of 25° C. or less;
mixing a bulk quantity of the reduced glutathione and the crystalline ascorbic acid under a dry gas flush, the crystalline ascorbic acid being present in a quantity of 10% to 50% by weight with respect to the reduced glutathione, wherein the reduced glutathione becomes electrostatically associated with particles of the crystalline ascorbic acid to form a uniform mixture with neutralized net charge; and
packaging the uniform mixture under an anoxic gas flush.

11. The method according to claim 10, wherein the package comprises a unit dosage form of a capsule.

12. The method according to claim 11, wherein the capsule comprises between about 100-500 mg of the reduced glutathione and between about 50-250 mg of the crystalline ascorbic acid.

13. The method according to claim 11, wherein the capsule comprises at least 500 mg of the reduced glutathione and at least 250 mg of the crystalline ascorbic acid in the capsule.

14. The method according to claim 10, wherein the dry gas flush comprises a nitrogen flush.

15. The method according to claim 10, wherein the uniform mixture comprises at least 95% by weight of the reduced glutathione and the crystalline ascorbic acid.

16. A plurality of pharmaceutically acceptable glutathione formulation capsules in a unit dosage form, comprising:
at least 100 mg of particulates of reduced glutathione;
at least 50 mg of particulates of ascorbic acid, present in a ratio of between 10% and 50% by weight with respect to the reduced glutathione;
wherein the pharmaceutically acceptable glutathione formulation is a uniform triboelectrified mixture with electrostatic association of the reduced glutathione and the crystalline ascorbic acid, having neutral net charge, and the plurality of pharmaceutically acceptable glutathione formulation capsules in a unit dosage form have uniform density.

17. The pharmaceutically acceptable glutathione formulation in a unit dosage form according to claim 16, comprising about 250-500 mg of the reduced glutathione and about 125-250 mg of the crystalline ascorbic acid, substantially without any oxidant ingredients, packed in an oxygen impermeable barrier package, having a relative humidity of less than 20% at 25° C.

18. The pharmaceutically acceptable glutathione formulation in a unit dosage form according to claim 16, wherein the pharmaceutically acceptable glutathione formulation is provided substantially without a thiol odor to a human.

19. The pharmaceutically acceptable glutathione formulation in a unit dosage form according to claim 16, further comprising at least one of an antiviral agent, an antibiotic agent, a hyperglycemic agent, an anti-oxidant agent, a pro-oxidant agent, an anti-toxic agent, a nitric oxide precursor, a prostaglandin precursor, an anti-inflammatory agent, or an immune modulator agent.

20. A pharmaceutically acceptable glutathione formulation, comprising:
at least 100 mg of reduced glutathione in a powdered form; and
at least 50 mg of crystalline ascorbic acid in a powdered form;
the crystalline ascorbic acid being present in a ratio of 10% to 50% by weight with respect to the reduced glutathione;
wherein the pharmaceutically acceptable glutathione formulation is formed by a process comprising mixing the crystalline ascorbic acid with the reduced glutathione under a dry anoxic gas at a relative humidity less than 20%, to achieve triboelectrification of the crystalline ascorbic acid and the reduced glutathione to produce a uniform dense powder mixture having neutral net charge.

* * * * *